US008585729B2

(12) United States Patent
Keith et al.

(10) Patent No.: US 8,585,729 B2
(45) Date of Patent: Nov. 19, 2013

(54) METHOD OF DILATING TISSUE OF A SINUS DRAINAGE PATHWAY

(75) Inventors: Peter T. Keith, Lanesboro, MN (US); Thomas V. Ressemann, St. Cloud, MN (US); Theodore O. Truitt, St. Cloud, MN (US)

(73) Assignee: Entellus Medical, Inc., Maple Grove, MN (US)

( * ) Notice: Subject to any disclaimer, the term of this patent is extended or adjusted under 35 U.S.C. 154(b) by 0 days.

(21) Appl. No.: 13/419,311

(22) Filed: Mar. 13, 2012

(65) Prior Publication Data

US 2012/0172912 A1 Jul. 5, 2012

Related U.S. Application Data

(60) Continuation of application No. 12/912,321, filed on Oct. 26, 2010, which is a division of application No. 11/782,620, filed on Jul. 24, 2007, now Pat. No. 7,842,062, which is a continuation of application No. 11/379,691, filed on Apr. 21, 2006, now Pat. No. 7,520,876.

(51) Int. Cl.
*A61M 29/00* (2006.01)
*A61B 5/00* (2006.01)

(52) U.S. Cl.
USPC .......................... 606/196; 606/199; 800/585

(58) Field of Classification Search
USPC .......................... 606/191, 196, 199
See application file for complete search history.

(56) References Cited

U.S. PATENT DOCUMENTS

| 759,925 A | 5/1904 | Smith |
| 2,525,183 A | 10/1950 | Robison |
| 3,312,128 A * | 4/1967 | Wasson ........................ 81/487 |
| 3,503,385 A | 3/1970 | Stevens |
| 3,800,788 A | 4/1974 | White |
| 3,949,750 A | 4/1976 | Freeman |
| 4,417,886 A * | 11/1983 | Frankhouser et al. ........ 604/510 |
| 4,509,945 A | 4/1985 | Kramann et al. |
| 4,664,113 A | 5/1987 | Frisbie et al. |
| 4,737,141 A * | 4/1988 | Spits .............................. 604/28 |

(Continued)

FOREIGN PATENT DOCUMENTS

| EP | 0129 634 A1 | 1/1985 |
| EP | 1598 015 A1 | 11/2005 |
| WO | WO 91/17787 A1 | 11/1991 |
| WO | WO 2005/086945 A2 | 9/2005 |

OTHER PUBLICATIONS

Mehta, Transtracheal Illumination for Optimal Tracheal Tube Placement, Jun. 1989, Anaesthesia, 1989, vol. 44, p. 970-972.*

(Continued)

*Primary Examiner* — Kevin C Sirmons
*Assistant Examiner* — William Carpenter
(74) *Attorney, Agent, or Firm* — Vista IP Law Group LLP

(57) ABSTRACT

A method of treating a constricted sinus passageway of a patient includes traversing the canine fossa region of the patient so as to form a passageway in the sinus cavity. An elongate member is inserted through the passageway, the elongate member having an inflation member such as a balloon disposed thereon. The inflation member is positioned within the constricted passageway. The inflation member is expanded so as to expand at least a portion of the constricted sinus passageway.

26 Claims, 40 Drawing Sheets

(56) References Cited

U.S. PATENT DOCUMENTS

| | | | |
|---|---|---|---|
| 4,748,969 A | 6/1988 | Wardle | |
| 4,757,827 A * | 7/1988 | Buchbinder et al. | 600/585 |
| 4,957,117 A * | 9/1990 | Wysham | 600/585 |
| 4,994,033 A | 2/1991 | Shockey et al. | |
| 5,021,043 A | 6/1991 | Becker et al. | |
| 5,024,658 A | 6/1991 | Kozlov et al. | |
| 5,117,839 A * | 6/1992 | Dance | 600/585 |
| 5,137,517 A * | 8/1992 | Loney et al. | 604/159 |
| 5,156,594 A | 10/1992 | Keith | |
| 5,163,911 A | 11/1992 | Sirimanne et al. | |
| 5,169,386 A | 12/1992 | Becker et al. | |
| 5,203,777 A | 4/1993 | Lee | |
| 5,396,880 A | 3/1995 | Kagan et al. | |
| 5,611,775 A | 3/1997 | Machold et al. | |
| 5,632,762 A | 5/1997 | Myler | |
| 5,645,528 A | 7/1997 | Thome | |
| 5,755,695 A * | 5/1998 | Erickson et al. | 604/164.13 |
| 5,795,325 A | 8/1998 | Valley et al. | |
| 5,827,313 A | 10/1998 | Ream | |
| 5,964,767 A | 10/1999 | Tapia et al. | |
| 6,083,188 A | 7/2000 | Becker | |
| 6,090,132 A | 7/2000 | Fox | |
| 6,113,567 A | 9/2000 | Becker | |
| 6,113,587 A | 9/2000 | Negus et al. | |
| 6,238,364 B1 | 5/2001 | Becker | |
| 6,491,940 B1 | 12/2002 | Levin | |
| 6,543,452 B1 | 4/2003 | Lavigne | |
| 6,562,022 B2 | 5/2003 | Hoste et al. | |
| 6,743,227 B2 | 6/2004 | Seraj et al. | |
| 6,752,800 B1 * | 6/2004 | Winston et al. | 604/528 |
| D501,677 S | 2/2005 | Becker | |
| 6,851,424 B2 | 2/2005 | Scopton | |
| 7,131,969 B1 | 11/2006 | Hovda et al. | |
| 7,410,480 B2 | 8/2008 | Muni et al. | |
| 7,520,876 B2 | 4/2009 | Ressemann et al. | |
| 7,559,925 B2 | 7/2009 | Goldfarb et al. | |
| 7,654,997 B2 | 2/2010 | Makower et al. | |
| 7,717,933 B2 | 5/2010 | Becker | |
| 7,842,062 B2 | 11/2010 | Keith et al. | |
| 7,879,061 B2 | 2/2011 | Keith et al. | |
| 7,918,871 B2 | 4/2011 | Truitt et al. | |
| 8,142,422 B2 | 3/2012 | Makower et al. | |
| 2001/0037051 A1 * | 11/2001 | Fujii et al. | 600/146 |
| 2002/0138121 A1 | 9/2002 | Fox | |
| 2004/0064083 A1 | 4/2004 | Becker | |
| 2004/0064150 A1 * | 4/2004 | Becker | 606/196 |
| 2004/0230289 A1 | 11/2004 | DiMatteo et al. | |
| 2005/0086945 A1 | 4/2005 | Tiemann | |
| 2005/0240147 A1 * | 10/2005 | Makower et al. | 604/96.01 |
| 2005/0245906 A1 | 11/2005 | Makower et al. | |
| 2006/0004286 A1 | 1/2006 | Chang et al. | |
| 2006/0004323 A1 * | 1/2006 | Chang et al. | 604/28 |
| 2006/0063973 A1 | 3/2006 | Makower et al. | |
| 2006/0095066 A1 | 5/2006 | Chang et al. | |
| 2006/0100687 A1 | 5/2006 | Fahey et al. | |
| 2006/0106361 A1 | 5/2006 | Muni et al. | |
| 2006/0149310 A1 | 7/2006 | Becker | |
| 2006/0210605 A1 | 9/2006 | Chang et al. | |
| 2007/0005094 A1 | 1/2007 | Eaton et al. | |
| 2007/0073269 A1 | 3/2007 | Becker | |
| 2007/0129751 A1 | 6/2007 | Muni et al. | |
| 2007/0135803 A1 | 6/2007 | Belson | |
| 2007/0250105 A1 | 10/2007 | Ressemann et al. | |
| 2008/0015472 A1 | 1/2008 | Ressemann et al. | |
| 2008/0015497 A1 | 1/2008 | Keith et al. | |
| 2008/0015544 A1 | 1/2008 | Keith et al. | |
| 2008/0015626 A1 | 1/2008 | Keith et al. | |
| 2008/0033353 A1 | 2/2008 | Truitt et al. | |
| 2008/0172033 A1 | 7/2008 | Keith et al. | |
| 2008/0249500 A1 | 10/2008 | Keith et al. | |
| 2009/0187098 A1 | 7/2009 | Makower et al. | |
| 2009/0216196 A1 | 8/2009 | Drontle et al. | |
| 2011/0040320 A1 | 2/2011 | Keith et al. | |
| 2011/0071349 A1 | 3/2011 | Drontle et al. | |
| 2011/0288477 A1 | 11/2011 | Ressemann et al. | |
| 2012/0172912 A1 | 7/2012 | Ressemann et al. | |
| 2012/0190973 A1 | 7/2012 | Ressemann et al. | |

OTHER PUBLICATIONS

Petersen, Robert, "How I Do It" Head and Neck; Sinus Puncture Therapy: Canine Fossa Puncture Method, The Laryngoscope 91: Dec. 1981 pp. 2126-2128 (3 pages).

T.G.A. Ijaduola, "Use of a Foley catheter for short-term drainage in frontal sinus surgery", The Journal of Laryngology and Otology, Apr. 1989, vol. 103, pp. 375-378 (4 pages).

Gatot, Albert, et al., "Early treatment of orbital floor fractures with catheter balloon in children", Intl. Journal of Pediatric Otorhinolaryngology, 21 (1991) pp. 97-101 (5 pages).

Tarasov, D. I. et al., "Treatment of Chronic Ethmoiditis by Intracellular Administration of Medicines to the Ethmoidal Labyrinth", Vestn Otorinolaringol, Nov.-Dec. 1978; (6):45-47 (Abstract in English) (4 pages).

Robison, J.M. "Pressure Treatment of Maxillary Sinusitis", J.A.M. A., May 31, 1952, pp. 436-440 (5 pages).

Robison, J.M.,"Pressure treatment of Purulent Maxillary Sinusitis", Texas State Journal of Medicine, May 1952, pp. 281-288 (8 pages).

Entellus Medical, 510(k) Letter (Amendment 1) and Attachments D & E, dated Mar. 13, 2008.

PCT International Search Report for PCT/US07/66187, Applicant: Entellus Medical, Inc., Forms PCT/ISA/220 and PCT/ISA/210, dated Apr. 17, 2008 (5 pages).

PCT Written Opinion for PCT/US07/66187, Applicant: Entellus Medical, Inc., Form PCT/ISA/237, dated Apr. 17, 2008 (6 pages).

PCT International Search Report for PCT/US2007/088834, Applicant: Entellus Medical, Inc.,Forms PCT/ISA/220 and PCT/ISA/210, dated May 20, 2008( 4 pages).

PCT Written Opinion for PCT/US2007/088834, Applicant: Entellus Medical, Inc., Form PCT.ISA/237, dated May 20, 2008 (10 pages).

PCT International Report on Patentability of patent application PCT/US2007/066187, Applicant: Entellus Medical, Inc., Form PCT/IB/326 and 327 and PCT/ISA/237, dated Oct. 30, 2008 (4 pages).

Petersen, Robert,"Canine Fossa Puncture", The Laryngoscope Office, Oct. 5, 1972 (3 pages).

Elidan, J. et al., "Irrigation of the Maxillary sinus by Canine Fossa Puncture Experience with 202 Patients", Ann Otol Rhinol Laryngol 92:1983, pp. 528-529 (2 pages).

Gottmann, Strohm et al., "Balloon dilatation of recurrent ostial occlusion of the frontal sinus",ECR Mar. 3, 2001. 2:00-3:30 PM Vienna Austria (1 page).

Gottmann et al., "Balloon dilatation of recurrent ostial occlusion of the frontal sinus", Abstract (B-0453) Mar. 2001, (22 pages).

Yanagisawa, Eiji et al. "Trans-canine-fossa maxillary sinoscopy for biopsy via the Stammberger technique", ENT Rhinoscopic Clinic, Aug. 2001 pp. 1-3 (3 pages).

Yanagisawa, Eiji et al. Powered Endoscopic inferior meatal antrostomy under canine fossa telescopic guidance, ENT Rhinoscopic Clinic, ENT—Ear, Nose &Throat Journa,l Sep. 2001 pp. 618-620 (2 pages).

Sathananthar, Shanmugam et al., "Canine Fossa Puncture and Clearance of the Maxillary Sinus for the Severely Diseased Maxillary Sinus", The Laryngoscope 115: Jun. 2005, pp. 1026-1029 (4 pages).

Robinson, Simon "Patterns of Innervation of the Anterior Maxilla: A Cadaver Study with Relevance to Canine Fossa Puncture of the Maxillary Sinus", Laryngoscope 115: Oct. 2005, pp. 1785-1788 (4 pages).

Bolger, William et al., "Catheter-based dilation of the sinus ostia: Initial safety and feasibility analysis in a cadaver model" Maryland Sinus Clinic, Bethesda Maryland and California Sinus Institute, Palo Alto CA, Oceanside Publications, Inc., May-Jun. 2006, vol. 20, No. 3, pp. 290-294 (5 pages).

Friedman, Michael, et al.,"Functional endoscopic dilatation of the sinuses (FEDS): Patient selection and surgical technique", Operative Techniques in Otolaryngology (2006)17, pp. 126-134 (9 pages).

(56) References Cited

OTHER PUBLICATIONS

Jones, Nick, Commetary on "Safety and Feasibility of Balloon Catheter Dilation of Paranasal Sinus Ostia: A Preliminary Investigation", Annals o Otology, Rhinology and Laryngology 115(4), pp. 300-301 (3 pages).
Bolger, William E., "Commentary Misconceptions Regarding Balloon Catheter Dilation of Paranasal Sinus Ostia", Annals of Otology, Rhinology & Laryngology 115(10): 791-792 (2006) (2 pages).
Lanza, Donald "Commentary Balloon Sinuplasty: Not Ready for Prime Time", Annals of Otology,, Rhinology and Laryngology 115(10): 789-790 (2008) (2 pages).
Brown, Christopher, et al., "Safety and Feasibility of Balloon Catheter Dilation of Paranasal Sinus Ostia: A Preliminary Investigation", Annals of Otology, Rhinology & Laryngology 155(4):293-299 (2006) (7 pages).
PCT International Preliminary Report on Patentability and the Written Opinion for PCT/US20071088834, Applicant: Entellus Medical, Inc. Forms PCT/IB/326, 373, and PCT/ISA/237 dated Jul. 30, 2009 (9 pages).
Entellus Medical, 510(k) Premarket Notification cover letter and Attachment B: Predicate Device Labeling, dated Aug. 15, 2007 (33 pages).
Folweiler, et al., "Nasal Specific Technique asPart of a Chiropractic Approach to Chronic Sinusitis and Sinus Headaches", Journal of Manipulative and Physiological Therapeutics, vol. 18, No. 1 (Jan. 1995), ( 4 pages).
Friedman, Michael, MD., et al., How I do It Rhinology A Targeted Problem and its Solution, Intraoperative and Postoperative Assessment of Frontal Sinus Patency by Transillumin.
Prosecution File History of U.S. Appl. No. 12/355,492, filed Jan. 16, 2009, Inventor: Joshua Makower: Restriction Requirement dated Oct. 9, 2009 (5 pages).
Iro, Heirich, M.D., et al., A New Device for Frontal Sinus Endoscopy: First Clinical Report, Otolaryngology, Head and Neck Surgery, vol. 125, No. 6, Dec. 2001 (4 pages).
Hoft, J.U.G., et al., Miniature Endoscopes Otorhinolaryngologic Applications, Min Invas Ther & Alied Technol 1998:7/3:209-218.
Friedman, Michael, MD., et al., How I do It Rhinology A Targeted Problem and its Solution, Intraoperative and Postoperative Assessment of Frontal Sinus Patency by Transillumination, Laryngoscope 11: Apr. 2000; 663-684.
Office Action dated Jul. 5, 2012 in U.S. Appl. No. 11/782,617, filed Jul. 24, 2007, inventor: Peter T. Keith (11pages).
Office Action dated Jul. 12, 2012 in U.S. Appl. No. 13/419,290, filed Mar. 13, 2012, inventor: Thomas V. Ressemann (10pages).
File History as of Jul. 25, 2012 for U.S. Appl. No. 12/355,492, Devices, Systems and Methods for Diagnosing and Treating Sinusitis and Other Disorders of the Ears, Nose and/or Throat, Inventor: Joshua Mokower, et al., filed Jan. 16, 2009 (427 pages).
File History of U.S. Appl. No. 11/782,617, Method for Accessing a Sinus Cavity and Related Anatomical Features, Inventor: Peter T. Keith, et al., filed Jul. 24, 2007.
Restriction Requirement dated Oct. 8, 2009 in U.S. Appl. No. 11/782,617, filed Jul. 24, 2007, inventor: Peter T. Keith, (5pages).
Office Action dated Jul. 6, 2010 in U.S. Appl. No. 11/782,617, filed Jul. 24, 2007, inventor: Peter T. Keith, (36pages).
Final Office Action dated Mar. 16, 2011 in U.S. Appl. No. 11/782,617, filed Jul. 24, 2007, inventor: Peter T. Keith, (7pages).
Office Action dated Jul. 5, 2012 in U.S. Appl. No. 11/782,617, filed Jul. 24, 2007, inventor: Peter T. Keith, (11pages).
Final Office Action dated Apr. 15, 2003 in U.S. Appl. No. 11/782,617, filed Jul. 24, 2007, inventor: Peter T. Keith, (19pages).
File History of U.S. Appl. No. 13/197,639, Guide Catheter and Method of Use, Inventor Thomas V. Ressemann, et al., filed Aug. 3, 2011.
Restriction Requirement dated Jun. 11, 2013 in U.S. Appl. No. 13/197,639, filed Aug. 3, 2011, inventor: Thomas V. Ressemann et al., (8pages).
File History of U.S. Appl. No. 13/419,290, Method of Confirming Location of Guire Wire, Inventor: Thomas V. Ressemann, et al., filed Mar. 13, 2012.
Office Action dated Jul. 12, 2012 in U.S. Appl. No. 13/419,290, filed Mar. 13, 2012, inventor Thomas V. Ressemann, et al., (9pages).
Office Action dated Dec. 10, 2012 in U.S. Appl. No. 13/419,290, filed: Mar. 13, 2012, inventor: Thomas V. Ressemann, et al., (27pages).

\* cited by examiner

METHOD OF DILATING TISSUE OF A SINUS DRAINAGE PATHWAY

RELATED APPLICATIONS

This Application is continuation of U.S. application Ser. No. 12/912,321 filed on Oct. 26, 2010, which is a divisional of U.S. application Ser. No. 11/782,620 filed on Jul. 24, 2007, now issued as U.S. Pat. No. 7,842,062, which is a continuation of U.S. application Ser. No. 11/379,691 filed on Apr. 21, 2006, now issued as U.S. Pat. No. 7,520,876. Priority is claimed pursuant to 35 U.S.C. §120 and all other applicable statutes. The above-noted Applications are incorporated by reference as if set forth fully herein.

FIELD OF THE INVENTION

The field of the invention generally relates to devices and methods for the treatment or amelioration of sinusitis.

BACKGROUND OF THE INVENTION

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed. These paired cavities are located in the skull behind the face, as is depicted in FIGS. 1, 2, and 3A. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has an opening into the nasal passage called an ostium. When the mucosa of one or more of the ostia or regions near the ostia become inflamed, the egress of mucous is interrupted, setting the stage for an infection of the sinus cavity, i.e., sinusitis. Infections of the maxillary and/or ethmoid sinuses make up the vast majority of cases of sinusitis, with far fewer cases involving the sphenoids and frontals.

Though many instances of sinusitis may be treatable with antibiotics, in some cases sinusitis persists for months, a condition called chronic sinusitis. Some patients are also prone to multiple episodes of sinusitis in a given period of time, a condition called recurrent sinusitis.

Currently, patients experiencing chronic sinusitis are eligible to have a surgical procedure called functional endoscopic sinus surgery (FESS). In this procedure, which almost always done in an operating room setting with the patient under general anesthesia, surgical cutting instruments are guided with an endoscopic visualization tool to the various sinus ostia and adjacent regions. Inflamed mucosa and underlying bony tissue are cut away in an effort to widen the outlet of the sinuses of interest. Once opened, the infected sinuses are able to drain and return to a relatively normal state.

While this procedure is generally effective, it is a relatively invasive procedure to the nasal cavity and sinuses. There can be significant post-operative pain for the patient, and sometimes there are bleeding complications that require packing to be placed in the nasal cavity. Subsequent removal of this packing can be quite painful. Also, since the nasal and sinus tissue are significantly traumatized, it may take several days to weeks to know whether the surgery was successful. This is especially true if various healing agents such as MeroGel® (Medtronic/Xomed) were placed at the surgical site, as these often block the sinus drainage until they are flushed away or degrade away after several days.

Additionally, in certain patients, the ostial regions of the surgically-treated sinuses can become re-obstructed with excess growth of scar tissue as a result of the tissue trauma. When the advantages and disadvantages of the surgery are considered for a patient with sinusitis, there are many patients in whom the surgery may not be appropriate. For example, their condition may not be considered "chronic enough" or extensive enough to warrant FESS surgery. In other situations, the patient may be fearful of the pain or other aspects of having FESS performed. Alternatively, the FESS procedure may be too costly for a particular patient.

For these and other reasons, there is a clear need for better methods and devices for the treatment of sinusitis.

SUMMARY OF THE INVENTION

In a first aspect of the invention, a method of treating a constricted sinus passageway of a patient includes traversing the canine fossa region of the patient so as to form a passageway to a sinus cavity. An elongate member having an inflation member thereon (e.g., a balloon) is inserted through the passageway. The inflation member is positioned within the constricted sinus passageway. The inflation member is then expanded so as to expand at least a portion of the constricted sinus passageway.

In a second aspect of the invention, a method of accessing a constricted sinus passageway of a patient includes traversing the canine fossa region of the patient to as to form a passageway to a sinus cavity. A visualization tool is inserted through the passageway. A wire guide is also inserted through the passageway. The constricted sinus passageway is viewed with the visualization tool. The wire guide is positioned adjacent to or within the constricted sinus passageway.

In another aspect of the invention, a method of accessing a constricted sinus passageway of a patient includes traversing the canine fossa region of the patient so as to form a first passageway to a sinus cavity. A visualization tool is inserted through the first passageway. The canine fossa region is traversed again to form a second passageway. This traversal may be performed at the same time that the first passageway is formed. A wire guide is then inserted through the second passageway. The constricted sinus passageway is then viewed with a visualization tool. The wire guide is then placed adjacent to or within the constricted sinus passageway. A balloon catheter may be advanced over the wire guide to expand or open the constricted sinus passageway.

In yet another embodiment, a method of accessing a constricted sinus passageway of a patient includes traversing the canine fossa region of the patient so as to form a passageway to a sinus cavity. An illumination member is inserted into the sinus cavity. The sinus cavity is illuminated via the illumination member. A guide catheter is inserted through the nasal passageway, the guide catheter including a wire guide slidably disposed within a lumen contained therein. A visualization tool is inserted through the nasal passageway. A distal tip of the wire guide is placed across or adjacent to the constricted sinus passageway.

In still another aspect of the invention, a method of confirming the location of a wire guide intended to be positioned within a patient's sinus cavity includes introducing a wire guide through a nasal passageway to place a distal tip of the wire guide in a test position. The elongate member is advanced over the wire guide to place a distal end at or adjacent to the distal tip of the wire guide. The elongate member emits illuminating light via the distal end of the elongate member. The location of the light (e.g., the source) is viewed through the patient's skin to confirm the positioning (or confirm incorrect positioning) of the wire guide.

In another embodiment of the invention, a method of confirming the location of the wire guide intended to be positioned within a patient's sinus cavity includes introducing a wire guide through a nasal passageway to place a distal tip of the wire guide in a test position, the wire guide including a detection element positioned at or adjacent to the distal tip of the wire guide. A detector device is then placed external to the patient's skin adjacent to the intended sinus cavity so as to detect the presence or absence of the detection element.

In still another aspect of the invention, a system for accessing a sinus cavity of a patient includes a trocar having an outer cannula and a piercing member slidably disposed within a lumen of the cannula. The system includes an elongate member having an inflation member disposed thereon, the elongate member being slidably disposed within the lumen of the cannula.

In yet another aspect of the invention, a device for accessing the sinus cavity of a patient includes an outer cannula having a lumen and a piercing member slidably disposed within the lumen of the cannula. An adjustable stop is secured to a distal portion of the piercing member.

In still another aspect of the invention, a device for accessing the sinus cavity of a patient includes an outer cannula having a lumen and a piercing member slidably disposed within the lumen of the cannula. A stop is secured to one of the outer cannula and the piercing member.

In another aspect of the invention, a device for accessing the sinus cavity of a patient includes an outer cannula having a lumen, a piercing member slidably disposed within the lumen of the cannula, the piercing member including a threaded portion on a proximal section of the piercing member. The device further includes a threaded hub configured to rotationally engage the threaded portion of the piercing member.

In still another aspect of the invention, a device for accessing the sinus cavity of a patient includes an outer cannula having a lumen, a piercing member slidably disposed within the lumen of the cannula, the piercing member including a proximal section. The device further includes an advancement member frictionally engaged with the proximal section of the piercing member, wherein the advancement member controls the displacement of the piercing member relative to the outer cannula.

In yet another embodiment of the invention, a balloon catheter for treating a constricted sinus passageway of a patient includes a flexible elongate member having a proximal end and a distal end and including first and second lumens passing therethrough. A hub is secured to a proximal end of the flexible elongate member, the hub including a first port in communication with the first lumen of the flexible elongate member and a second port in communication with the second lumen of the flexible elongate member. An inflation member is disposed on or adjacent to the distal end of the flexible elongate member, an interior of the inflation member being in communication with the first lumen of the flexible elongate member. An outer membrane surrounds the inflation member, an interior of the outer membrane being in communication with the second lumen of the flexible elongate member, the outer membrane including a plurality of perforations.

In still another embodiment of the invention, a stabilizing device for securing one or more tools passing into a nasal or sinus cavity of a patient includes a base member fixedly secured to the face of the patient, an adjustable support arm secured at a first end to the base member, and a securing member fixed to a second end of the adjustable support arm, the securing member configured to releasable hold at least one tool passing into the nasal or sinus cavity of a patient.

In another embodiment of the invention, a method of stabilizing one or more tools passing into a nasal passage of a patient includes inserting a tool into the nasal passage of the patient. A stabilizing element is then inserted into the nasal passage of the patient adjacent to the tool, the stabilizing element being inserted in a non expanded state. The stabilizing element is expanded to an expanded state to frictionally engage the tool within the nasal passage of the patient.

In another embodiment of the invention, a stabilizing device for securing one or more tools passing into a sinus cavity of a patient includes a mouth piece fixedly secured to the mouth of the patient, an adjustable support arm secured at a first end to the mouth piece, and a securing member fixed to a second end of the adjustable support art, the securing member configured to releasably hold at least one tool passing into the sinus cavity of a patient.

In still another aspect of the invention, a system for manipulating a guide catheter within a patient's nasal passages or sinus cavities is provided. The system includes a guide catheter formed from an elongate flexible member having a lumen passing therethrough and a wire guide slidably disposed within the lumen of the guide catheter. The system includes a steering member fixedly secured to a proximal end of the wire guide and a proximal hub secured to a proximal end of the guide catheter. The system further includes a recessed handle having a first recess for fixedly receiving the proximal hub of the guide catheter and a second recess for receiving the steering member, the second recess being dimensioned to permit axial and rotational movement of the steering member while disposed in the second recess.

In yet another aspect of the invention, a system for manipulating a guide catheter within a patient's nasal passages or sinus cavities is provided. The system includes a guide catheter formed from an elongate flexible member having a lumen passing therethrough, the guide catheter including a proximal handle including a recess therein. A wire guide is slidably disposed within the lumen of the guide catheter. The system includes a steering member fixedly secured to a proximal end of the wire guide and disposed in the recess of the handle, the recess being dimensioned to permit axial and rotational movement of the steering member while disposed in the recess.

In another embodiment of the invention, a guide catheter for accessing a sinus cavity of a patient includes an elongate member having a proximal end and distal end and at least one lumen passing therethrough, the distal end including a flexible tip portion, the elongate member being formed from a polymeric material containing a wire braid. The guide catheter further includes a hub connected to the proximal end of the elongate member.

In still another aspect of the invention, a balloon catheter for treating a constricted sinus passageway of a patient includes an elongate flexible shaft comprising an inner tube and an outer tube, the elongate flexible shaft having a proximal end and distal region, wherein at least one of the inner tube and outer tube is formed with a kink-resistant coil in the distal region. A hub is affixed to a proximal end of the elongate flexible shaft, the hub including a port in communication with a lumen formed between the inner tube and the outer tube. An expandable member is disposed on a distal region of the elongate flexible shaft, an interior of the expandable member being in communication with the lumen formed between the inner tube and the outer tube.

In another embodiment of the invention, a guide catheter for guiding one or more devices into an ostium of a paranasal sinus includes an elongate shaft defining a proximal region and a distal region, the elongate shaft including a lumen passing from the proximal region to the distal region. The elongate shaft includes a curved portion in the distal region, the curved portion having a radius of curvature of between about 1 mm and about 5 mm and an angle of between about 120° and about 180°.

In still another aspect of the invention, a method of placing a wire guide into the ostium of a paranasal sinus includes introducing a directable endoscope into the nasal cavity. A guide catheter is inserted into the nasal cavity to position a distal tip near the sinus ostium. The endoscope is manipulated to move the viewing field toward the sinus ostium. A wire guide is inserted through a lumen in the guide catheter and the wire guide is manipulated to place the same at least partially within or adjacent to the sinus ostium.

In another embodiment of the invention, a method of placing a wire guide into the ostium of a paranasal sinus includes introducing a retrograde rigid endoscope into the nasal cavity and introducing a guide catheter into the nasal cavity to position a distal tip near the sinus ostium. The endoscope is oriented to move the viewing field toward the sinus ostium. A wire guide is inserted through a lumen in the guide catheter and the wire guide is manipulated to place the wire guide at least partially within or adjacent to the sinus ostium.

In yet another embodiment of the invention, a method of placing a wire guide into the ostium of a paranasal sinus includes introducing a guide catheter into the nasal cavity to position a distal tip near the sinus ostium. A wire guide is inserted through a lumen in the guide catheter and the wire guide is manipulated to place the wire guide at least partially beyond a distal tip of the guide catheter. A flexible visualization scope is introduced over the wire guide to position a viewing field toward the sinus ostium. The wire guide is manipulated to place the wire guide at least partially within the sinus ostium.

In still another aspect of the invention, a method of placing a wire guide into the ostium of a paranasal sinus includes introducing a directable endoscope sheath into the nasal cavity, the endoscope sheath including at least one working lumen therein. The endoscope is manipulated to move the viewing field toward the sinus ostium. A wire guide is inserted through the lumen in the endoscope sheath. The wire guide is manipulated to place the wire guide at least partially within or adjacent to the sinus ostium.

In yet another aspect of the invention, a method of remodeling the uncinate process associated with a paranasal sinus includes positioning at least one shim member in the infundibulum, the shim member deforming the uncinate process and widening at least a portion of the infundibulum. The shim member may be permanent or biodegradable. In addition, multiple shims may be positioned within the infundibulum. The at least one shim members may be delivered using a delivery tool. For example, the at least one shim member may be inserted into the infundibulum in a first orientation and then rotated into position. The at least one shim member may include a gripping member (e.g., teeth) on an exterior surface thereof.

In another aspect of the invention, a device for remodeling the uncinate process associated with a paranasal sinus includes an elongate delivery tool and at least one shim member detachably mounted to a distal end of the elongate delivery tool. The elongate delivery tool may include a torque driver to transmit rotational movement of a proximal end to rotational movement of a distal end. In one aspect, the at least one shim member and the elongate delivery tool are slidably disposed within a guide catheter.

In another embodiment of the invention, a method of treating a constricted sinus passageway of a patient includes traversing the external skull wall of the patient so as to form a passageway to the frontal sinus cavity and inserting an elongate member through the passageway, the elongate member having an inflation member disposed thereon. The inflation member is positioned within the constricted sinus passageway and the inflation member is expanded so as to expand at least a portion of the constricted sinus passageway.

In still another embodiment of the invention, a device for accessing the sinus cavity of a patient includes an outer cannula having a lumen, the outer cannula having a flexible curved tip. The device further includes a piercing member slidably disposed within the lumen of the cannula, the piercing member including a proximal section. An advancement member is frictionally engaged with the proximal section of the piercing member.

Further features and advantages will become apparent upon review of the following drawings and description of the preferred embodiments.

DETAILED DESCRIPTION OF THE PREFERRED EMBODIMENTS

Figure 1:
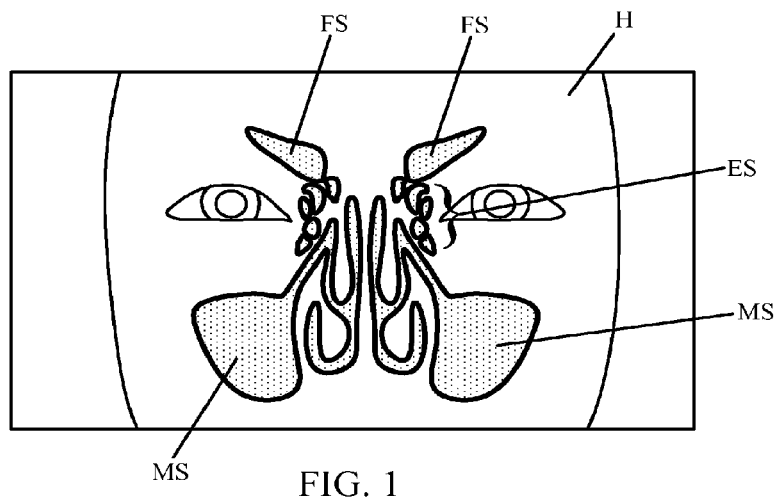
FIG. 1 illustrates is a schematic view illustrating the paranasal sinuses in relation to the face.

FIG. 1 illustrates a frontal anatomical representation (parallel to the coronal plane) showing the sinuses FS, ES, MS located within a patient's head H. Above and behind the eyebrows are the frontal sinuses FS. Between the eyes are the ethmoid sinuses ES. Note that unlike the other sinuses, the ethmoids are typically formed as a "honeycombed" structure consisting of several individual air cells. Located behind the cheeks are the maxillary sinuses MS. The sphenoid sinuses are not shown in FIG. 1, but are located further posterior to the ethmoid sinuses.

Figure 2:
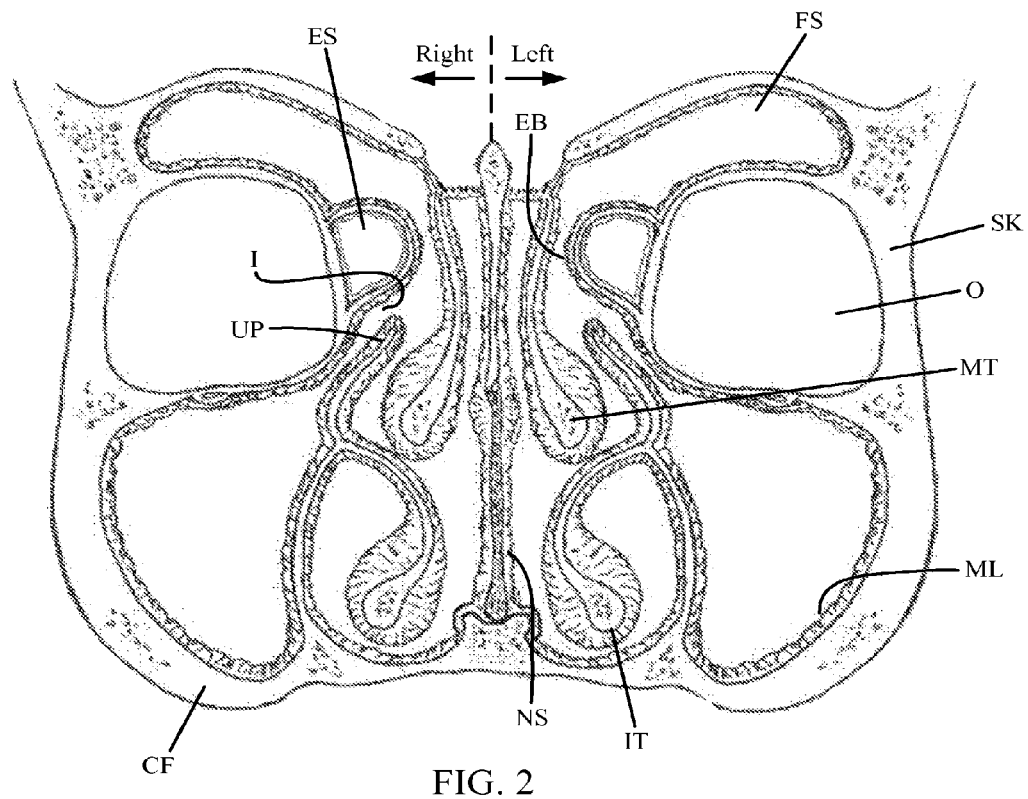
FIG. 2 is a coronal section of the human skull, showing the paranasal sinuses.

FIG. 2 is another frontal view of the sinuses located within the skull bone SK showing additional features. The nasal septum NS divides the nasal cavity into left and right sides. Because the following described structures are generally symmetrical bilaterally, only one of the paired structures is illustrated for sake of convenience. Within the nasal cavity are the middle turbinate MT and the inferior turbinate IT. The middle turbinate MT is connected to the base of the skull SK, while the inferior turbinate IT is connected to the lateral wall of the sinus cavity. The turbinates MT, IT have an underlying bony structure, but are covered with a thick mucosa lining. When this lining swells (rhinitis), it can inhibit breathing through the nose, particularly the inferior turbinate IT. The ethmoid sinuses ES are depicted by a single air cell in FIG. 2. The uncinate process UP is a complex three-dimensional structure, projecting off of the lateral wall like a crescent shaped leaf (better seen in FIGS. 3B and 25B) The curved aspect of the medial bone defining the ethmoid sinuses ES is called the ethmoid bulla EB. The passageway between the ethmoid bulla EB and the uncinate process UP is referred to as the infundibulum I. The drainage path of the maxillary MS, frontal FS, and some of the ethmoid ES air cells runs into the infundibulum I. At the most inferior part of the maxillary sinus is a thin portion of skull bone referred to as the canine fossa CF. Though this is not a true opening, it is a relatively thin bone region, just above the root of the outer aspect of the canine teeth, inside the mouth. The relationship of the sinuses to the orbit O of the eye can also be seen. Note also that all of the sinus cavities have a mucosa lining (ML) disposed over the bone.

Figure 3A:
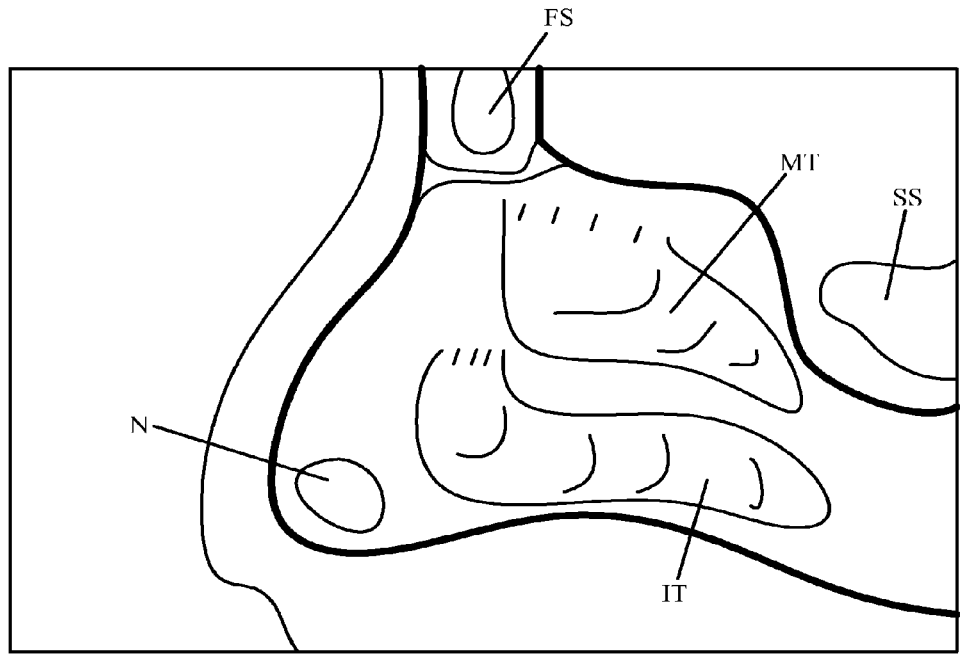
FIGS. 3A-3C are of a sagittal view of the lateral nasal wall, illustrating various anatomical features thereof.
Figure 3B:
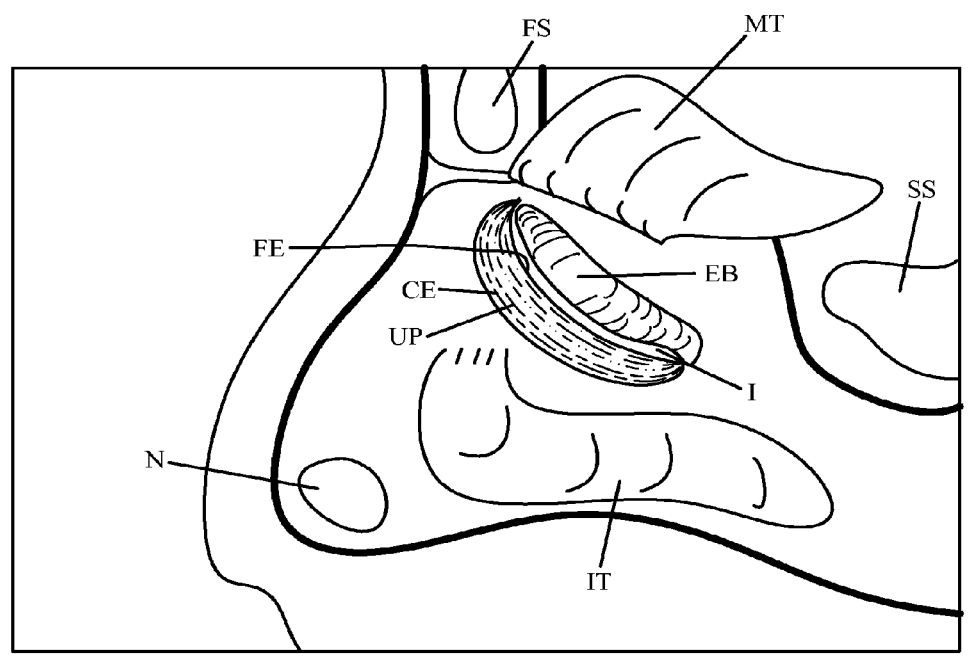

FIG. 3A is a side view parallel to the sagittal plane, looking at the right lateral nasal wall. The right nostril N is seen. The sphenoid sinus SS and frontal sinus FS may also be seen in this view. The flap-like structures illustrated in FIG. 3A are the inferior turbinate IT and middle turbinate MT. Other structures of the nasal cavity have been left out for clarification, e.g., the superior turbinate. Located underneath the middle turbinate MT (shown in a "lifted" state in FIG. 3B and removed in FIG. 25B) are the structures of the lateral nasal wall. As seen in FIG. 3A, the ethmoid bulla EB is a rounded projection of the bony wall of the nasal cavity. Behind the wall of the ethmoid bulla EB are one or more of the individual air cells of the ethmoid sinus ES (not shown in FIGS. 3B and 25B). Anterior and inferior of the ethmoid bulla is the uncinate process UP. The uncinate process UP has essentially two edges to it including a free edge FE and a connected edge CE. The free edge FE stands out from the nasal wall, while the connected edge CE connects the structure to the nasal wall. The narrow space between the ethmoid bulla EB and the uncinate process UP is the infundibulum I. Thus, it can be appreciated the complexity of the anatomy involving the maxillary and ethmoid sinus structures MS, ES.

Figure 3C:
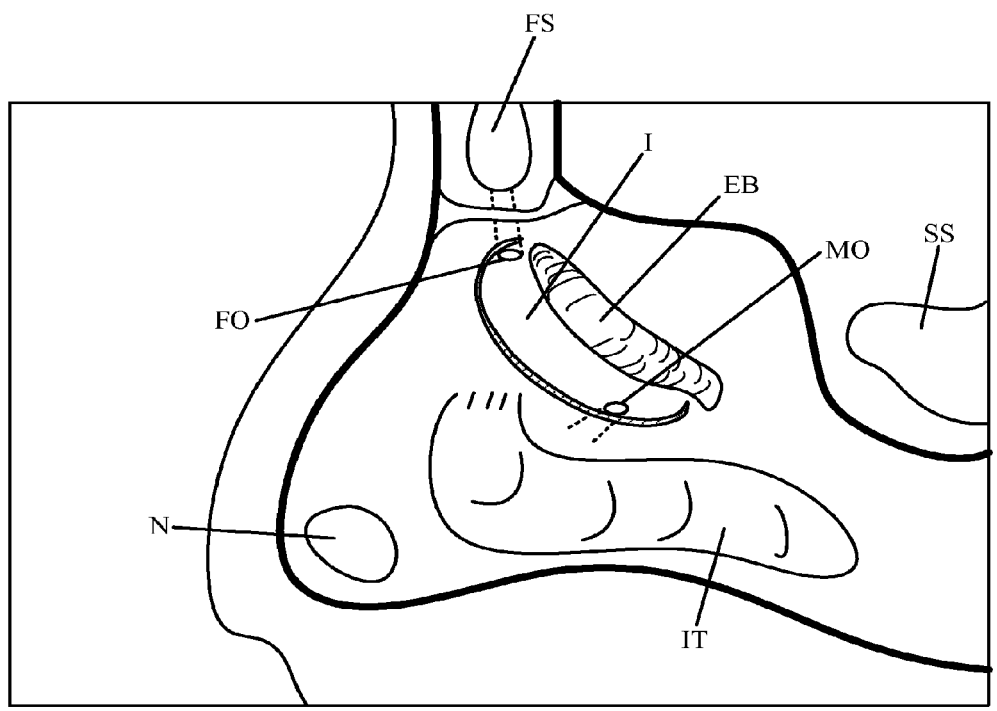

FIG. 3C illustrates the structure beneath or underneath the uncinate process UP. In FIG. 3C, the uncinate process UP has been removed for clarity purposes, leaving only the connected edge CE. Two ostia can be seen including the maxillary sinus ostium MO, and the frontal sinus ostium FO. Drainage from the frontal sinuses FS and maxillary sinuses MS emerges into the infundibulum I through the maxillary sinus ostium MO and the frontal sinus ostium FO. Also, some of the ethmoid air cells ES drain into the infundibulum I, but they are not shown as they are substantially smaller than the frontal and maxillary ostia FO, MO. Drainage problems can arise and/or extend from the ostia of one or more of these sinuses to the infundibulum I or vise versa. Consequently, conventional FESS surgical treatment of sinusitis typically involves widening one or more of the ostia FO, MO, as well as complete removal of the uncinate process UP. Incidentally, removal of the uncinate process UP is usually required even to just allow visualization of these sinus ostia FO, MO for the proper placement of the various surgical cutting instruments. Ethmoids are often treated with the FESS procedure by removing some of the wall of the ethmoid bulla EB and some of the "honeycomb" structure between the individual air cells.

Figure 4:
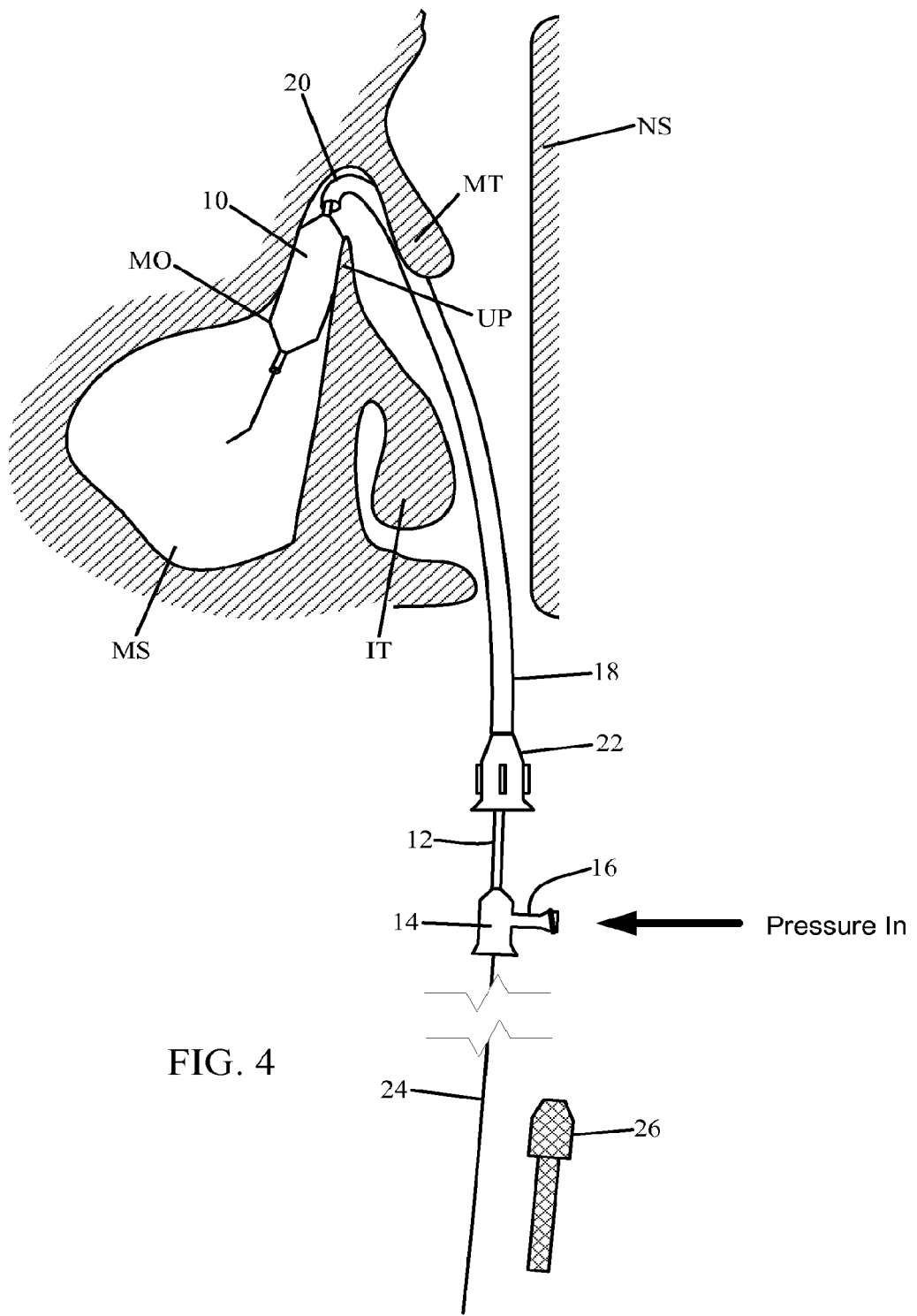
FIG. 4 illustrates one embodiment of the current invention showing a balloon dilation catheter in the ostial region of a paranasal sinus.

FIG. 4 illustrates a generic therapeutic approach contemplated by one embodiment of the invention. Rather than remove obstructing tissue associated with the sinus ostia FO, MO, a dilation balloon 10 is positioned in the narrowed region to dilate open the structure. Generally, the dilation balloon is carried on a distal end or region of elongate member 12 such as a balloon catheter. The balloon catheter 12 may include a proximal hub 14 that includes an inflation port 16 that is used inflate (and deflate) the dilation balloon 10. For example, the inflation port 16 may connect to a syringe or the like (not shown) using, for instance, a Leur lock connection. The balloon catheter 12 may be disposed within a central lumen of a guide catheter 18. The guide catheter 18 may include a flexible tip portion 18b as well as a curved portion 20 that is used to navigate the tortuous pathway around the uncinate process UP. The proximal end of the guide catheter 18 may include a hub 22.

Still referring to FIG. 4, a wire guide 24 is located within a central lumen in the balloon catheter 12. The wire guide 24 in FIG. 4 is introduced into the maxillary sinus MS with the aid of the guide catheter 18 and a steering device 26. The wire guide 24 preferably has a curved tip 24b such as a "J" bend located at or adjacent to a distal tip 24a of the wire guide 24. The steering device 26 connects to a proximal end of the wire guide 24 to allow rotation of the wire guide 24, and subsequent rotation of the curved tip 24b to steer and direct the wire guide 24. As can be seen in FIG. 4, there is a relatively sharp bend that the wire guide 24 and balloon catheter 12 must traverse to enter into the maxillary ostial MO region. It is contemplated that a guide catheter 18 may not be utilized at the time that the balloon catheter 12 is positioned in the ostium of interest, but rather the guide catheter 18 would be utilized just for placement of the wire guide 24. In this case, the balloon catheter 12 would be advanced over the wire guide 24. This helps to minimize the size of the "hardware" that is present in the nasal cavity at any one time by allowing use of a smaller diameter guide catheter 18, and minimizes the amount of distortion required on various structures in the nasal cavity, such as the middle turbinate MT.

Still referring to FIG. 4, dilation of the maxillary ostial MO region is accomplished by inflation of the balloon 19 via the inflation port 16 with an inflation apparatus (not shown) which may included, for example, a syringe. It is contemplated that a combination of remodeling the soft tissues as well as fracturing/crushing bony tissues will result in a more open drainage path for the sinus(es) being treated. While FIG. 4 shows a balloon catheter 12 positioned in the maxillary sinus ostium (MO), it is contemplated that the balloon 10 could be positioned in any of the sinus ostia, either naturally occurring ostia, or ostia created intra-procedurally. In particular, treatment of the ethmoid air cells ES may be accomplished by creating one or more small passageways in the walls surrounding the air cells, for example with a needle, followed up by a dilation process using the dilation balloon catheter 12. Moreover, reference to a particular ostium does not necessarily mean an opening or passageway per se. Rather, reference to ostium may include the general region or anatomical area surrounding or adjacent to the ostium of interest and is not limited to a single, discrete structure or location.

Figure 5A:
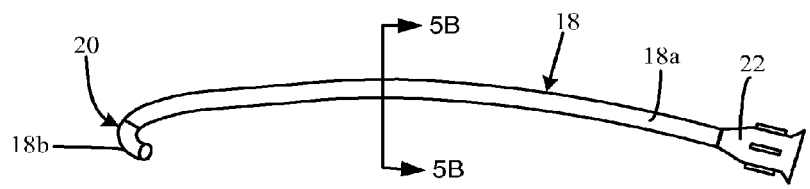
FIG. 5A illustrates one embodiment of a guide catheter according to the invention.
Figure 5B:
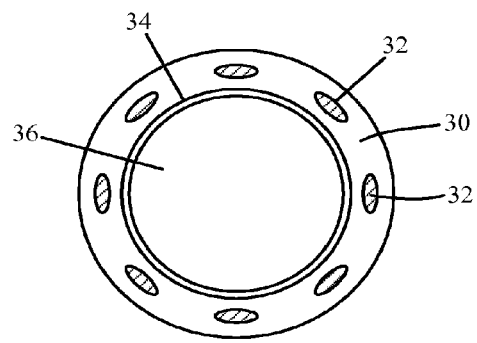
FIG. 5B is a cross-sectional view of the embodiment shown in FIG. 5A.

Access to the maxillary sinus ostium MO from within the nasal cavity is particularly challenging due in part to the anatomy of the uncinate process UP and infundibulum I. FIGS. 5A and 5B illustrate various embodiments of a guide catheter 18 used to facilitate access to the maxillary sinus from the nasal cavity. In FIG. 5A, the guide catheter 18 has a relatively tight curved portion 20 near the tip 18b, with a preferred inside radius of curvature between about 0.5 mm and about 10 mm, and more preferably between about 1 mm and about 5 mm. Such a radius of curvature will assist in the tip 18b of the guide catheter "hooking" around the uncinate process UP, to help direct the wire guide 24 and subsequently the balloon catheter 12 into the maxillary sinus ostium MO. The degree of bend of the curved portion of the guide catheter 18 is preferably between 90 degrees and 180 degrees from the longitudinal axis of the hub 22, and more preferably between 120 and 160 degrees.

In one preferred aspect of the invention, the guide catheter 18 includes a shaft portion 18a and a flexible tip portion 18b. The tip portion 18b is preferably of a softer material than the shaft portion 18a. Tip portion 18b may formed of a polymer such as PEBAX (Arkema), polyurethane, NYLON (DuPont), HYTREL (DuPont), or silicone. FIG. 5B illustrates a cross-sectional view of one preferred embodiment of the shaft portion 18b. As seen in FIG. 5B, a liner 34 of a lubricious material such as PTFE defines a central lumen 36. The liner 34 is surrounded by a wire braid 32. The wire braid 32 is encased in a polymeric material such as PEBAX (Arkema), polyurethane (DuPont), NYLON (DuPont), HYTREL (DuPont), or silicone. The wire braid 32 adds torsional strength to the shaft 18, allowing the curved tip portion 18b to be controlled and directed by manipulations near the hub 22. The tip portion 18b may be pre-formed by a suitable process such as heat forming.

Alternatively, as shown in 5C, the guide catheter 18 shaft portion 18a and/or tip portion 18b may incorporate a shaping element 38, such as a removable wire. The wire 38 is preferably axially slidable within a lumen 40 formed in the guide catheter 18. For example, different pre-shaped wires 38 may be axially slid within the lumen 40 to impart the desired shape or bend in the guide catheter 18. Alternatively, shaping element 38 could be a ductile non-removable wire that could be shaped and re-shaped to fit to a particular patient's anatomy. This feature advantageously allows the tip curvature or the curvature of any portion of the guide catheter 18 to be customized by the user prior to or during a procedure.

Figure 5C:
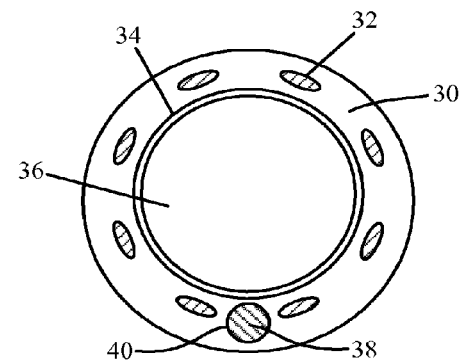
FIG. 5C is a cross-sectional view of an alternative embodiment of a guide catheter.

Alternatively, the shaft portion 18b of the guide catheter 18 can be formed of a metallic tube rather than the braid and jacket construction. This embodiment is illustrated in FIG. 5F. Preferably a liner 34 is inside the metallic tube. Such a construction would allow the shaft portion 18b to be shaped and reshaped to suit any particular anatomy.

The diameter of the guide catheter 18 is determined by the size of the devices that might pass through it. For example, if the guide catheter 18 is used only for the placement of a wire guide 24 of 0.014 inch diameter, then the guide catheter 18 may have an inner diameter of between 0.016 and 0.025 inches, and a total wall thickness of between 0.004 and 0.020 inches. However if the guide catheter 18 is used to assist in placement of a dilation balloon catheter 12, the inner diameter is preferably between 0.040 and 0.100 inches, with a total wall thickness of between 0.005 and 0.030 inches. The outer diameter of the guide catheter shaft 18a and tip 18b is preferably uniform in diameter. The length of the guide catheter 18 is preferably between about 8 and about 25 cm, and more preferably between about 10 and about 20 cm.

Figure 5D:
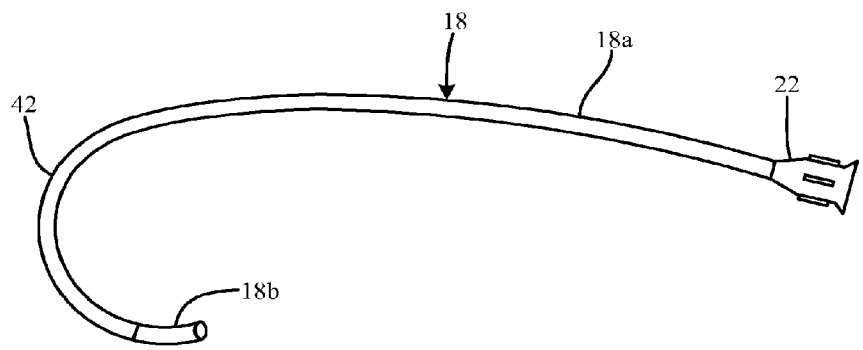
FIG. 5D is an alternative embodiment of a guide catheter.

FIG. 5D illustrates another embodiment of a guide catheter 18 that is particularly useful for cannulating the maxillary sinus ostium MO. In this embodiment, the curved portion 42 is of a substantially larger radius of curvature compared to the embodiment shown in FIG. 5A. Rather than take a "direct" path up to and around the uncinate process UP, the embodiment shown in FIG. 5D makes use of the significant anterior-posterior space in the nasal passage NP. The curvature 42 of the guide catheter 18 may be formed using a shaping element 38 of the type disclosed in FIG. 5C.

Figure 5E:
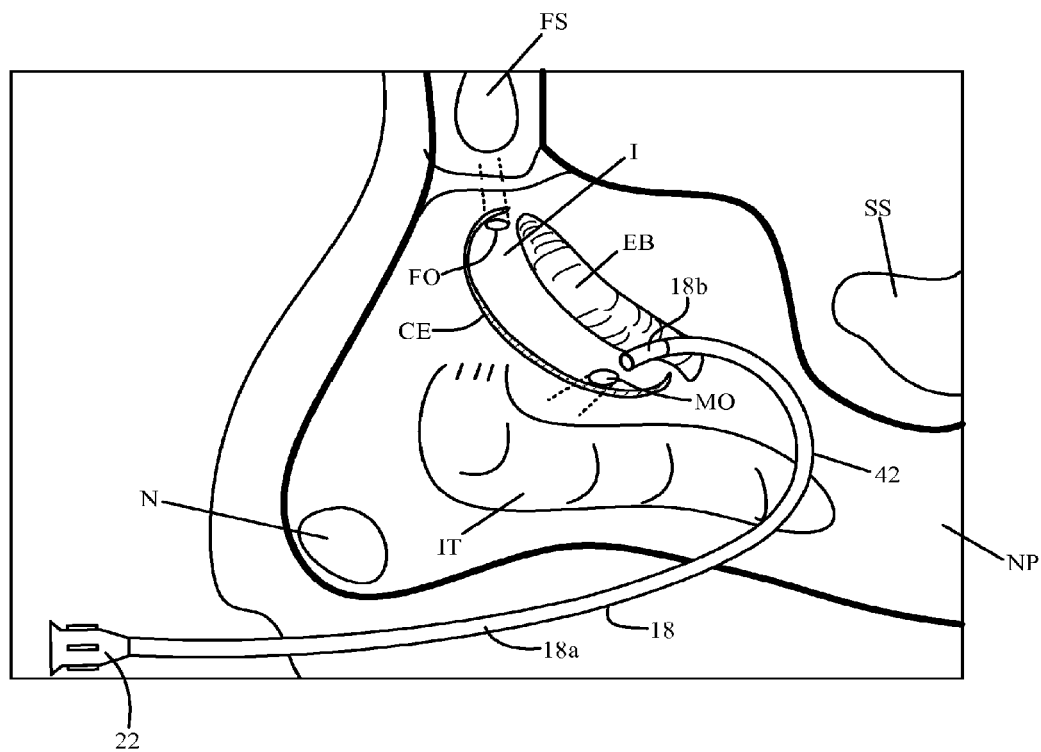
FIG. 5E shows the guide catheter of the embodiment illustrated in FIG. 5D being positioned within the nasal cavity.
Figure 5F:
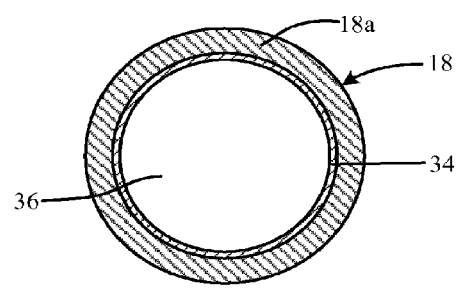
FIG. 5F is a cross-sectional view of an alternative embodiment of a guide catheter.

FIG. 5E illustrates how the guide catheter 18 shown in FIG. 5D makes a more gradual sweeping turn in the nasal cavity to reach towards the maxillary sinus ostium MO. By possessing a larger radius of curvature, any devices used inside this guide catheter 18 are not forced to negotiate such a tight bend. In a preferred embodiment, the inside radius of curvature is preferably between about 1 cm and about 3 cm, and more preferably between about 1.5 and about 2.5 cm.

Figure 6A:
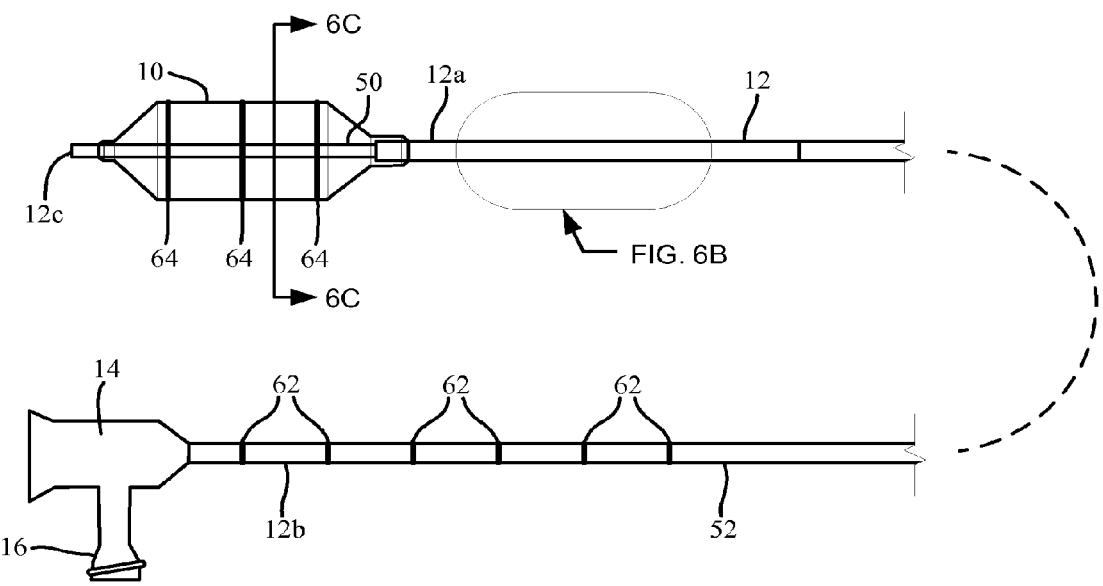
FIG. 6A illustrates an embodiment of a balloon dilation catheter according to one embodiment of the invention.
Figure 6B:
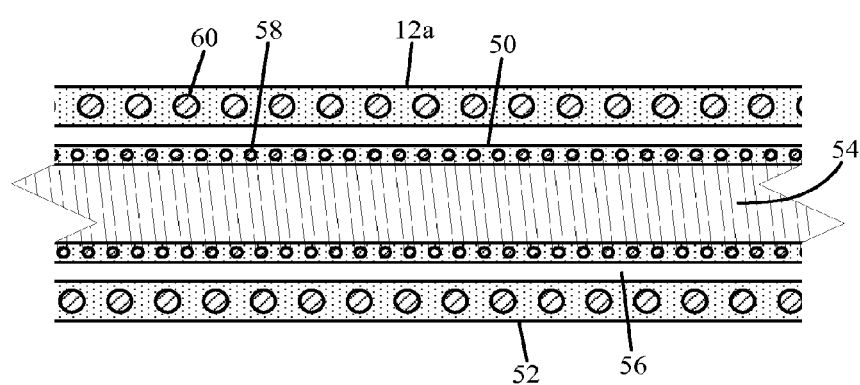
FIG. 6B is a longitudinal sectional view of a portion of the distal shaft of the embodiment of FIG. 6A.
Figure 6C:
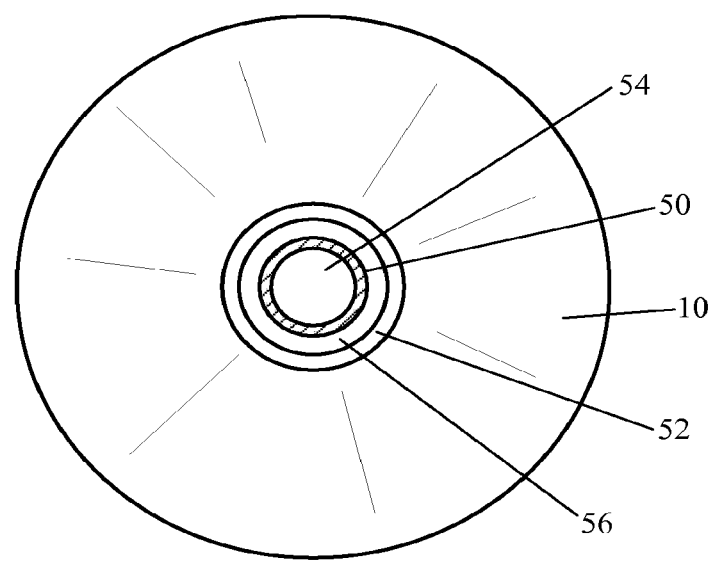
FIG. 6C is a cross-section of the distal shaft of the embodiment of FIG. 6A.

FIGS. 6A, 6B, and 6C show a preferred embodiment of a dilation balloon catheter 12 for dilation of a sinus ostium, particularly a maxillary sinus ostium MO. The balloon catheter 12 includes a balloon 10, distal shaft portion 12a, proximal shaft portion 12b, and a hub 14 with an inflation port 16 for inflation of the balloon 10. The balloon catheter 12 is formed using an inner tube 50 coaxially arranged within an outer tube 52 (described in more detail below). An inflation lumen 56 is formed between the inner tube 50 and the outer tube 52. The balloon catheter 12 terminates at a distal tip 12c that projects distally from the balloon 10. The balloon catheter 12 may be formed as an "over the wire" design (as shown in FIGS. 6A-6C), but it is contemplated that it could be a "fixed wire" design or a "monorail" design, as is known in the balloon catheter art, particularly the coronary angioplasty art. However, the length of the balloon catheter 12 shown is relatively short in comparison, preferably from about 10 to about 30 cm, and more preferably between about 15 and about 25 cm. The expanded diameter of the balloon 10 would depend on the initial and final desired size of the sinus ostium to be dilated. Preferred diameters would be from about 2 mm to about 10 mm, and most preferably from about 3 to about 7 mm. A preferred "set" of balloon catheters 12 would include a series of catheters having inflated balloon diameters of 2, 4, 6, and 8 mm. Alternatively, a series of catheters 12 having 3, 5, and, 7 mm expanded balloon diameters could be provided. The balloon 10 is preferably from about 5 mm to 40 mm in length (not including the conical portions), and more preferably from about 10 mm to about 20 mm in length.

With particular reference to FIG. 6B, the distal shaft portion 12a of the balloon catheter 12 is preferably of a coaxial construction, with an inner tube 50 located inside of an outer tube 52. The inner tube defines the wire guide lumen 54 for passage of the wire guide 24 (not shown in FIG. 6B). The annular space formed between the inner and outer tubes 50, 52 defines an inflation lumen 56. The inflation lumen 56 may hold a fluid which is used to inflate the balloon 10. In the embodiment of FIG. 6B, lumens 54, 56 are coaxially arranged. However it is contemplated that a single tube with two side-by-side lumens 54, 46 could be utilized as well.

Because of the anatomic challenge of accessing the maxillary sinus ostium MO, a preferred embodiment of the balloon catheter 12 includes a kink-resisting structure in the shaft, particularly in the distal shaft portion 12a, as this is the portion of the catheter 12 that may be exposed to a particularly tight bend as it is advanced around the uncinate process UP. The kink resisting structure is preferably a coil 58, 60 or braid (not shown) that is incorporated into the inner tube 50 and/or the outer tube 52. FIG. 6B illustrates coils 58, 60 incorporated in both the inner and outer tubes 50, 52, respectively. If a coil 58 is incorporated in the inner tube 50, it is preferably included in the entire distal portion 12a, including that portion that traverses the balloon 10. It is contemplated that for other constructions such as "fixed wire" or "rapid exchange" that the kink resisting structure could also be incorporated.

Inner and outer tubes 50, 52 are preferably formed of a suitable material such as polyethylene, PEBAX (Arkema), PTFE, NYLON (DuPont), HYTREL (DuPont), or a combination thereof. Proximal shaft portion 12b may be more rigid than distal portion 12b, and may further incorporate a metallic tube (not shown) for either the inner tube 50 or the outer tube 52 of the proximal shaft region.

To assist in positioning of the balloon catheter 12 to a target site, one or more shaft markers 62 may be provided at one or more locations along the shaft of the balloon catheter. Preferably, the markers 62 are positioned in uniform increments (e.g., 1 cm increments) along the full length of the shaft (proximal region 12b and distal region 12a). Additionally, one or more markers 64 on the balloon 10 may be provided. Both the shaft markers 62 and the balloon markers 64 are useful in positioning the balloon 10 relative to the wire guide 24 and/or guide catheter 18, together with prior or continuous optical visualization using a visualization tool such as an endoscope. Although not shown, the wire guide 24 could also include markers spaced at predefined increments. Balloon markers 64, shaft markers 62, and/or wire guide markers (not shown) could make use of a color-coding system or some other recognizable pattern to facilitate endoscopic imaging. For instance, a certain color of marker could pertain to a certain distance from a particular location, such as the tip of the wire guide 24 or the center of the dilation balloon 10. Alternatively, one or more radiopaque markers (not shown) could be provided on the shaft underneath the balloon 10 if fluoroscopic imaging is utilized.

Figure 7C:
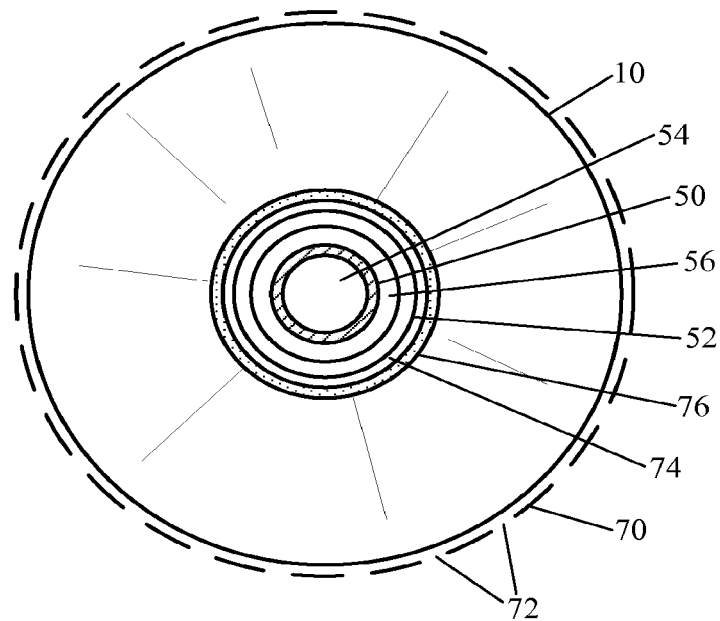
FIG. 7C is a cross-sectional view of the distal shaft of the embodiment of FIG. 7A.
Figure 7A:
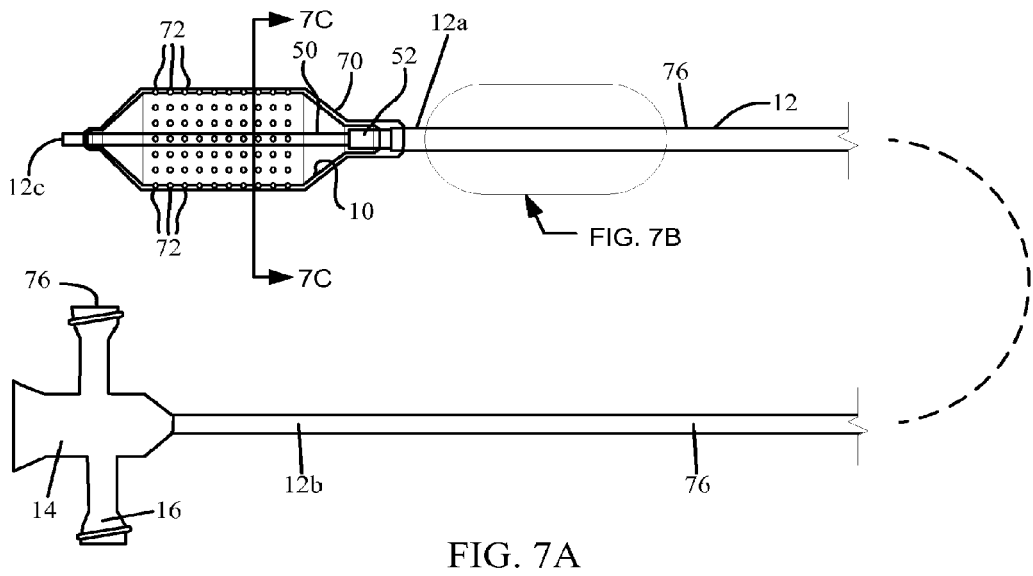
FIG. 7A illustrates an alternative embodiment of a balloon dilation catheter according to one embodiment.
Figure 7B:
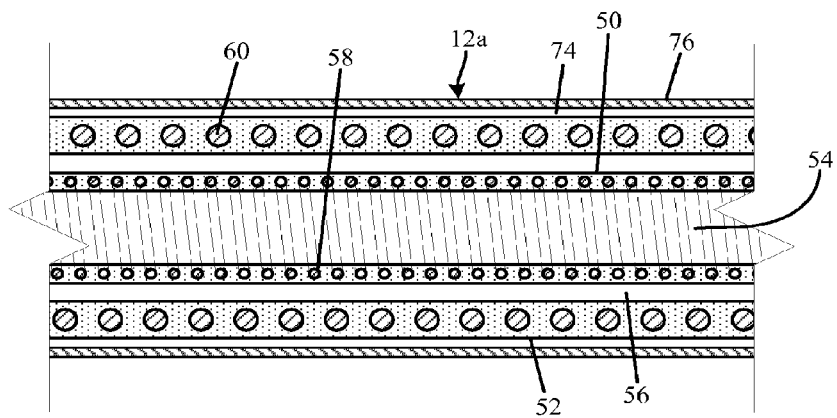
FIG. 7B is a longitudinal sectional view of a portion of the distal shaft of the embodiment of FIG. 7A.

FIGS. 7A, 7B, and 7C show an alternative embodiment for a sinus ostium dilation balloon catheter 12. In addition to the structures associated with the catheter shown in FIGS. 6A and 6B, this embodiment further incorporates structure to facilitate the infusion and delivery of one or more therapeutic and/or diagnostic agents at the site of the dilation balloon 10.

In a preferred embodiment, a portion of the balloon catheter 12 that extends proximally and distally with respect to the balloon 10 includes an outer membrane 70 with one or more perforations 72 in the membrane wall. The space between the balloon 10 and the membrane 70 is in fluid communication with an infusion lumen 74 (shown in FIG. 7B) formed in the shaft of the balloon catheter 12. The infusion lumen 74 could be formed by the addition of an infusion tube 76 located on the outside of the outer tube 52. An infusion port 76 located in the proximal hub 14 is in fluid communication with the infusion lumen 74.

The balloon catheter 12 illustrated in FIGS. 7A-7C may be particularly useful for the delivery of an adhesion preventing substance such as MeroGel (Medtronic/Xomed) or Sepragel® (Genzyme Biosurgical/Gyrus ENT) prior to, during, or following the dilation process. This would result in a coating or "sleeve" of the agent being disposed on the contacted tissue region. The fact that the coating or "sleeve" would have an open passageway would provide for immediate ventilation and drainage of the treated sinus.

Figure 8:
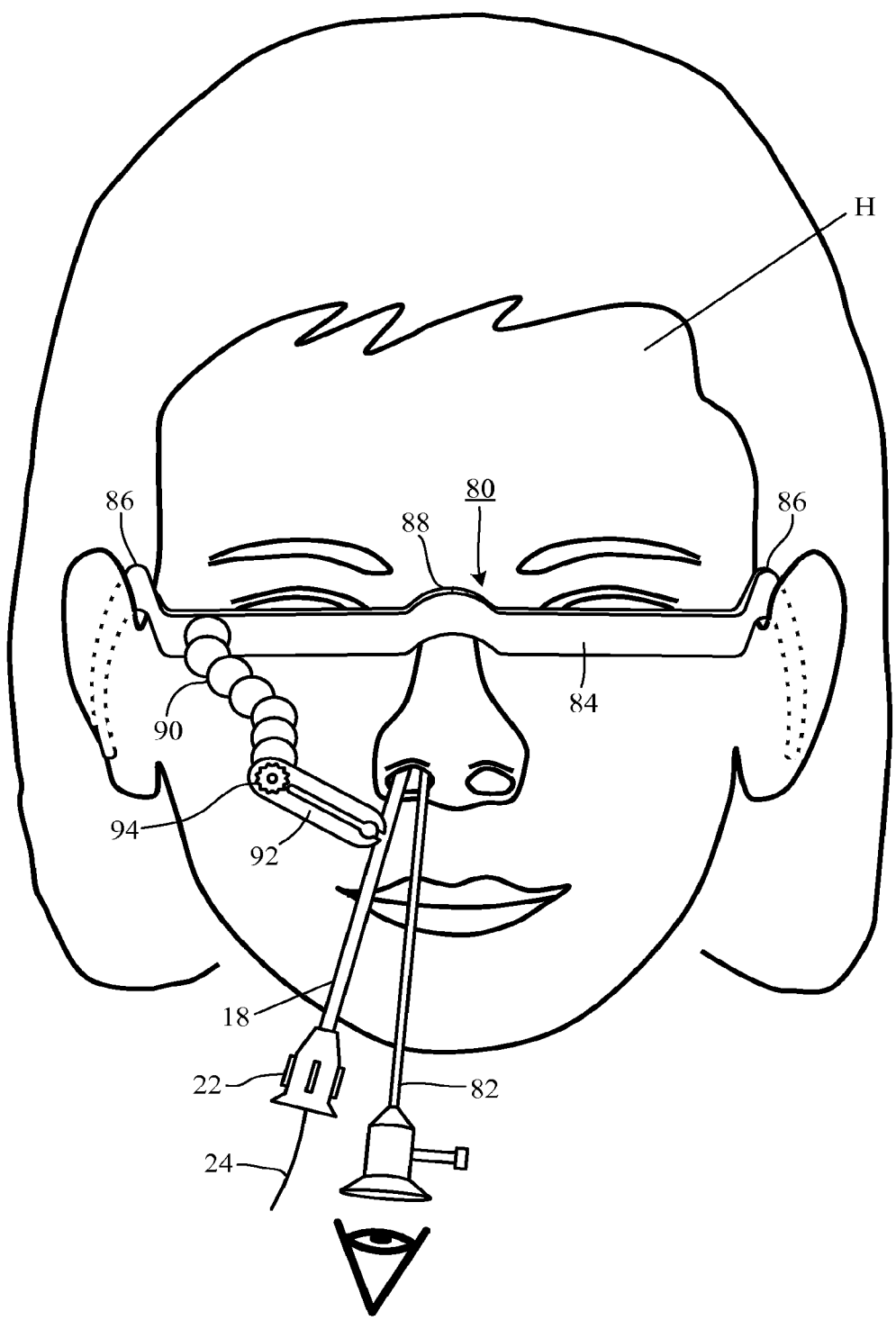
FIG. 8 illustrates an embodiment of a stabilization device according to one aspect of the invention.
Figure 9:
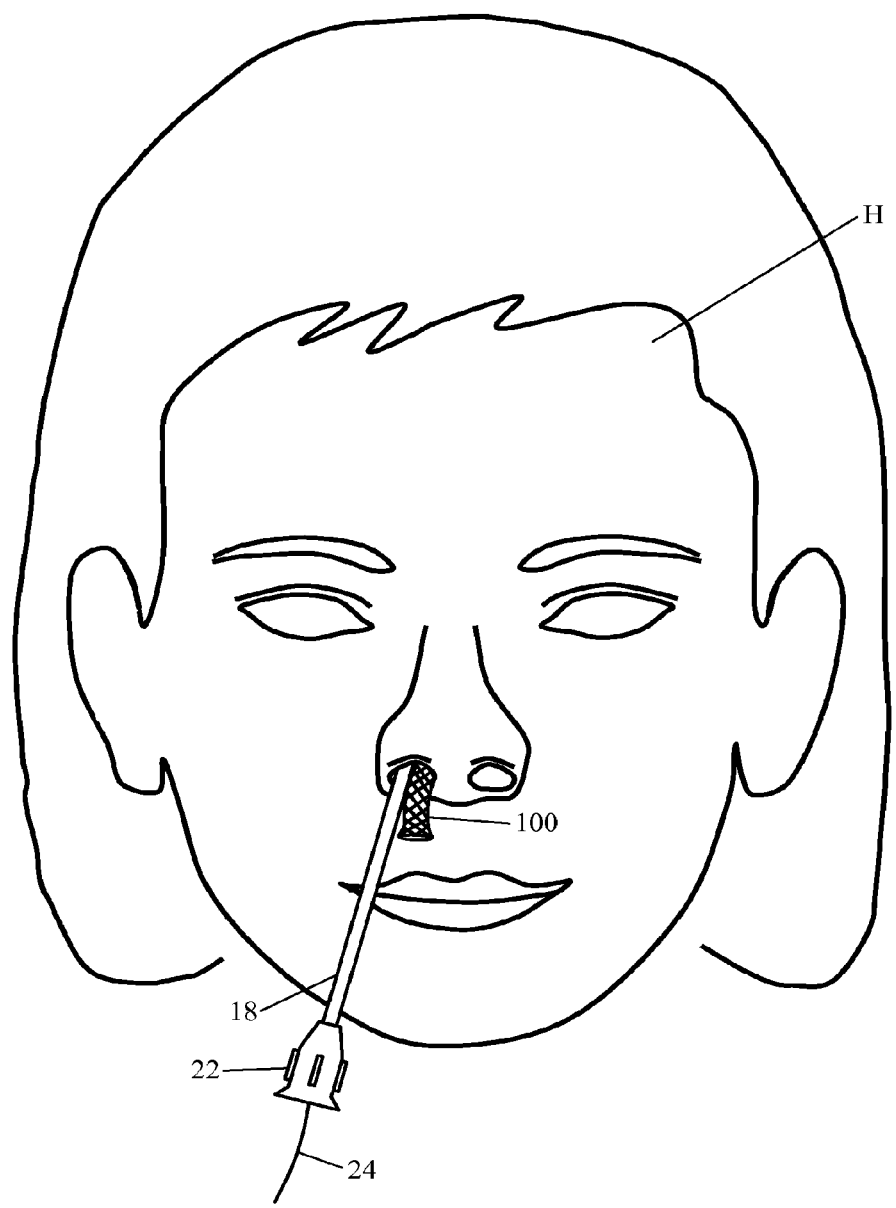
FIG. 9 illustrates an alternative embodiment of a stabilization device according to another aspect of the invention.

FIGS. 8, 9, and 10 shows various embodiments of a stabilizing device 80 for use with the device and methods disclosed herein. The stabilizing device 80 is used to assist in holding and stabilizing one or more of the various tools used in the treatment of a sinus ostium. Since at times many devices may be in use, it may be difficult for the physician to manage all such devices. Use of a stabilizing device can free the hands to manage fewer devices at any given time. For example, the stabilizing device 80 may be used to stabilize a guide catheter 18 (as shown in FIG. 8), a balloon catheter 12, and/or an endoscope 82.

The embodiment shown in FIG. 8 utilizes a base member 84 which secures to various portions of the head H, such as the ears and/or top of the nose. Preferably, two ear hooks 86 wrap around the ear in a similar way as eyeglasses. The base member 84 also rests on the nose with a nose bridge 88. A support arm 90 is secured to the base member 84. In one aspect of the invention, the support arm 90, can preferably be manipulated or formed into any desired shape. For example, the support arm 90 may be formed from a flexible material. A securing member 92 such as a clamp is located on the free end of the support arm 90. The securing member 92 may be removable and/or interchangeable via a tightening member. Support arm 90 and securing member 92 are held fast by a tightening member 94 such as a tightening nut. In this figure, a clamp 92 is shown stabilizing a guide catheter 18, which allows the physician to use his or her hands on the endoscope 82 and the wire guide 24, while the position of the guide catheter 18 is maintained. This may be helpful while the physician tries to advance the wire guide 24 into the desired sinus. It is contemplated that more than one securing member 92 and/or more than one support arm 90 could be mounted to the base member 84 to stabilize more than one device.

The embodiment illustrated in FIG. 9, a stabilizing element 100 stabilizes a device against an interior surface of the nostril. As shown in FIG. 9, the stabilizing element is stabilizing a guide catheter 18. In one preferred embodiment, the stabilizing element 100 is formed as an expandable tubular structure, such as a self-expanding tubular braid. In the expanded state, the tubular structure includes a lumen or passageway through which one or more devices may be placed. The expandable tube 100 is positioned in the nostril next to the device(s) to be stabilized. Friction holds the device(s) in place, while maintaining a passageway for additional devices such as an endoscope (not shown in FIG. 9) to be introduced into the nasal cavity. More than one expandable tube 100 could be used, either next to another, or in a nesting relationship.

Figure 10A:
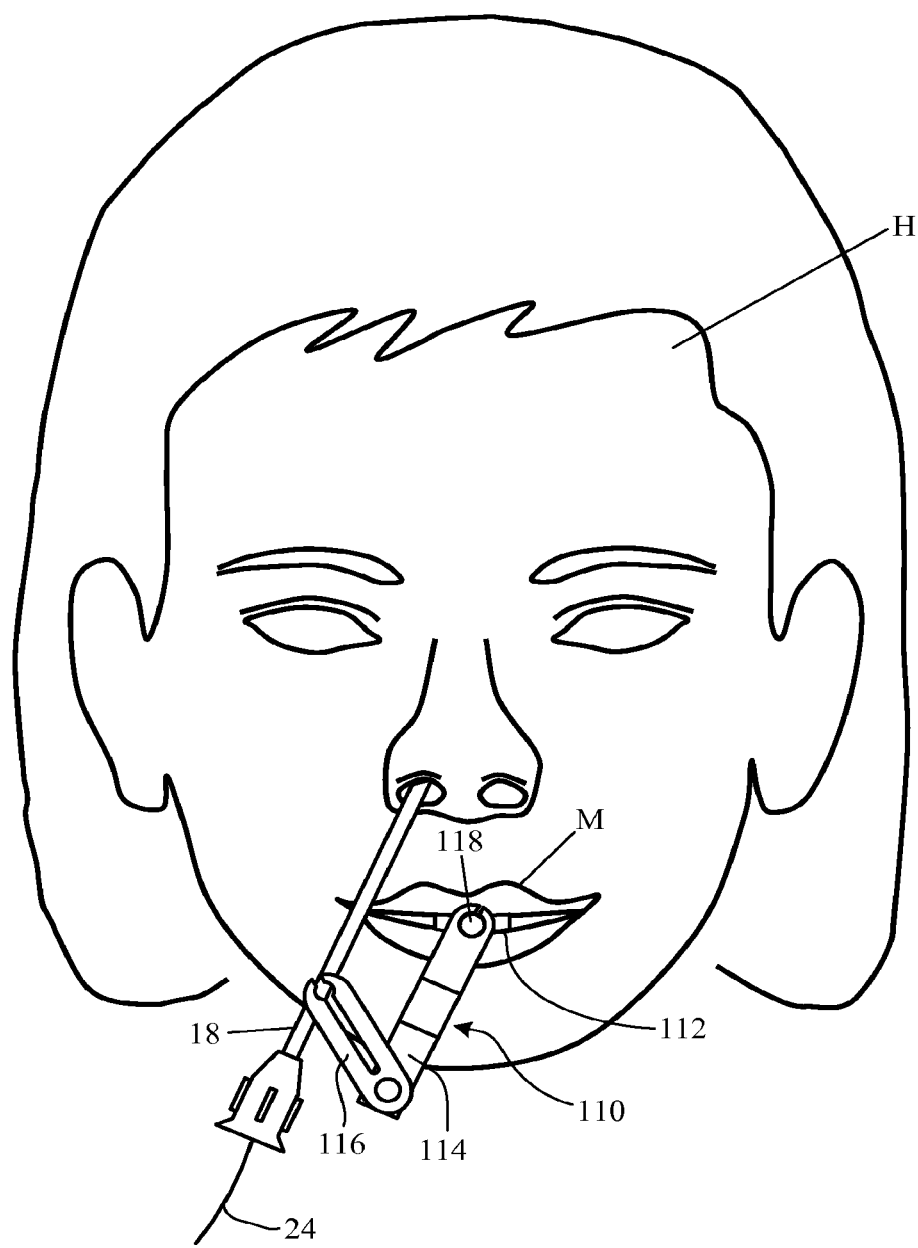
FIG. 10A illustrates a further alternative embodiment of a stabilization device according to another aspect of the invention.
Figure 10B:
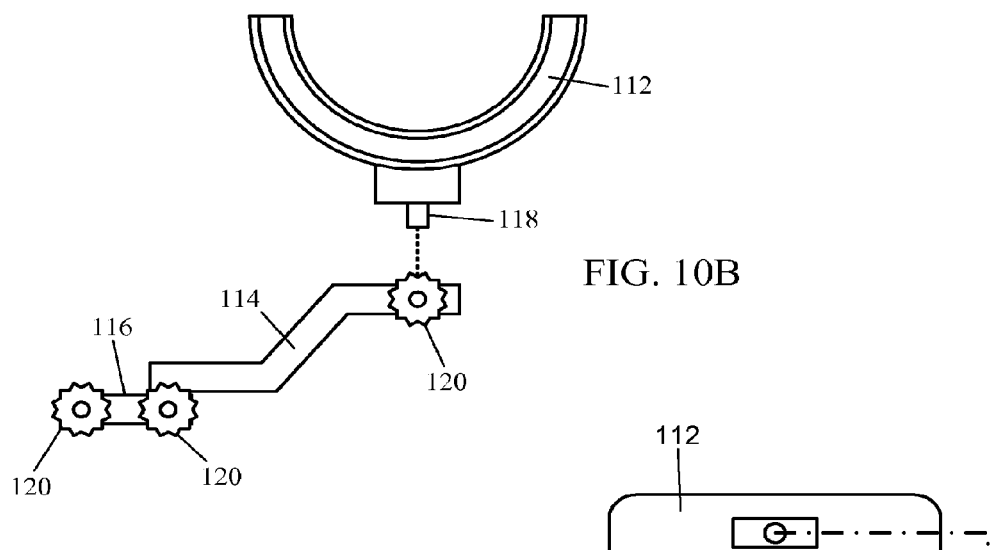
FIG. 10B is a partially exploded top view of the stabilization device of FIG. 10A.
Figure 10C:
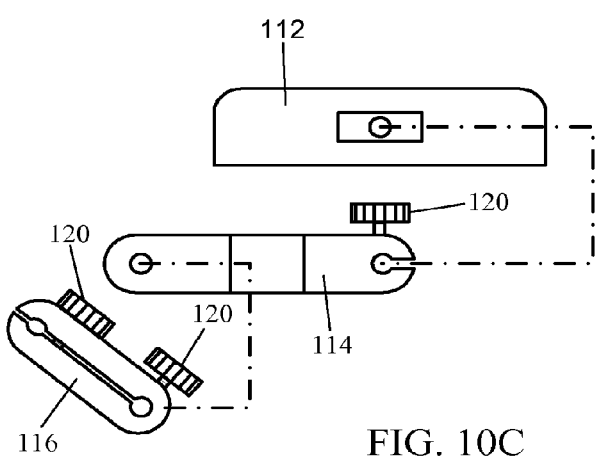
FIG. 10C is a partially exploded front view of the stabilization device of FIG. 10A.

With reference now to FIGS. 10A, 10B, 100, and 10D, a stabilizing device 110 makes use of the patient's mouth M. A mouth piece 112 is connected coupled to a support arm 114, which is connected to a securing member 116 such as a clamp to stabilize the position of a device such as a guide catheter 18. The support arm 114 and clamp 116 can be positioned, e.g. by rotating around pivot points, to bring the clamp 116 to any desired position. FIG. 10B shows a top view of the stabilizing device 110 in a partially exploded view. The mouth piece 112 is configured to engage the upper and/or lower jaw of the patient. The support arm 114 is connected to the mouth piece 112, preferably by a lockable pivot point 118. The clamp 116 is likewise connected to the support arm 114. A series of securing members 120 such as locking screws or nuts locks the clamp 116 position relative to the mouth M.

Figure 10D:
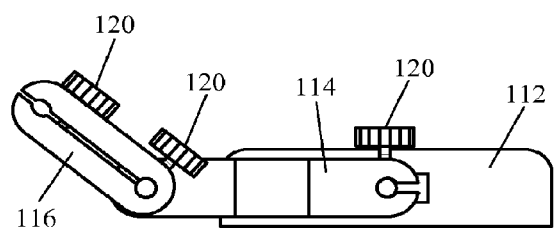
FIG. 10D is an assembled front view of the stabilization device of FIG. 10A.

FIG. 100 is a partially exploded frontal view of the stabilizing device 110 of FIG. 10B. FIG. 10D shows the stabilizing 110 device in the fully assembled state. Again, one or more support arms and/or one or more clamps 116 could be used to stabilize multiple devices such as guide catheters 18, wire guides 24, endoscopes 82, or other instruments used by the physician.

Figures 11A, 11B:
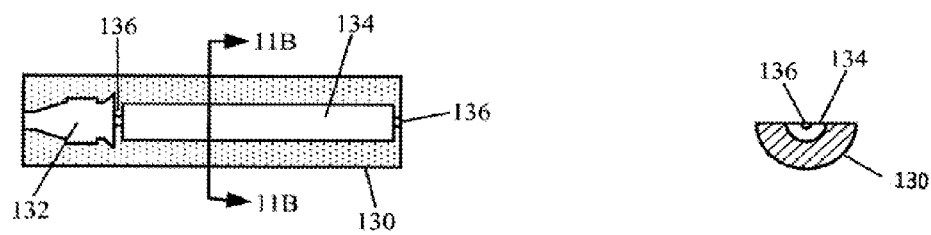
FIG. 11A illustrates an embodiment of a wire movement guide according to one aspect of the invention.
FIG. 11B is a cross-sectional view of the wire movement guide of FIG. 11A.
Figure 11C:
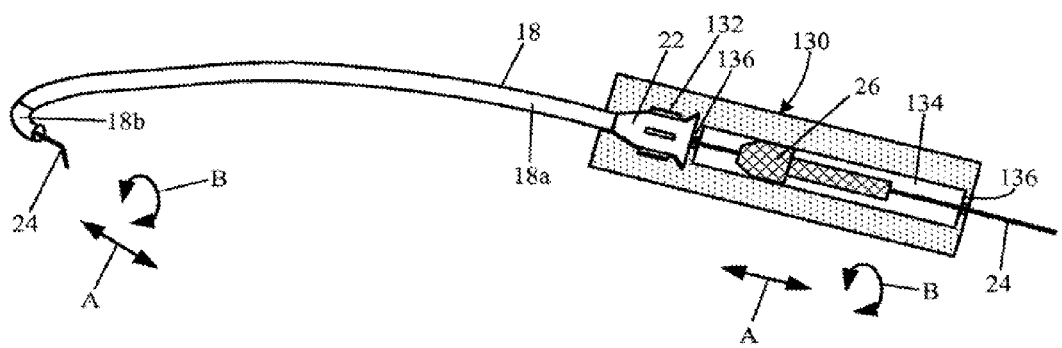
FIG. 11C is an assembly drawing of the wire movement guide of FIG. 11A attached to a guide catheter.

FIGS. 11A, 11B, and 11C illustrate a wire movement guide 130 that is used to facilitate one-handed movement of both the wire guide 24 and guide catheter 18. The wire movement guide 130 may be formed as a recessed handle or the like. As seen in FIG. 11C, during operation of the guide catheter 18, a steering device 26 is secured to the wire guide 24. The steering device 26 is able to slide axially and rotate in the movement path (as shown by arrows A and B in FIG. 11C). In a preferred embodiment, the recessed handle 130 includes a hub recess 132 that is sized to receive the hub 22 of the guide catheter 18. For example, the hub recess 132 may be sized to frictionally secure the hub 22 within the same. Alternatively, one or more detents, tabs, or the like may be positioned on the hub recess 132 and/or hub 22 to releasably secure wire movement guide to the hub 22 of the guide catheter 18. The wire movement guide 130 also includes a recess 134 for receiving the steering device 26. The recess 134 is dimensioned to permit axial and rotational movement of the steering device 26 as is shown in FIG. 11C. The wire movement guide 130 may also include a wire recess 136 for receiving the wire guide 24. The wire recess 136 may be interposed between the two recesses 132, 134. In addition, a wire recess 136 may be located at a proximal end of the wire movement guide 130 to permit the wire guide 24 to exit the proximal end of the wire movement guide 130. FIG. 11B illustrates a cross-sectional view of the wire movement guide 130.

In an alternative aspect of the invention, the wire movement guide 130 could be formed integrally with the hub 22 or simply formed integrally on the proximal end of the guide catheter 18.

Figure 11D:
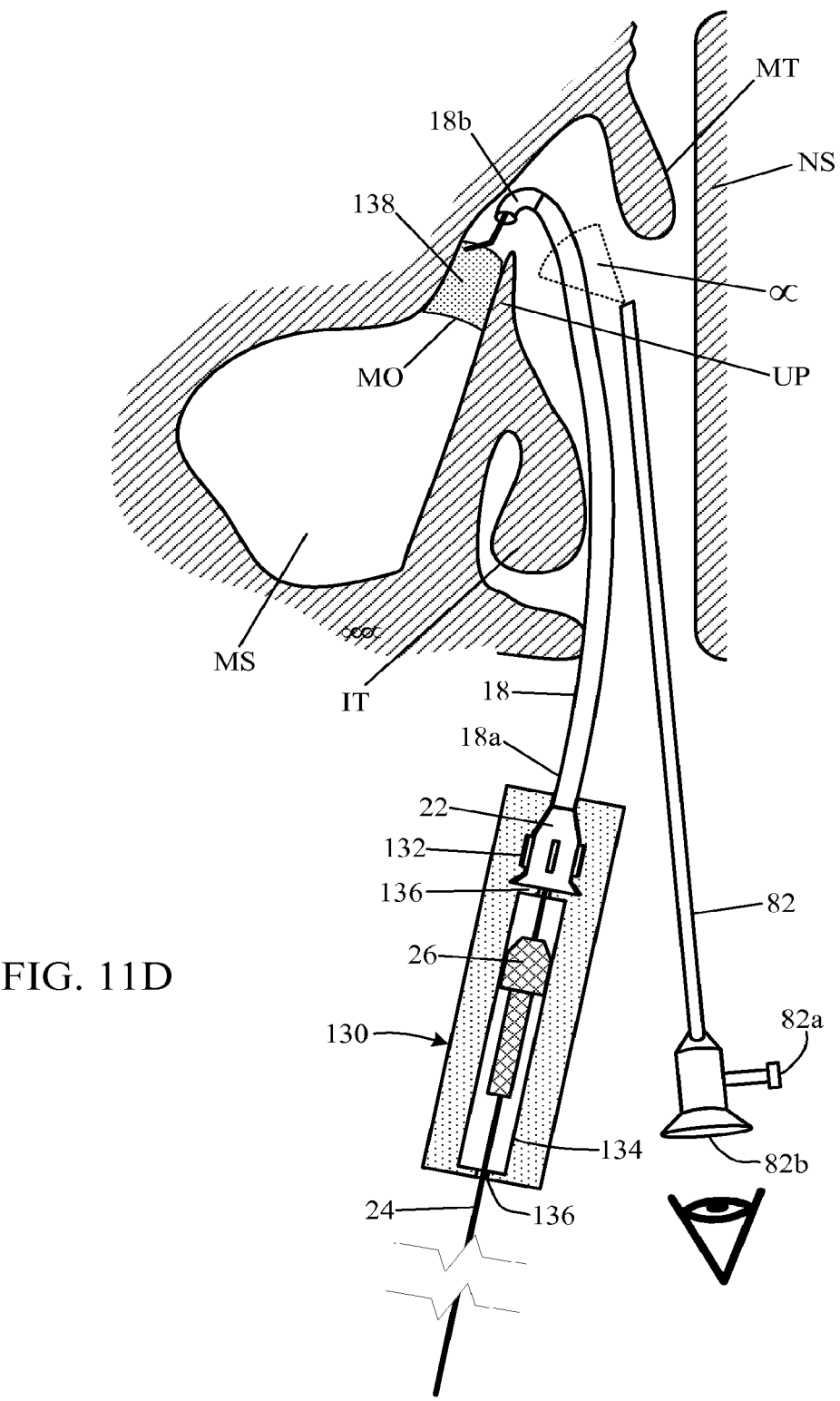
FIG. 11D illustrates a method for placement of a wire guide in a sinus ostium according to one aspect of the invention.

With the use of a wire movement guide 130, the physician can move the guide catheter 18 into a desired position (preferably with the use of endoscopic imaging, as depicted in FIG. 11D), while simultaneously advancing and/or rotating the wire guide 24 with a single hand. For example, the fingers could be manipulating the wire movement guide 130 and therefore the guide catheter 18, while the thumb is able to manipulate the wire guide 24 to a desired position in the nasal cavity or sinus. A portion of the exterior surface of the steering device 26 may be scored, roughened, or otherwise textured to aid the physician in manipulating the steering device 26. The wire movement guide 130 advantageously permits the physician to use his or her other hand to independently manipulate another tool such as, for example, an endoscope 82.

One preferred embodiment for positioning a wire guide 24 into the maxillary sinus ostium MO is depicted in FIG. 11D. In this embodiment, the guide catheter 18, wire movement guide 130, and wire guide 24 are manipulated under endoscopic visualization. Here, the endoscope 82 is a "rigid" endoscope, a standard tool in nasal surgery. The rigid endoscope generally has a forward looking viewing field a which may or may not be offset, a light port 82a, and a viewing port 82b through which an image is obtained (indicated with an eyeball symbol). The endoscope 82 is used to help identify the uncinate process UP, and the guide catheter 18 is "hooked" around the uncinate process UP. Additional tools such as a sinus "seeker" (not shown) can be utilized to help pull the uncinate process UP away from the opposite wall and make room for the tip 18b of the guide catheter 18. Once the guide catheter tip 18b is positioned, the wire guide 24 is manipulated by tactile feedback until it is felt to have passed into the maxillary sinus ostium MO and into the maxillary sinus MS. FIG. 11D illustrates a simplified obstruction 138 located adjacent the uncinate process UP and maxillary sinus ostium MO. This obstruction 138 may include mucous, inflamed mucosa, scar tissue, abnormal bony structure, or other substances. In this manner, only conventional endoscopic imaging is utilized—without the need for fluoroscopic imaging and/or other specialized "image guidance" technology. This same technique could be utilized for the other sinuses and their ostia as well. In addition, one or more of the stabilization devices 80, 100, 110 previously described could be utilized as would be useful in this or any of the subsequently described methods.

Figure 12:
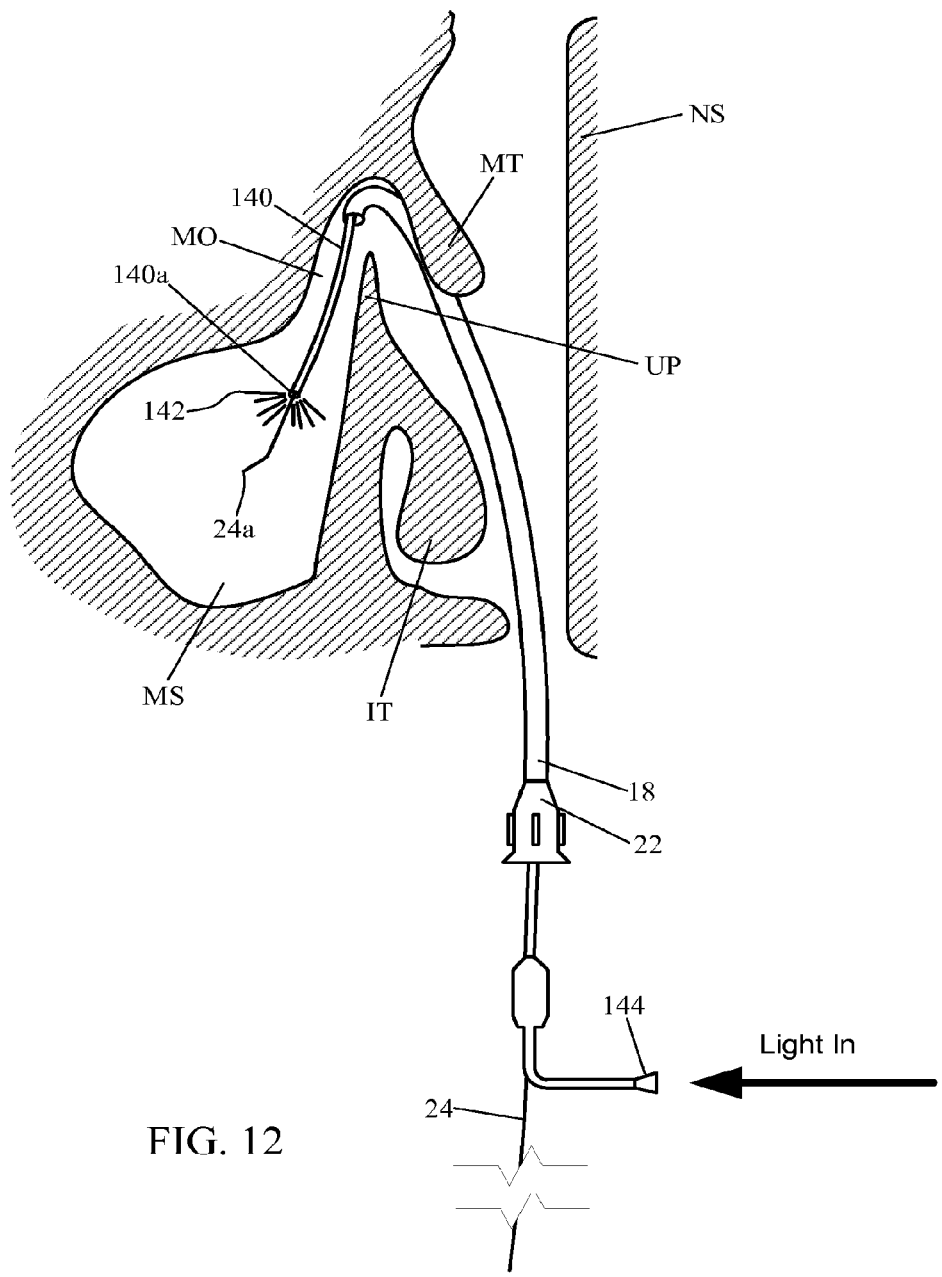
FIG. 12 illustrates a method and device for confirming the placement of a wire guide in a sinus according to one aspect of the invention.

During operation of the device, it may be desirable to have a way to independently confirm that the distal tip 24a of the wire guide 24 has been positioned in the desired sinus, and not inadvertently passed through some other structure, such as the orbital wall. Since the sinuses are difficult if not impossible to image with the standard rigid endoscopes, endoscopic imaging is not readily amenable for this confirmation. One such confirmation approach is illustrated in FIG. 12. As seen in FIG. 12, after the wire guide 24 has been positioned in what is believed to be the desired location (maxillary sinus MS), a fiber optic catheter 140 is positioned over the wire guide 24 and advanced distally towards the tip of the wire guide 24. The fiber optic catheter 140 may be positioned using a guide catheter 18 of the type illustrated in FIG. 12. The distal tip 140a of the fiber optic catheter 140 emits light 142 that is input into the fiber optic catheter 140 via a light port 144. In one aspect of the invention, the emitted light 142 is bright enough such that it lights up or illuminates the sinus cavity and can be visualized externally. In this regard, the surrounding environment (e.g., physicians office) may need to have the level of ambient light reduced or turned off completely to aid in the visualization process.

If a structure other than the desired sinus is illuminated, the physician or other operator knows that the wire guide 24 has been improperly positioned and can subsequently be repositioned into the proper location. Once the position of the wire guide 24 has been confirmed to be in the desired position, a balloon catheter 12 can then be confidently placed into the sinus ostium (e.g., MO) and dilated.

Figure 13:
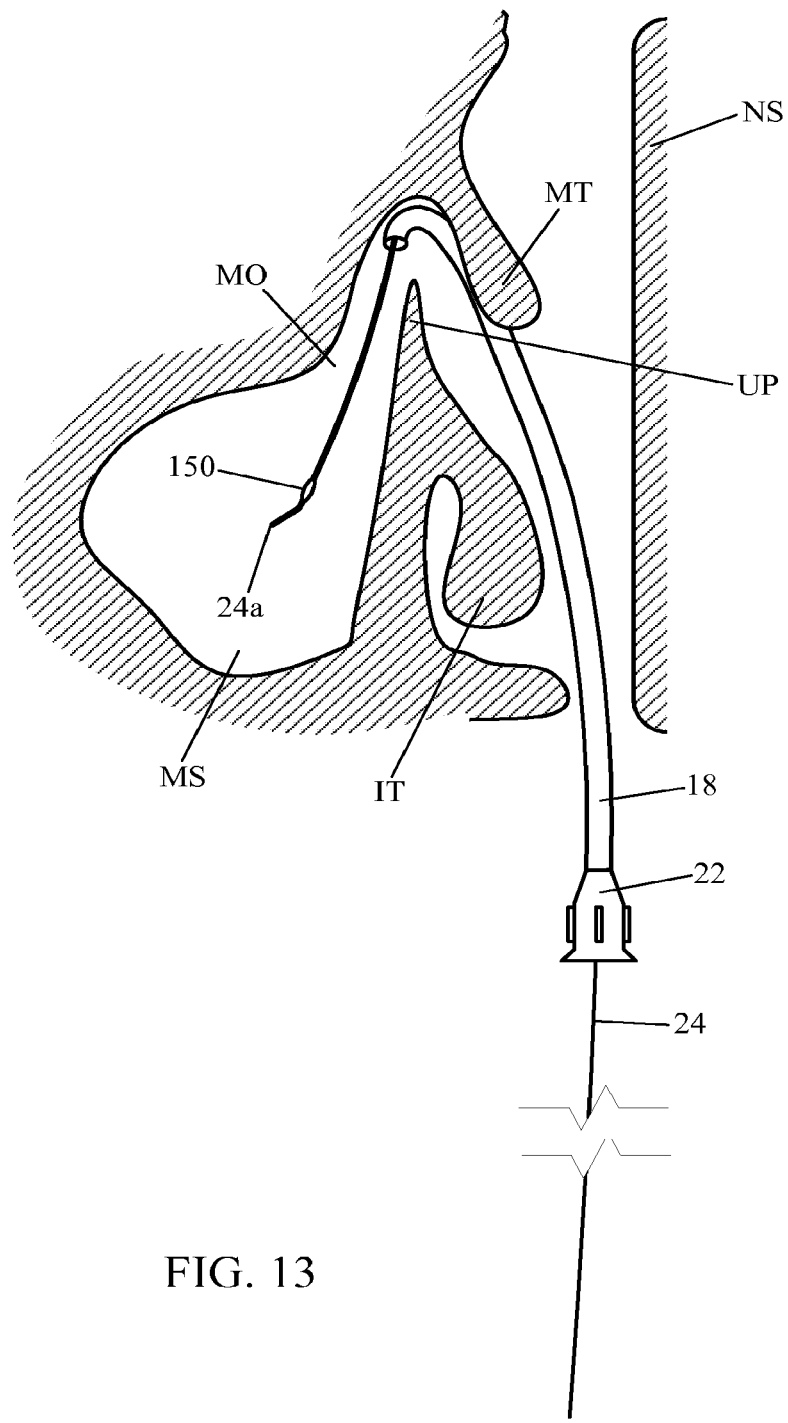
FIG. 13 illustrates an alternative method and device for confirming the placement of a wire guide, according to another aspect of the invention.

FIG. 13 illustrates an alternative embodiment for confirming the position of a wire guide 24. In this embodiment, the wire guide 24 is fitted with a detection element 150 at or near the distal tip 24a. In one aspect, the detection element 150 can be made of a magnetic material. A magnetic detection device (not shown) which could be as simple as a floating magnetic needle such as a compass needle may then be positioned outside the patient's face near the sinus to confirm the position of the wire tip 24a. For example, in this case, the deflection of the magnetic needle would indicate the presence of the detection element 150 (and thus the distal tip 24a of the wire guide 24) within the desired sinus cavity.

Alternatively, the detection element 150 could be formed from a dense metallic material that can be detected with a metal detector device (not shown). For example, the metal detector device may include a probe or the like that can be manipulated near to patient's face near the sinus cavity of interest to detect the presence (or absence) of the metallic detection element 150. In yet another aspect, the detection element 150 may emit a signal (e.g., radiofrequency pulse or the like) that can then be detected externally to confirm the presence or absence of the distal tip 24a of the wire guide 24 within the sinus cavity of interest.

Figure 14:
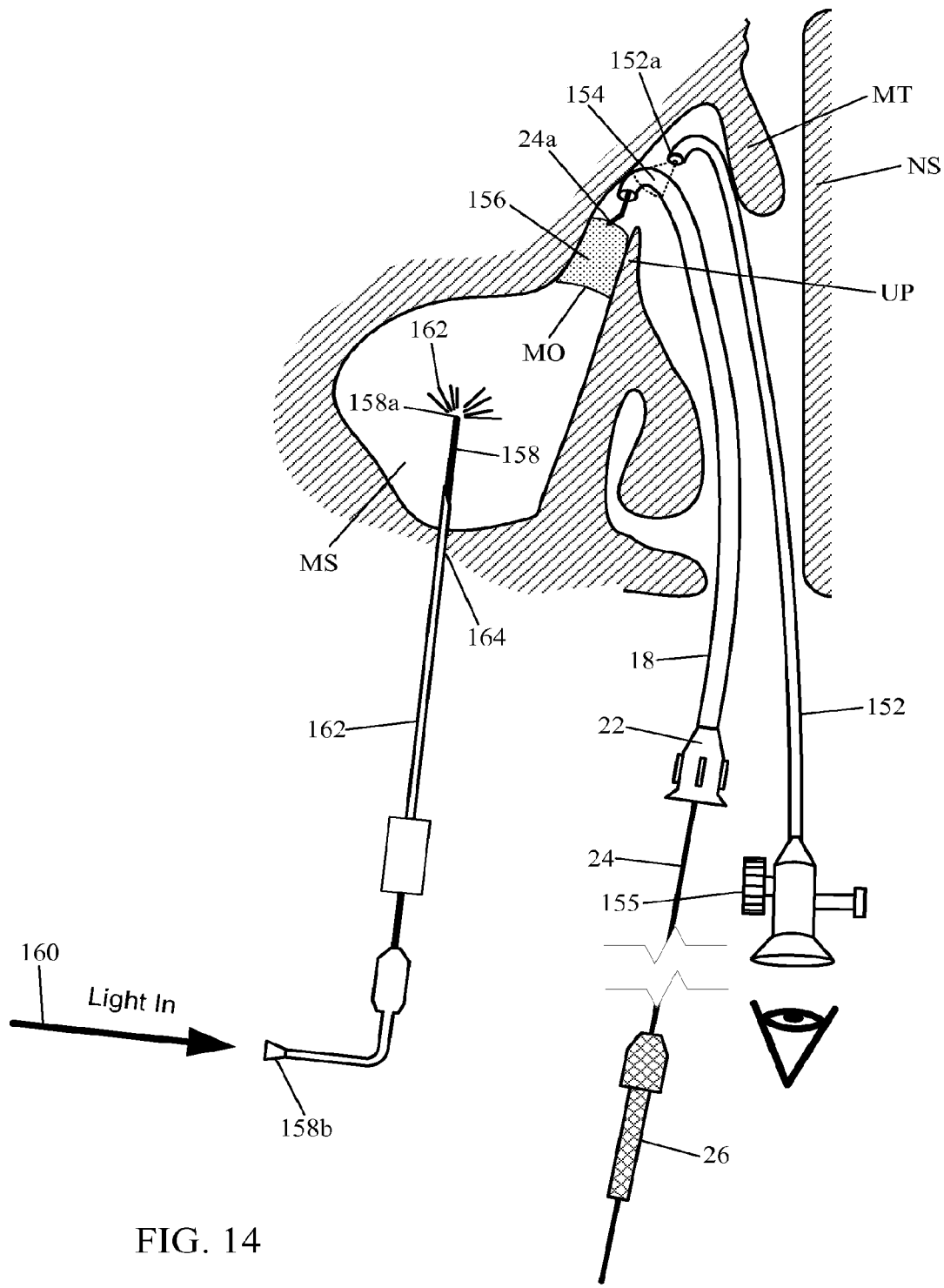
FIG. 14 illustrates methods and devices for accessing a sinus according to one aspect of the invention.

Independent confirmation methods and devices as described above may not be necessary if more versatile optical imaging techniques and devices are utilized in the placement of the various devices such as wire guides 24, guide catheters 18, and/or balloon catheters 12. For instance, FIG. 14 illustrates a method for placing a wire guide 24 across a sinus ostium (e.g., maxillary ostium MO) with the aid of a directable or steerable endoscope 152. Directable endoscopes 152 make use of flexible fiber optic bundles which can be bent or curved to alter the direction of the viewing field 154. A typical construction of a directable endoscope 152 includes multiple control wires (not shown) connected near the distal tip 152a and to a deflection knob 155. In this method, the directable endoscope 152 is positioned superior to the uncinate process UP and then directed retrograde to allow direct viewing of the viewing field 154 where the guide catheter 18 and wire guide 24 are being manipulated. To further aid in the identification of the maxillary sinus ostium MO, particularly in the case of occlusion 156 associated with sinusitis, the maxillary sinus MO is illuminated with the placement of a small illumination member 158 into the sinus. The illumination member 158 may be formed as an elongate member having a light-emitting distal end 158a and a proximal end 158b that is typically connected or otherwise coupled to a light source 160. In one aspect, the illumination member 158 is formed as a fiber optic light based device.

The illumination member 158 can be placed into the sinus cavity of interest (e.g., maxillary sinus MS) by using a piercing member 162 such as, for example, an introducer needle 162 that is introduced through the canine fossa CF region. It should be understood that reference to the canine fossa CF refers to the general region or anatomical area surrounding or adjacent to the canine fossa CF and is not limited to a single, discrete structure or location. The introducer needle 162 may include a hollow lumen or the like to permit the passage of the illumination member 158. The canine fossa CF is a thin portion of the maxillary sinus wall located adjacent the root of the canine teeth. The canine fossa CF has been utilized for other intrasinus procedures. After the formation of a passageway 164 through the canine fossa CF, the illumination member 158 is advanced distally such that the distal tip 158a of the illumination member 158 is disposed inside the sinus cavity. The emitted light 162 in the maxillary sinus MS (or other sinus cavity) will be visible through the blockage 156 of the ostium MO using the directable endoscope 152. This aids the physician or other user to direct the wire guide 24.

Figure 15:
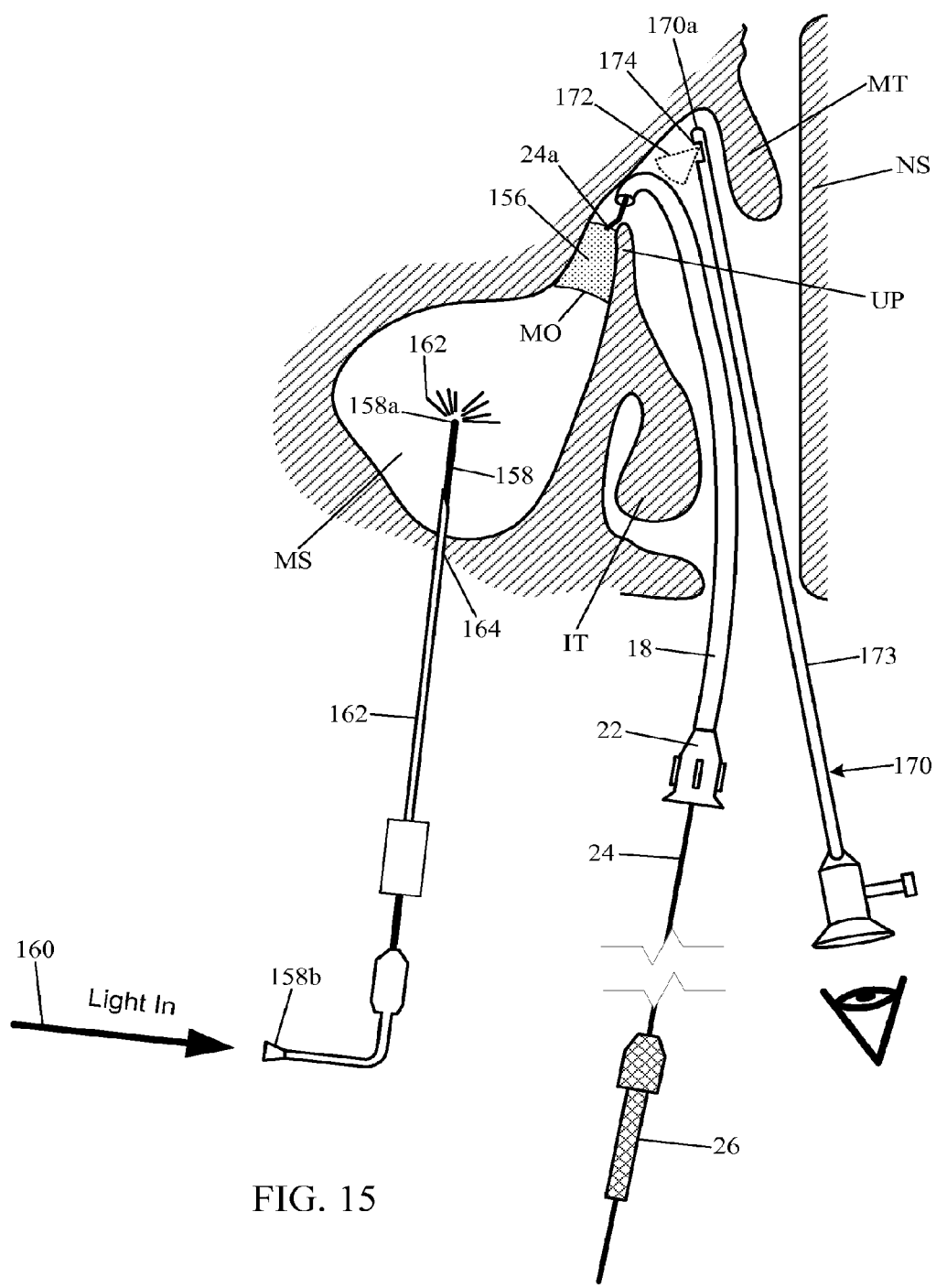
FIG. 15 shows additional methods and devices for accessing a sinus, according to another aspect of the invention.

FIG. 15 illustrates a similar method to FIG. 14, the difference being the use of a rigid retrograde endoscope 170. A rigid retrograde endoscope 170 is similar to a normal rigid endoscope, but the direction of viewing field 172 is in a retrograde direction. The rigid retrograde endoscope 170 has a substantially rigid shaft portion 173 and a retrograde viewing window 174 located at or near the distal tip 170a. Retrograde visualization is accomplished through the use of one or more mirrors and/or lenses located at or adjacent to the viewing window 174 to deflect the viewing field 172. Since the viewing field 172 is retrograde, this endoscope 170 can assist in accessing the sinus ostium in a similar manner as described with respect to the method shown in FIG. 14. One difficulty with a rigid retrograde endoscope 170 is that it can be awkward to initially position it, since it cannot be used to see straight ahead. However, this difficulty is overcome by utilizing a normal rigid endoscope (not shown) alongside the retrograde rigid endoscope 170 to get it positioned initially in the nasal cavity. Again, an illumination member 158 in the sinus, placed via the canine fossa CF, can be further utilized to aid in accessing the sinus ostium.

Figure 16A:
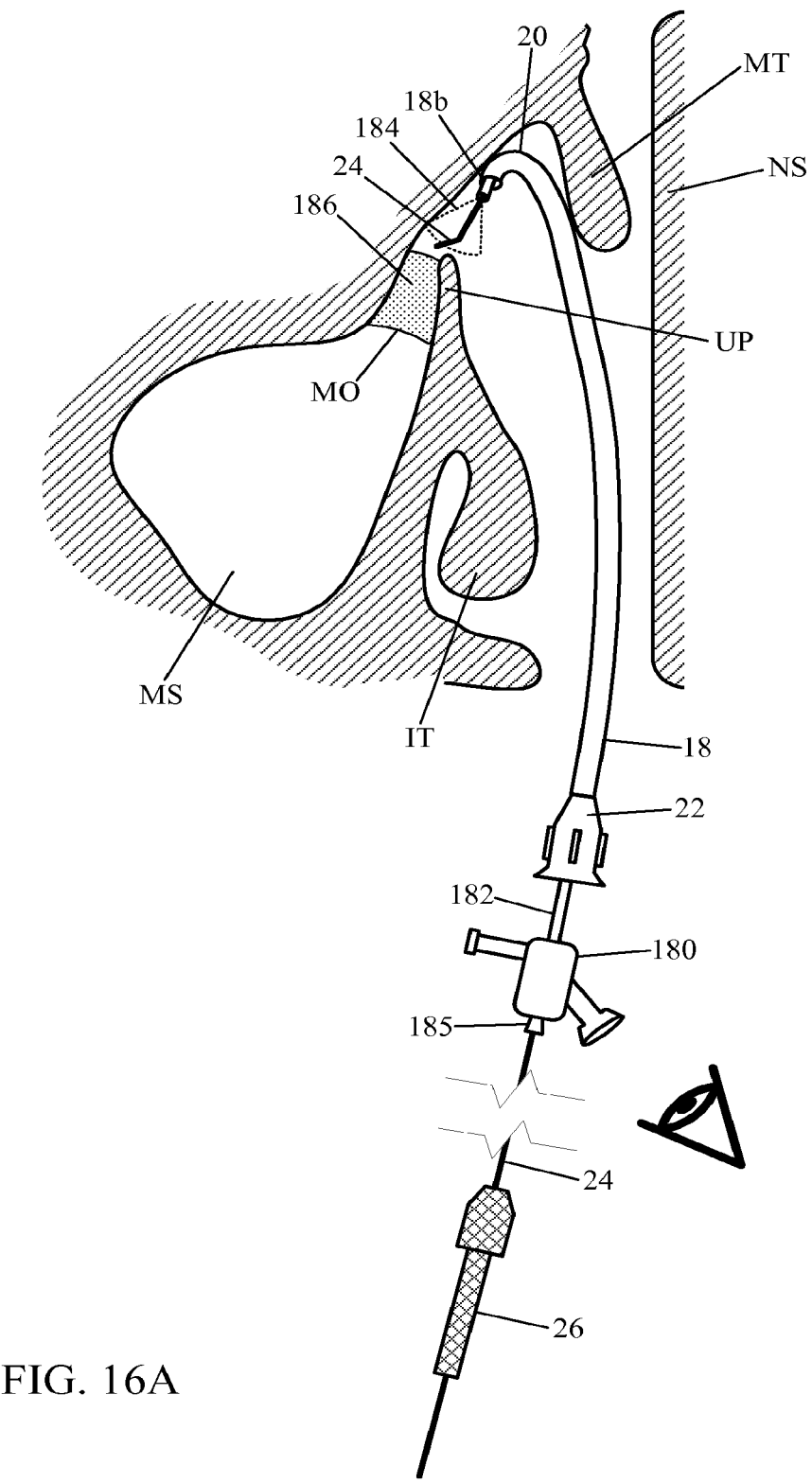
FIG. 16A shows additional methods and devices for accessing a sinus according to another aspect of the invention.
Figure 16B:
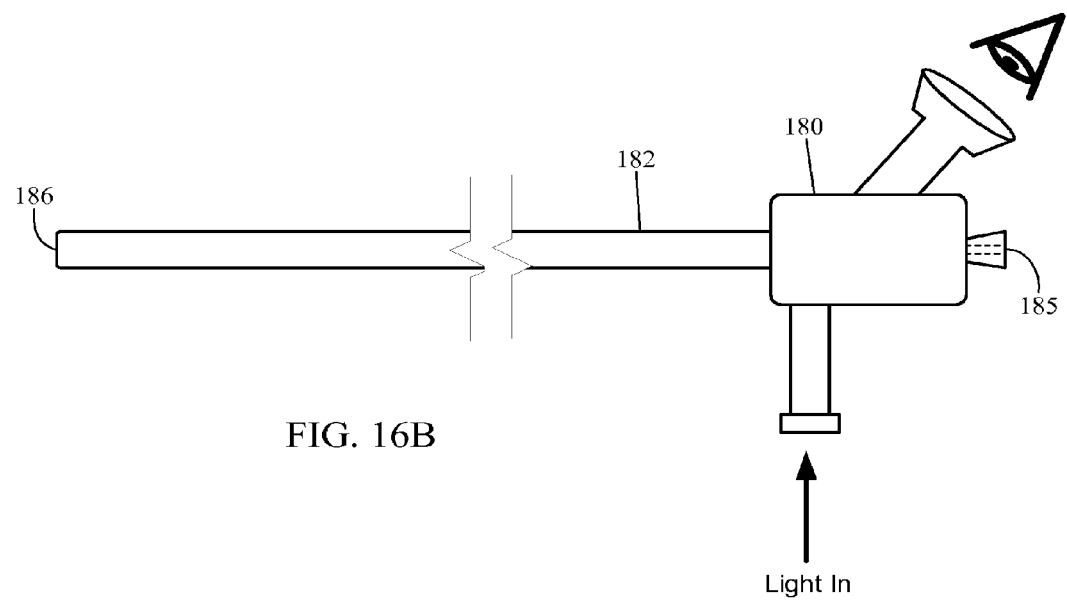
FIG. 16B shows a flexible visualization scope as used in connection with FIG. 16A.
Figure 16C:
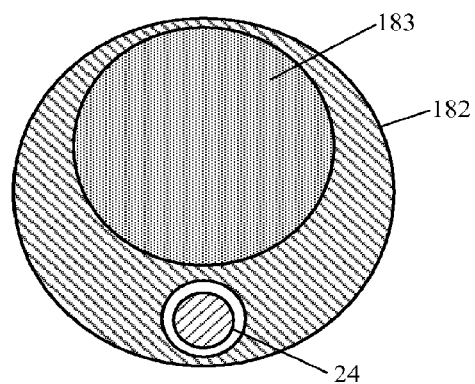
FIG. 16C is a cross-sectional view of the flexible visualization scope of FIG. 16B.

Still other alternative methods for accessing the sinus ostium are illustrated in FIGS. 16A, 16B, and 16C. In these embodiments, a flexible visualization scope 180 is utilized. The flexible visualization scope 180 includes an elongate flexible body 182 that contains a flexible fiber optic bundle 183 (as shown in FIG. 16C) for viewing around bends. Although not shown in the figures, the fiber optic bundle 183 includes both "imaging" fibers and "illumination" fibers for lighting up the viewing field 184. The flexible visualization scope 180 is not directable like the endoscope 152 of FIG. 14. Rather, the flexible visualization scope 180 includes a lumen or passageway 185 for the wire guide 24 and follows the wire guide 24 around bends as illustrated in FIG. 16A. Consequently, in this method, particularly for a maxillary sinus ostium MO, a guide catheter 18 having a curved distal portion 20 is positioned near or around the uncinate process UP. A conventional rigid endoscope (not shown) may be used to assist in this positioning. Next, the wire guide 24 is positioned near the tip 18b of the guide catheter 18. Then the flexible visualization scope 180 is advanced over the wire guide 24, curving back in a retrograde fashion, allowing the viewing field 184 to be directed towards the sinus ostium (MO in this case). A blockage is shown 186 positioned within the maxillary ostium MO. The wire guide 24 and guide catheter 18 may then be manipulated under visual observation to access the ostium MO. Again, as has been mentioned previously, additional tools or the use of a "seeker" can be used in addition to the visualization scope 180, guide catheter 18 and wire guide 24. In addition, the sinus cavity of interest may be illuminated using the canine fossa CF access method described above with respect to FIGS. 14 and 15.

Figure 17A:
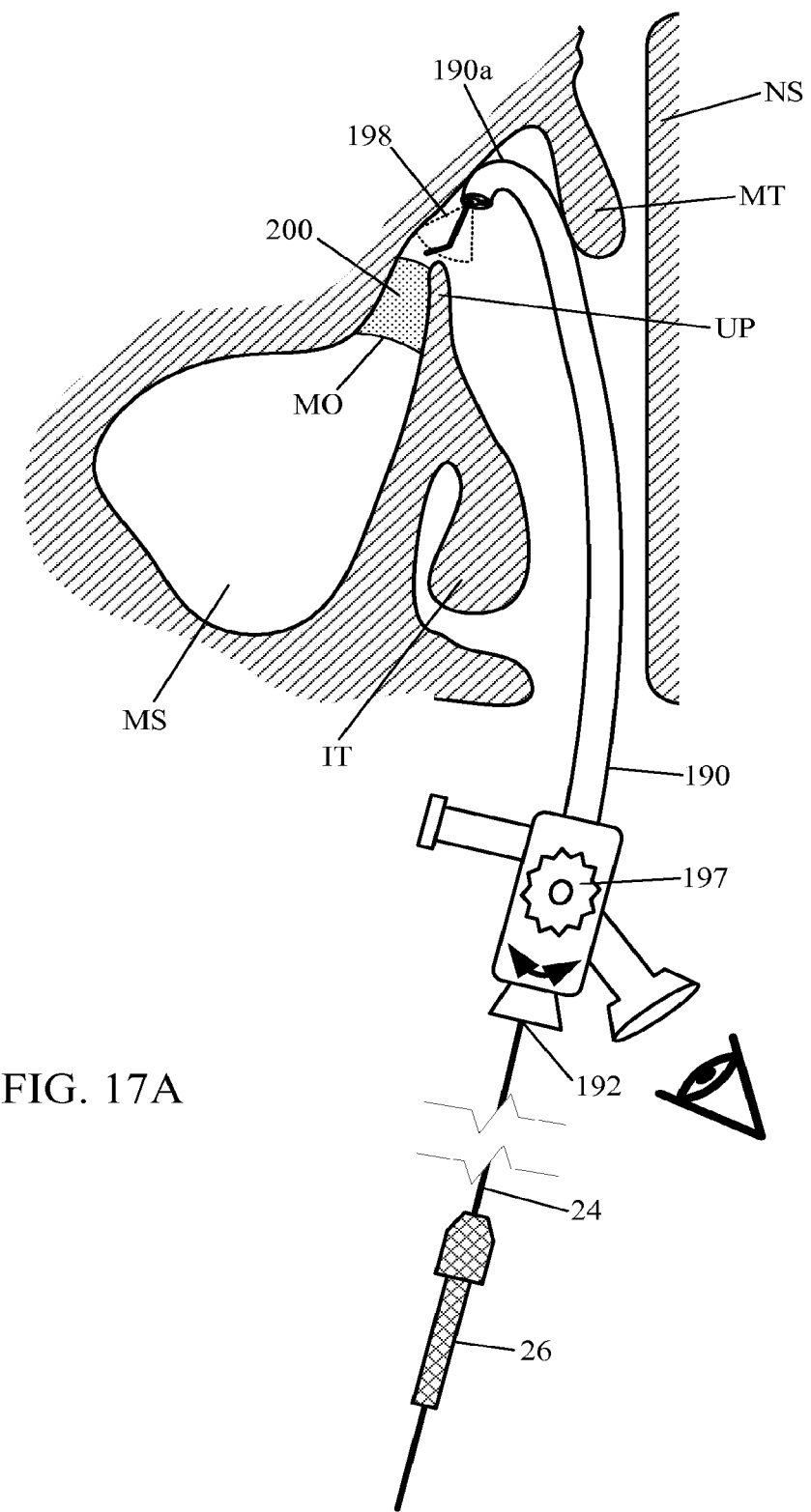
FIG. 17A shows additional methods and devices for accessing a sinus according to one of the invention.
Figure 17B:
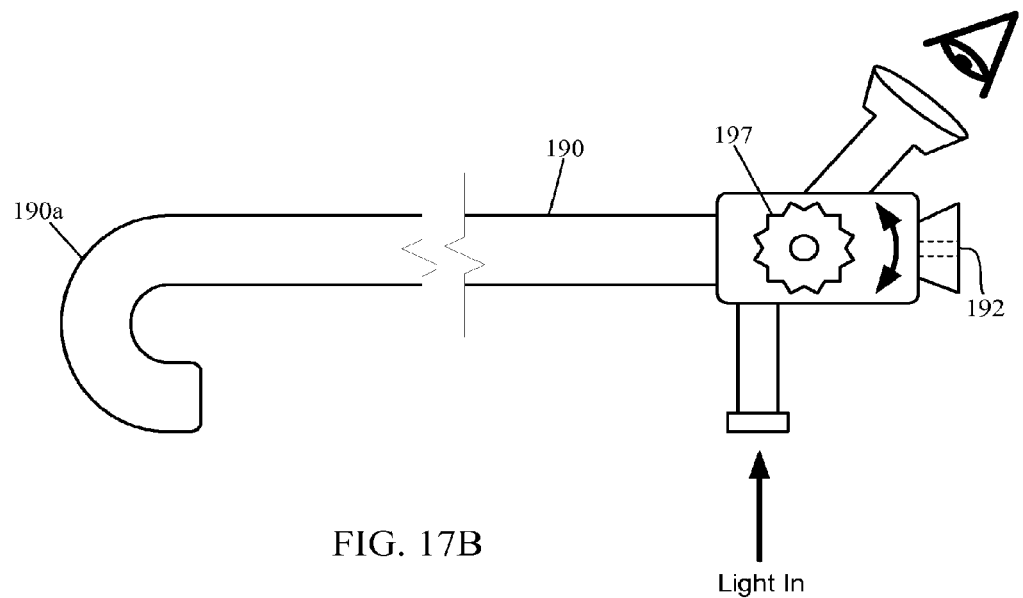
FIG. 17B shows an embodiment of a directable endoscope sheath as used in connection with FIG. 17A.
Figure 17C:
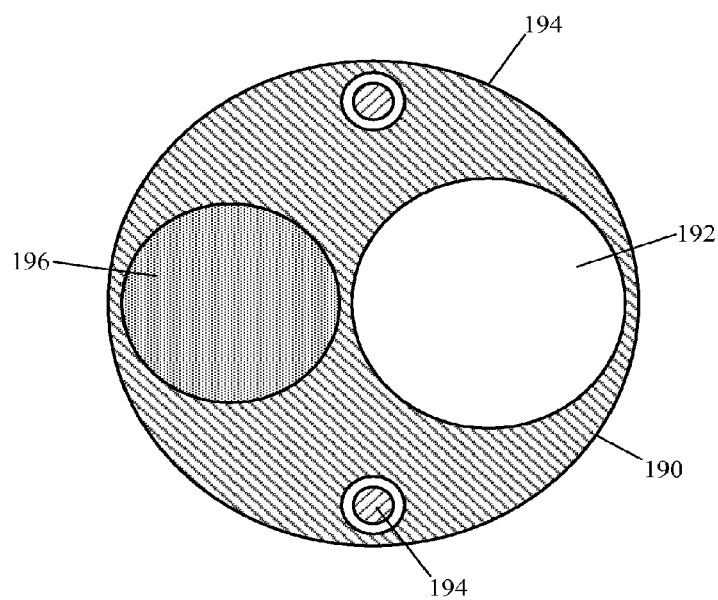
FIG. 17C is a cross-sectional view of the directable endoscope sheath of FIG. 17B.

Another alternative device and method for accessing a sinus ostium is illustrated in FIGS. 17A, 17B, and 17C. In this embodiment, a directable endoscope sheath 190 is provided that has a deflectable tip 190a. The directable endoscope sheath 190 is similar to the directable endoscope 152 of FIG. 14, but further includes a working channel or lumen 192, as best seen in FIG. 16C, together with the deflection wires 194 and optical fibers 196 (which contain both imaging and illuminating fibers). In use, the directable endoscope sheath 190 can be introduced into the nasal cavity relatively straight, so as to see straight ahead. When the directable endoscope sheath 192 is near the uncinate process UP, the tip 190a is deflected retrograde using, for instance, a deflection knob 197, so that the viewing field 198 is directed towards the sinus ostium MO which contains an obstruction 200. At this point, a wire guide 24 is positioned in the working lumen 192 and the ostium MO is accessed under visual observation.

In one preferred embodiment, the directable endoscope sheath 190 has a large enough working channel 192 that a balloon catheter 12 can be advanced into the sheath 190 over the wire 24. In this manner, a separate guide catheter 18 is not necessary. In yet another preferred embodiment, the working channel 192 is only large enough to accommodate the wire guide 24. This allows for the sheath 190 to have a reasonably small outer diameter. Once the wire 24 is positioned in the sinus, the directable endoscope sheath 190 is removed from the wire 24, leaving the wire 24 in position. Thereafter, a balloon catheter 12 can be installed over the wire 24 and into the sinus ostium MO for dilation.

Figure 18A:
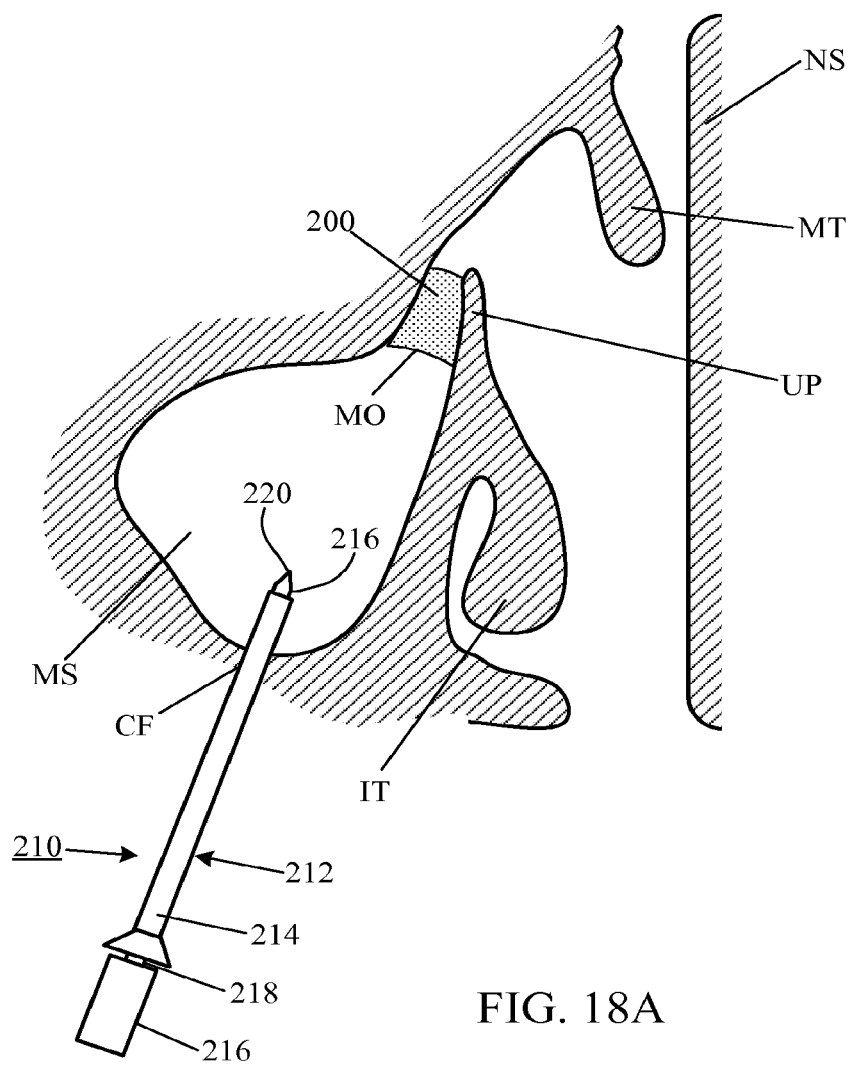
FIG. 18A illustrates methods and devices for accessing a sinus from an external location according to one aspect of the invention.
Figure 18B:
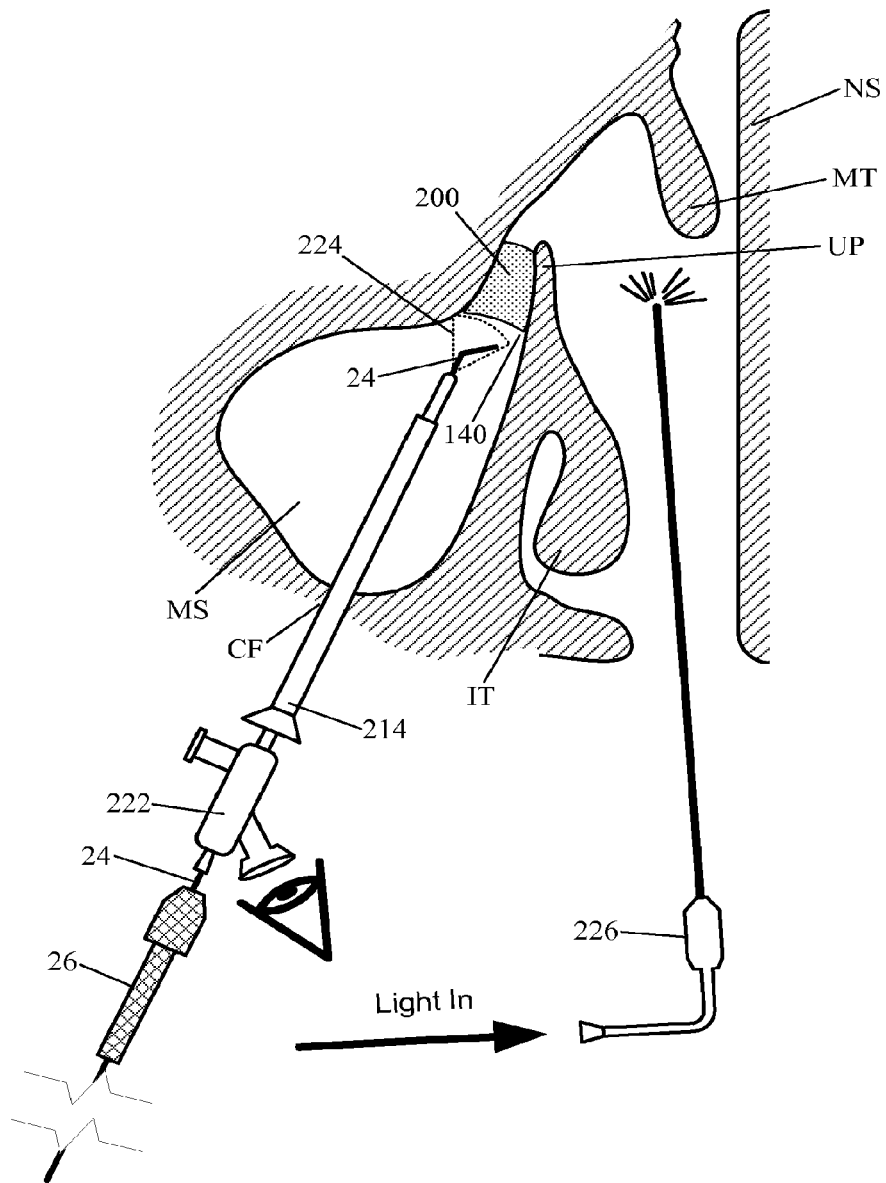
FIG. 18B illustrates additional methods and devices for accessing a sinus ostium from an external location according to one aspect of the invention.

FIGS. 18A and 18B illustrate a device 210 and method for accessing and dilating a sinus ostium (e.g., maxillary sinus ostium MO) via a direct sinus puncture technique, in contrast to a transnasal technique. This approach can generally be done with the frontal sinus FS and the maxillary sinus MS. While a description of the device 210 and process is provided for the maxillary sinus MS, it should be understood that similar access devices 210 can be used with the frontal sinus FS.

In FIG. 18A, a trocar 212 is shown being advanced into the maxillary sinus MS via the canine fossa CF approach. The trocar 212 includes a hollow cannula 214 and a needle 216 contained within the lumen 218 of the cannula 214. The needle 216 has a sharp tip 220 for penetrating the thin bone surrounding the sinus. The needle 216 may be a solid piece or having one or more lumens therein. Once the cannula 214 is inside the sinus, the needle 216 is then removed and the cannula 214 serves as a guide catheter for subsequent devices. As an alternative to a needle-cannula type of trocar 212, a hollow sharpened needle could be used as well.

Referring now to FIG. 18B, once the cannula 214 is in place, a wire guide 24 and an endoscope 222 can be introduced into the sinus. The cannula 214 is pointed towards the ostium MO, which points the viewing field 224 to the ostium MO. Manipulation of the wire guide 24 through use of a steering device 26 then delivers the wire guide 24 across the ostium MO which may contain a blockage 200 as is shown in FIG. 18B. Optionally, an illumination member 226 can be placed in the nasal cavity to "back-light" the ostium MO and enhance the ability for the ostium MO to be seen, further aiding the ability to direct the wire guide 24 across the ostium MO. Alternatively, a bright light placed at the nostril may be adequate to perform this back-lighting.

Figure 18C:
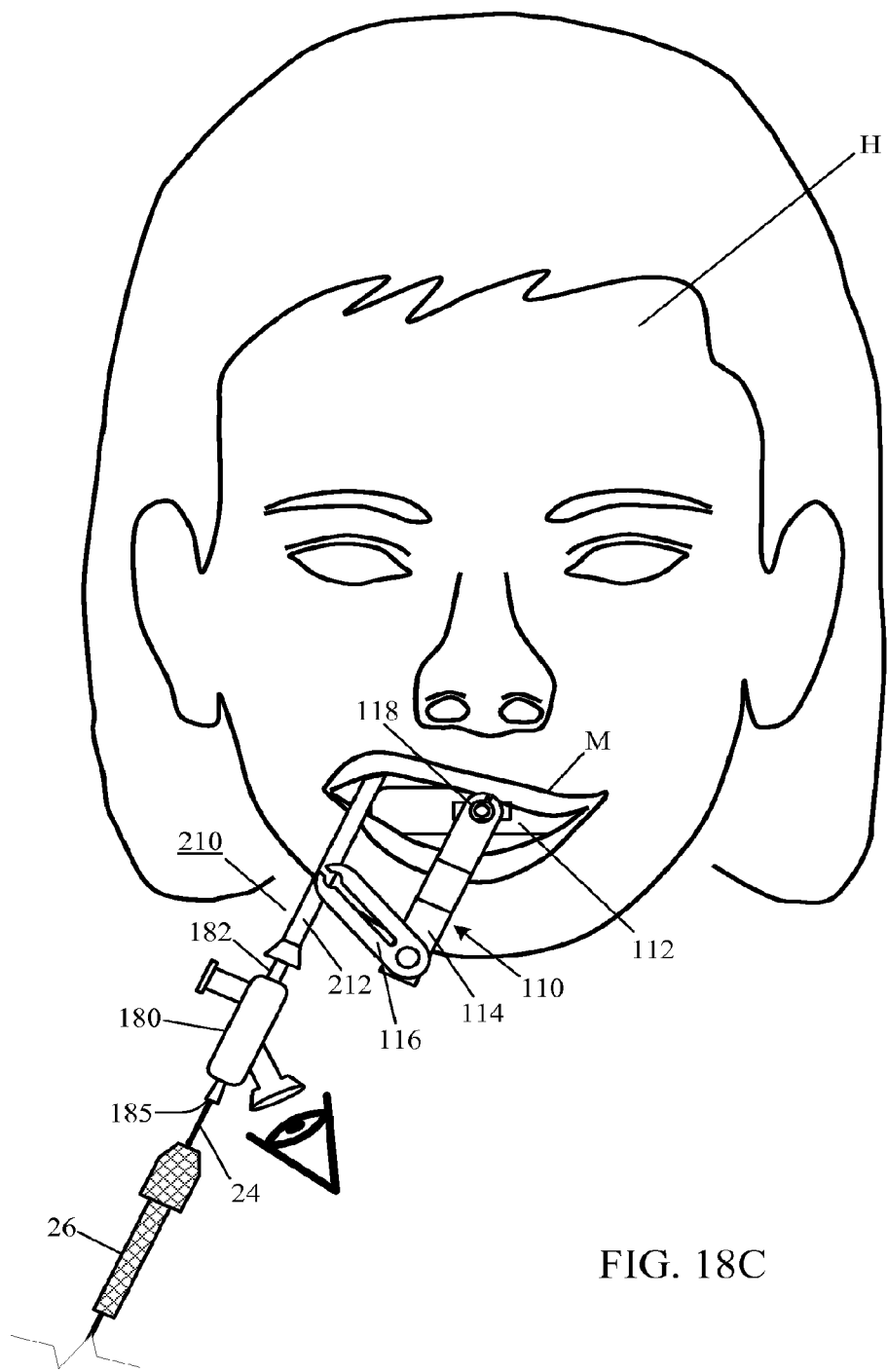
FIG. 18C illustrates further additional methods and devices for accessing a sinus ostium from an external location according to another aspect of the invention.

With the above-described "direct sinus puncture" technique such as through the canine fossa CF, various stabilization devices can be utilized to stabilize one or more of the various tools used for accessing and/or treating the ostium. For example, as shown in FIG. 18C, a stabilization device 110 is shown stabilizing the cannula 214. The stabilization device 110 could also be used to stabilize the wire guide 24, the endoscope 222, trocar 212, and/or the balloon catheter 12. Similarly, any of the previously described stabilization devices can be utilized with the direct sinus puncture techniques.

Figure 19A:
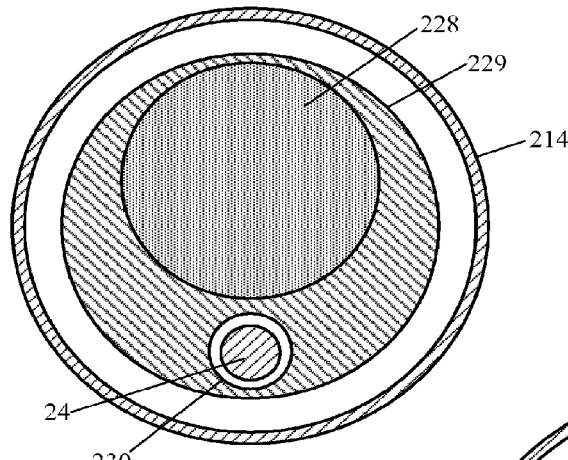
FIGS. 19A-19C are cross-sectional images depicting various arrangements of devices used in accessing a sinus ostium in connection with FIG. 18B.
Figure 19B:
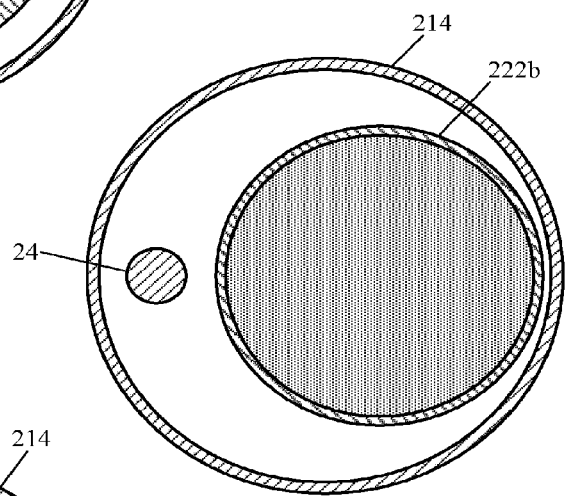
Figure 19C:
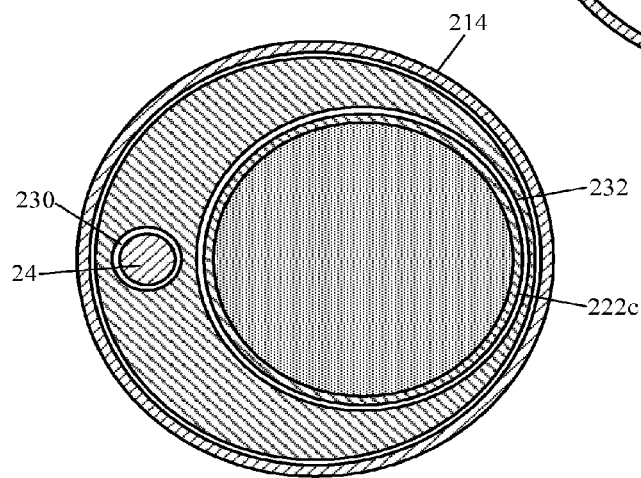

FIGS. 19A, 19B, and 19C illustrate various arrangements and types of endoscopes 222a, 222b, 222c that can be used with this canine fossa CF approach. In FIG. 19A, the endoscope 222a is a flexible visualization scope having a bundle of optical fibers 228. The endoscope 222a further includes a lumen 230 through which the wire guide 24 is fed. FIG. 19B shows a rigid endoscope 222b used next to the wire guide 24, inside cannula 214. FIG. 19C illustrates a similar arrangement to that shown in FIG. 19B, but with an additional dual lumen catheter 232 to better manage the positioning of the wire guide 24 relative to the rigid endoscope 222c. In all these approaches, the diameter of the endoscope 222a, 222b, 222c used is preferably small, about 0.5 mm to about 4 mm, and most preferably about 1 mm to about 2 mm. This allows for the use of a relatively small trocar and relatively small puncture size. Preferred trocar diameters are from 0.7 mm to 4.2 mm (depending on the size of the devices used with them), and more preferably from about 1 mm to 2.5 mm, and most preferably 1.2 to 2.0 mm.

Figure 20:
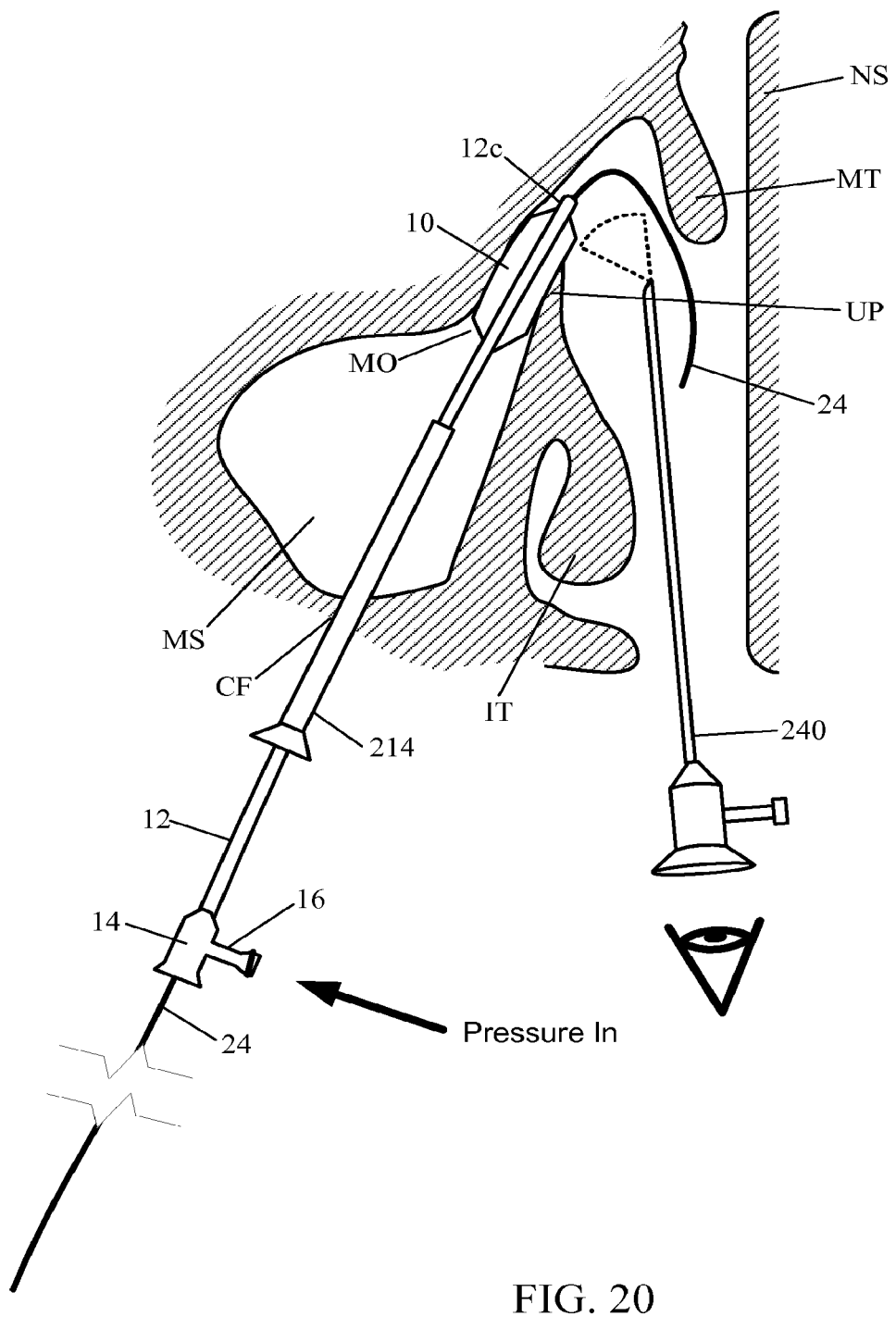
FIG. 20 illustrates methods and devices for treating a sinus ostium in one aspect of the invention.

FIG. 20 illustrates the introduction of a balloon dilation catheter 12 into the cannula 214 and into the sinus ostium MO, dilating the ostium MO, and deforming and/or remodeling the uncinate process UP. To aid in the positioning of the balloon 10, an optional endoscope 240 is placed in the nasal cavity may be used to visualize the catheter tip 12c relative to the uncinate process UP.

Alternatively, the position of the balloon 10 may not require "real time" visualization with an endoscope, if various markers on the wire guide and/or balloon catheter shaft as described earlier are utilized. For example, if the wire guide 24 includes markers, the marker that is seen at or near the ostium can be noted. Markers on the proximal portion of the wire guide 24 can then be used to determine the "depth" that the wire guide 24 has been advanced to reach the ostium. The balloon catheter 12 can then be advanced a distance over the wire guide 24 a predetermined distance on the wire guide 24, such that the balloon 10 is positioned at a desired position relative to the noted marker on the wire guide 24. Markers 62 on the shaft of the balloon catheter 12 can aid in this positioning. With this use of markers 62, the balloon 10 can be confidently positioned in the desired region of the sinus ostium. The desired length of the balloon can be selected by viewing the computed tomography (CT) scans of the patient, which are part of a standard diagnostic workup of the patient prior to any intervention.

Though not shown, once the maxillary ostium MO has been treated, the ethmoids and/or frontal sinuses ES, FS can also be treated by this same canine fossa access. The wire guide 24 can be manipulated into the ethmoids and/or frontals, with subsequent dilation of the ostia of these sinuses. Similar endoscopic visualization techniques as described above can also be utilized to assist in placement of the various devices such as the wire guide 24 to these locations. In the case of the ethmoids, it may be desirable to use a sharpened wire in lieu of a wire guide 24 to puncture into the wall of the ethmoid sinus air cells, followed by balloon dilation of the puncture.

As mentioned above, the frontal sinus FS can also be accessed directly from outside the skull, through the wall of the frontal sinus FS to facilitate treatment of the frontal sinus ostium FO. Rather than a trocar, the frontal sinus FS can be directly accessed through a mini trephination through the skin and the sinus wall, as is known in the art. With a mini-trephination, the access is performed with a drill tool. Once accessed, the frontal sinus ostium FO may be directly accessed with a wire guide 24. A preferred location for accessing the frontal sinus FS is through the floor of the frontal sinus FS. Since the frontal sinus FS is relatively small, and there is only one outflow tract and its position can be approximated relative to the nose, visualization may not be required to pass the wire guide 24 through the frontal sinus ostium FO and into the nasal cavity. Standard endoscopic visualization could be performed in the nasal cavity via the nostrils to observe the wire guide 24 after it passes into the nasal cavity. Subsequent to passing the wire guide 24 into the frontal ostium FO, a balloon dilation catheter 12 can be positioned in the ostium FO to dilate it.

Figure 21:
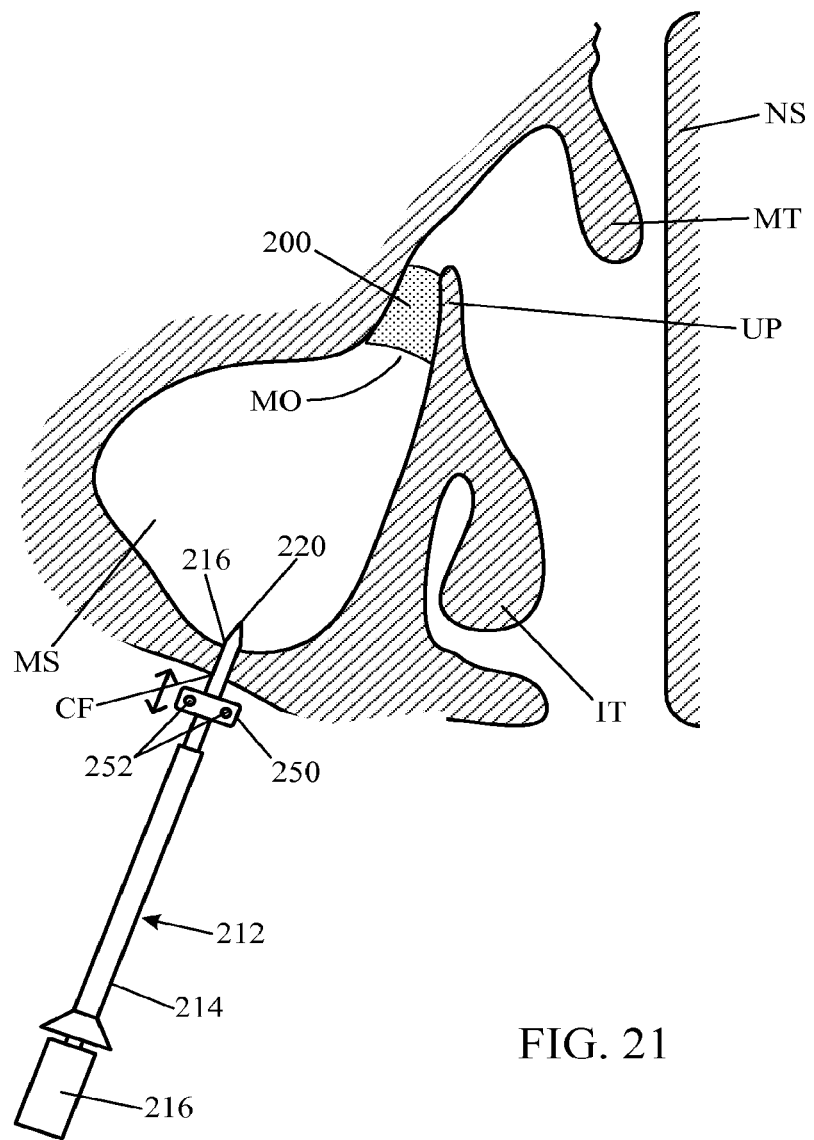
FIG. 21 shows an embodiment of a trocar in accordance with one aspect of the invention.

Although the maxillary sinus MS is easily accessible via the canine fossa CF, it is important to control the depth of the initial puncture so as to not inadvertently advance the needle 216 too far and potentially into the orbit O or elsewhere. FIG. 21 illustrates a trocar 212 with a stop 250 secured to a portion of the trocar 212. The stop 250 prevents the needle 216 from advancing too far into the sinus cavity. In one aspect, the stop 250 is clamped on to either the needle 216 or the cannula 214 at a predetermined position. In a preferred embodiment of the invention, the stop 250 is adjustable and/or removable with respect to the fixation point (e.g., needle 216 or cannula 214). For example, the stop 250 may include one or more tightening members 252 such as screws or the like that can be selectively tightened or loosen the stop 250. Once the trocar 212 is inserted up to the stop 250, the stop 250 is removed. The cannula 214 can then be advanced with little force, as the puncture site has already been made.

Figure 22:
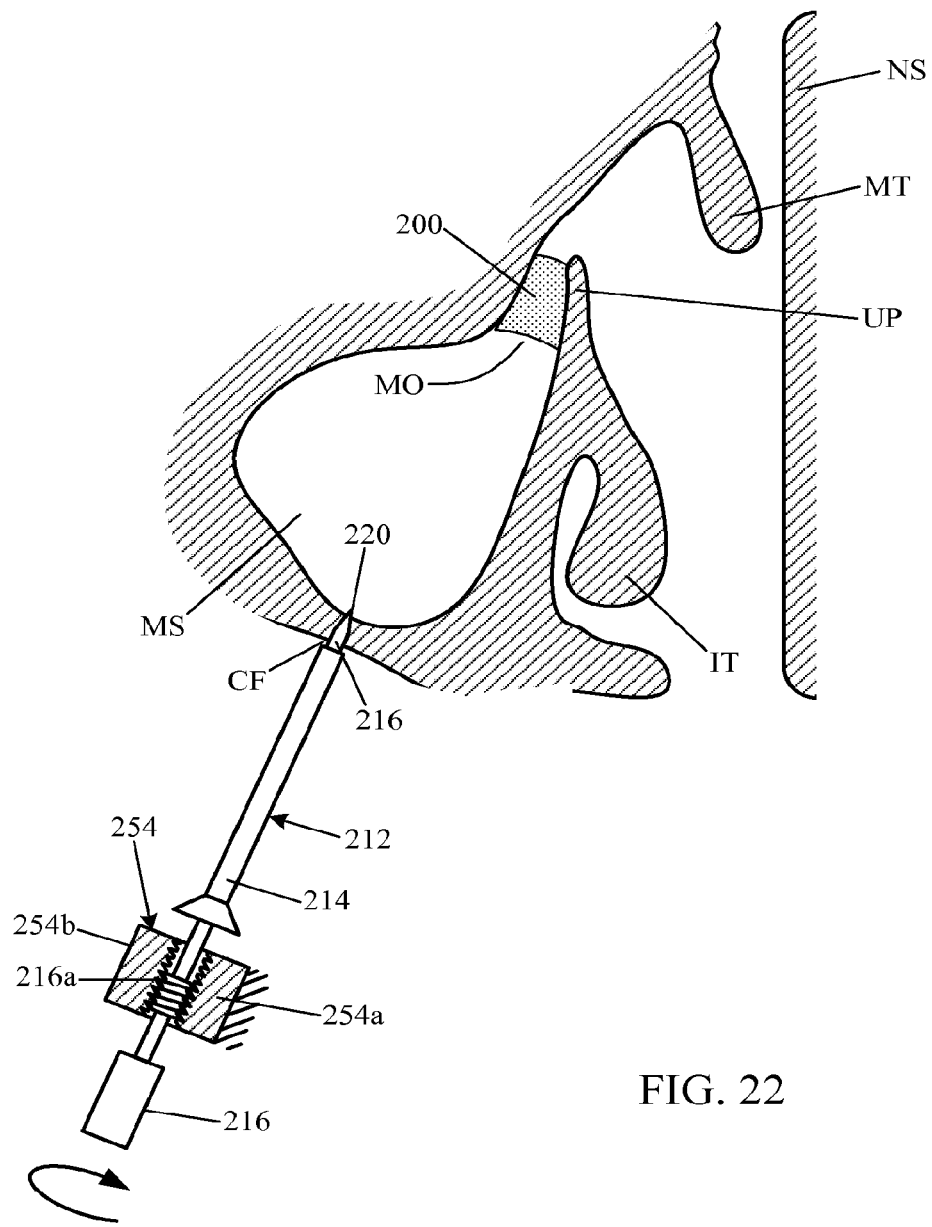
FIG. 22 shows another embodiment of a trocar according to another aspect of the invention.

FIG. 22 shows an alternative trocar 212 arrangement for improving the control of the puncturing into the canine fossa CF. Here, the needle 216 includes needle threads 216a located on an exterior surface thereof. The threads 216a of the needle 216 engage with a threaded hub 254 in a threaded interface. The threaded hub 254 may be in the form of a "clamshell" of two treaded pieces or halves 254a, 254b that surround and engage the needle threads 216a. The position of the threaded hub 254 may be held fast by attachment to a stabilizing device such as the stabilizing devices 80, 110 shown in FIGS. 8 and 10. The needle 216 is then advanced into the canine fossa CF by controlled rotation of the needle 216. Once the needle 216 has penetrated or traveled the desired amount, the threaded hub 254 is removed, and the cannula 214 is advanced to a desired position within the sinus. Alternatively, the threaded hub 254 could be attached to a stabilizing device 80, 110 in a manner that allows rotation of the threaded hub 254 about the needle threads 216a, by utilizing a bearing surface (not shown) with the stabilizing device 80, 110. The threaded hub 254 when rotated would controllably advance the needle 216 into the sinus. In this manner, the needle 216 is not rotated.

Figure 23A:
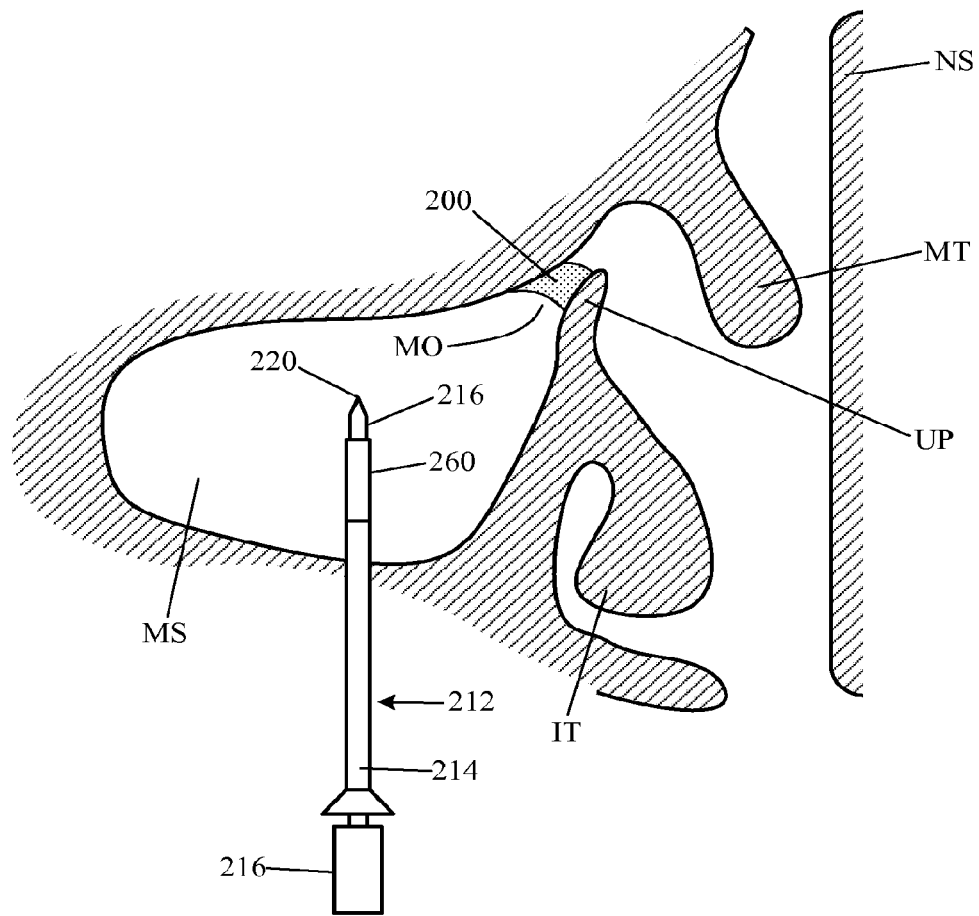
FIGS. 23A and 23B show additional methods and devices for accessing a sinus ostium from an external location according to one aspect of the invention.
Figure 23B:
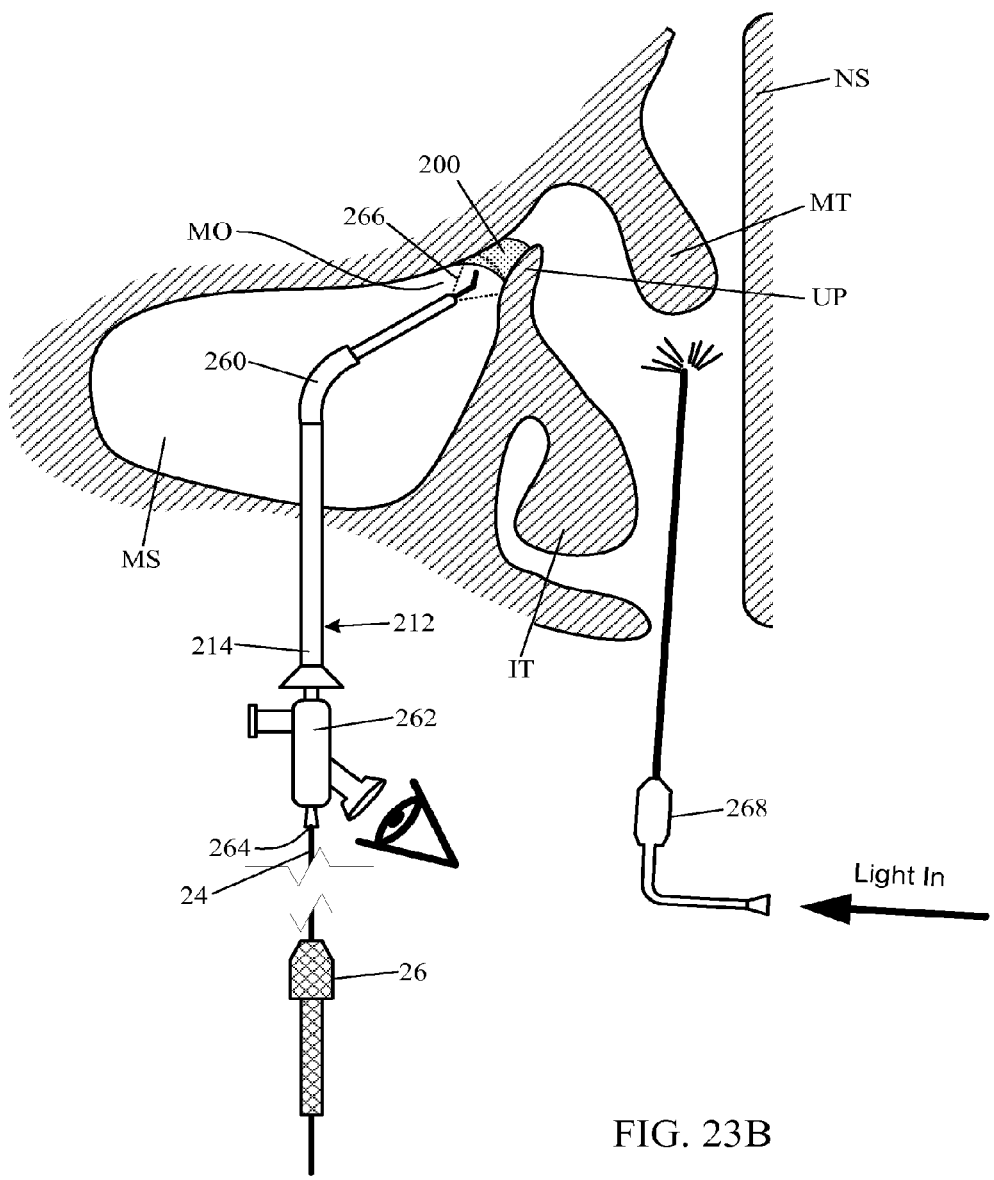

Sometimes the desired direction and positioning for placing the trocar 212 in the canine fossa CF does not provide good alignment with the location of the sinus ostium. In this case, a trocar 212 having a flexible tip 260 can be used, as shown in FIGS. 23A and 23B. In FIG. 23A, the cannula 214 has a somewhat flexible curved tip 260, that, in FIG. 23A, is maintained straight by the presence of the needle 216. This trocar 212 is advanced into the sinus. Upon removal of the needle 216, the flexible tip 260 takes on its curved shape, more oriented to the ostium MO. Thereafter a wire guide 24 is advanced across the ostium MO, preferably under the visual guidance of a flexible visualization scope 262 as shown in FIG. 23B. The visualization scope 262 is preferably dimensioned such that it can be slidably passed through the cannula 214. The flexible visualization scope 262 includes a lumen or passageway 264 for the wire guide 24. The flexible visualization scope 262 is able to be oriented to place the visualization field 266 within the vicinity of the ostium MO. Manipulation of the curved tip 260 of the cannula 214 can assist in directing the wire guide 24 to and through the ostium MO. Also as shown, the nasal cavity can be back-lit using an illumination member 268 to aid in seeing the ostium. Also, other tools and methods may be used as desired, such as, for example, the trocar 212 modifications illustrated in FIGS. 21 and 22.

Figure 24:
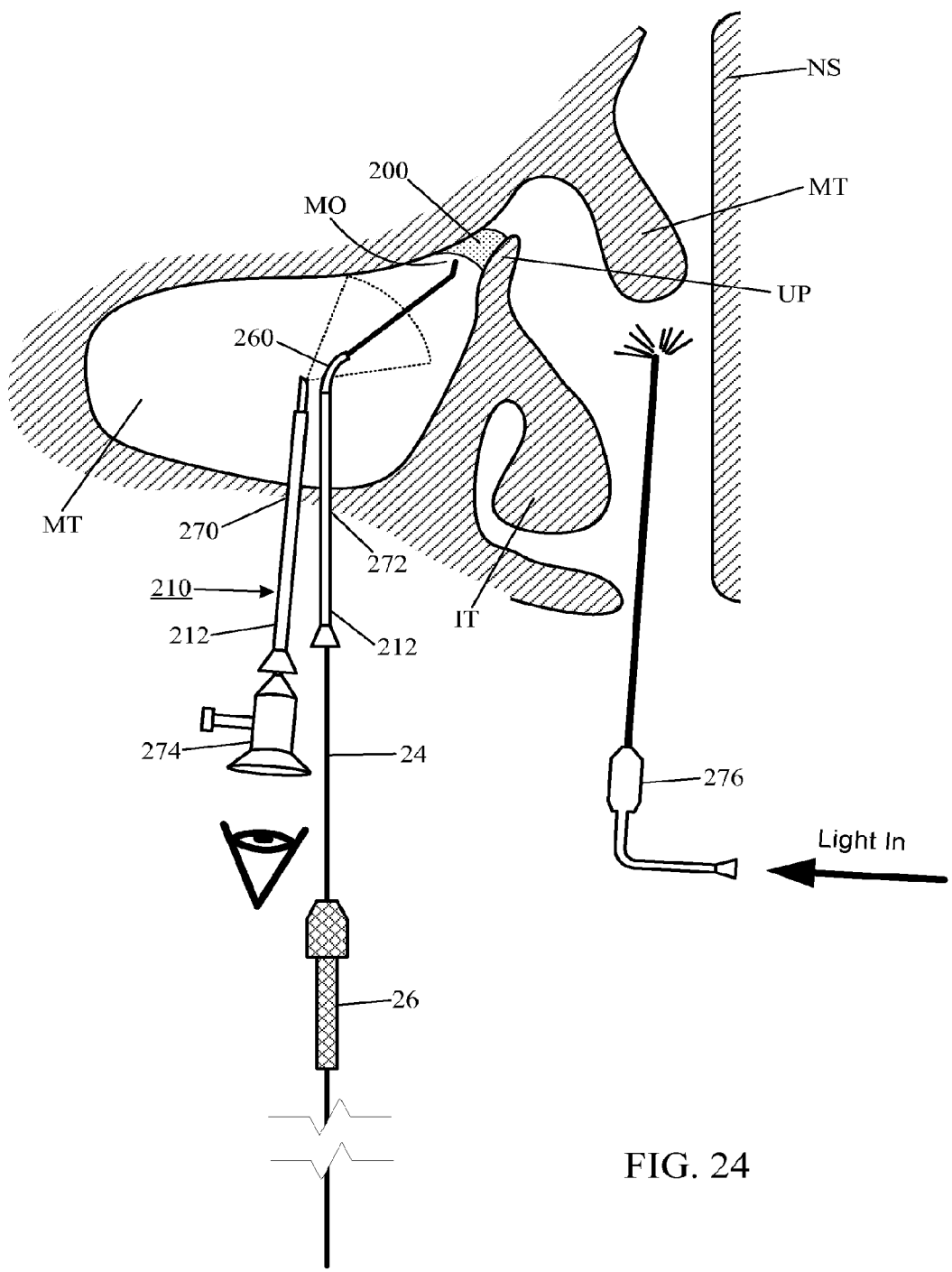
FIG. 24 shows additional methods and devices for accessing a sinus ostium from an external location according to another aspect of the invention.

FIG. 24 illustrates another device and method for accessing the maxillary sinus ostium MO via the canine fossa CF. In this embodiment, two small punctures 270, 272 are made, side-by-side in the canine fossa CF region. A puncture device 210 like that disclosed in FIG. 18A may be used. For example, a rigid endoscope 274 is positioned in the cannula 214 of the first puncture site 270. A wire guide 24 is then positioned in the cannula 214 of the second puncture site 272. One or more of the cannulas 212 may have a curved tip 260 to better access the maxillary sinus ostium MO. The wire guide 24 may then be positioned across the ostium MO under the visualization of the rigid endoscope 274. A balloon dilation catheter (not shown in FIG. 24) may then be advanced over the wire 24 to dilate the sinus. The ostial region may be back-lit using an illumination member 276.

Figure 25A:
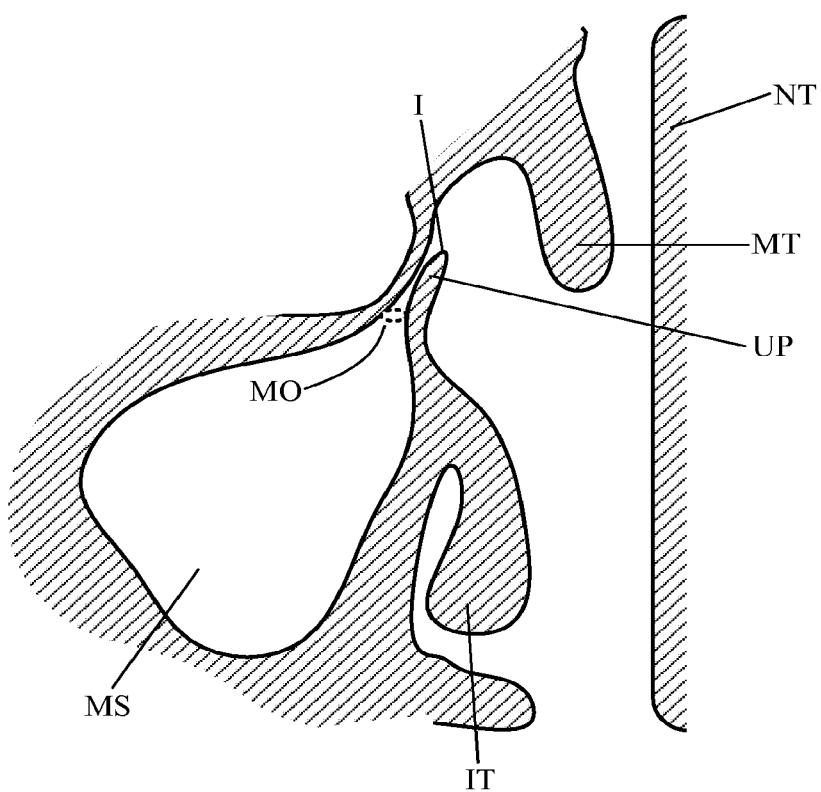
FIG. 25A is a coronal view showing anatomical features of the maxillary sinus.
Figure 25B:
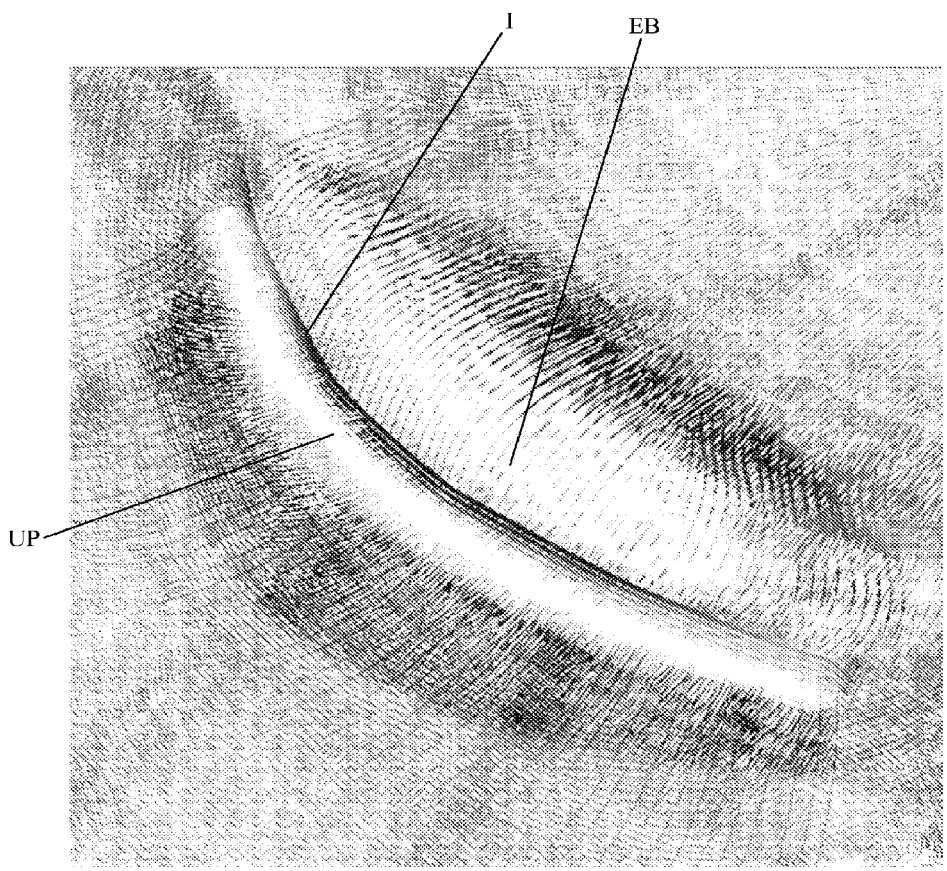
FIG. 25B is a sagittal view showing the anatomical features of FIG. 25A.

FIGS. 25A and 25B illustrate a common anatomical characteristic present in patients with sinusitis associated with the maxillaries, ethmoids, and frontals. The uncinate process UP is shown in close association with the opposite wall, typically on the ethmoid bulla EB. This condition creates a narrow slit-like space called the infundibulum I. The maxillary sinus ostium MO is actually located below (i.e., inferior to) the infundibulum I. FIG. 25B more clearly shows the "topography" of the structures of the uncinate process UP and ethmoid bulla EB. It is believed that a narrowed infundibulum I may be part of the condition leading to the patient's sinusitis, as well as one or more narrowed ostia. In some patents, a narrowed infundibulum I may be the sole anatomical cause leading to sinusitis.

The previously described approaches to dilating the maxillary sinus ostium MO may result in a widening of the infundibulum I by deforming or remodeling the uncinate process UP, as well as the widening of the ostium MO itself. However, in some patients, the uncinate process UP may not stay permanently deformed following removal of the dilation catheter 12.

Figure 26A:
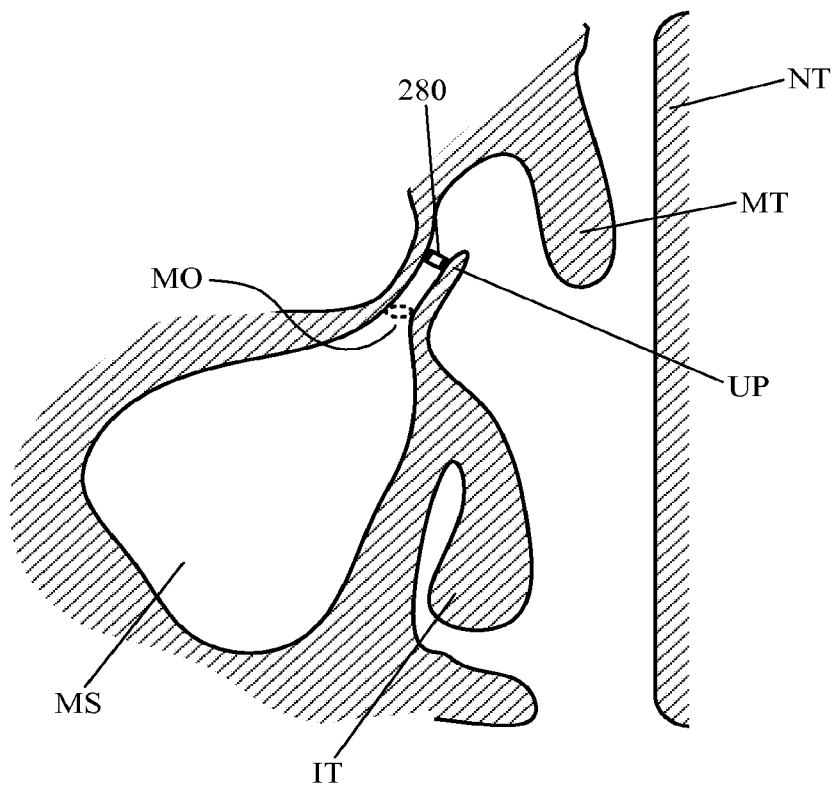
FIG. 26A is a coronal view illustrating methods and devices for the treatment of the uncinate process in accordance with one aspect of the invention.
Figure 26B:
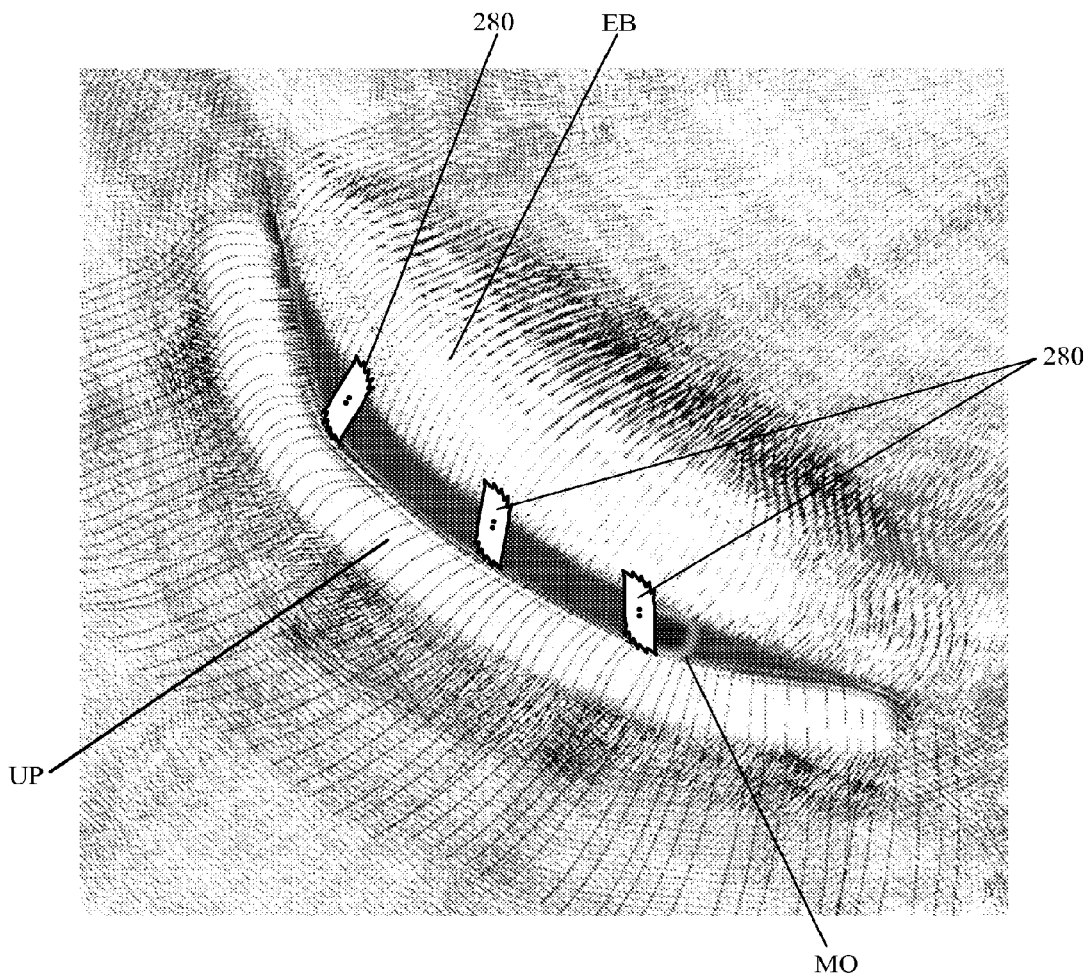
FIG. 26B is a sagittal view illustrating methods and devices for the treatment of the uncinate process in accordance with one aspect of the invention.

An alternative approach to widening the infundibulum I is illustrated in FIGS. 26A and 26B. One or more shim members 280 are placed in the gap of the infundibulum I to forcibly spread it away from the ethmoid bulla EB and improve drainage for the maxillary, frontal and portions of the ethmoid sinus. In one preferred aspect of the invention, the one or more shim members 280 are left in place after implantation. The shim members 280 may remain in place for a temporary period of time or permanently. The sinus ostium may still be dilated with the use of a balloon dilation catheter 12. FIG. 26B illustrates three such shim members 280 secured in the infundibulum I. As seen in FIG. 26B, the gap is widened to expose the maxillary sinus ostium MO.

Figure 27A:
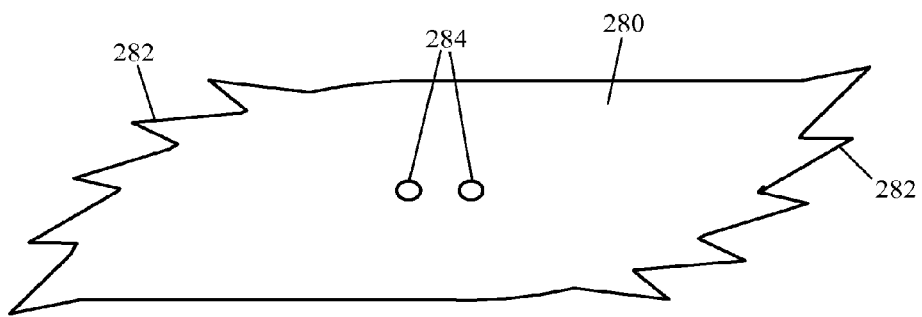
FIG. 27A is a top view of an embodiment of a shim member in accordance with one aspect of the invention.
Figure 27B:
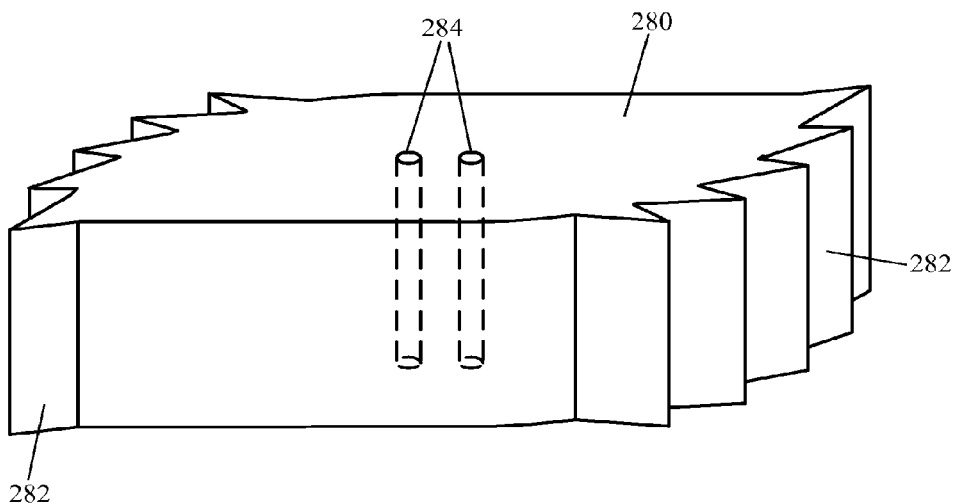
FIG. 27B is an isometric view of the shim member of FIG. 27A.

FIGS. 27A and 27B illustrate one preferred embodiment of a shim member 280. The shim members 280 may be dimensioned such that one or more sides are longer than the remaining sides. For example, the shim member 280 may be longer than it is wide, with a length dimension preferably about 1 mm to about 6 mm in length, and more preferably about 2 mm to about 4 mm in length. The shim members 280 may include one or more gripping members 282 on all or a portion of an exterior surface. The gripping members 282 may be formed as a serrated surface or even a plurality of teeth or similar projections. As seen in FIGS. 27A and 27B, the gripping members 282 are located on opposing sides of the shim member 280 to allow for the shim member 280 to be rotated into position and held in place.

Figure 28:
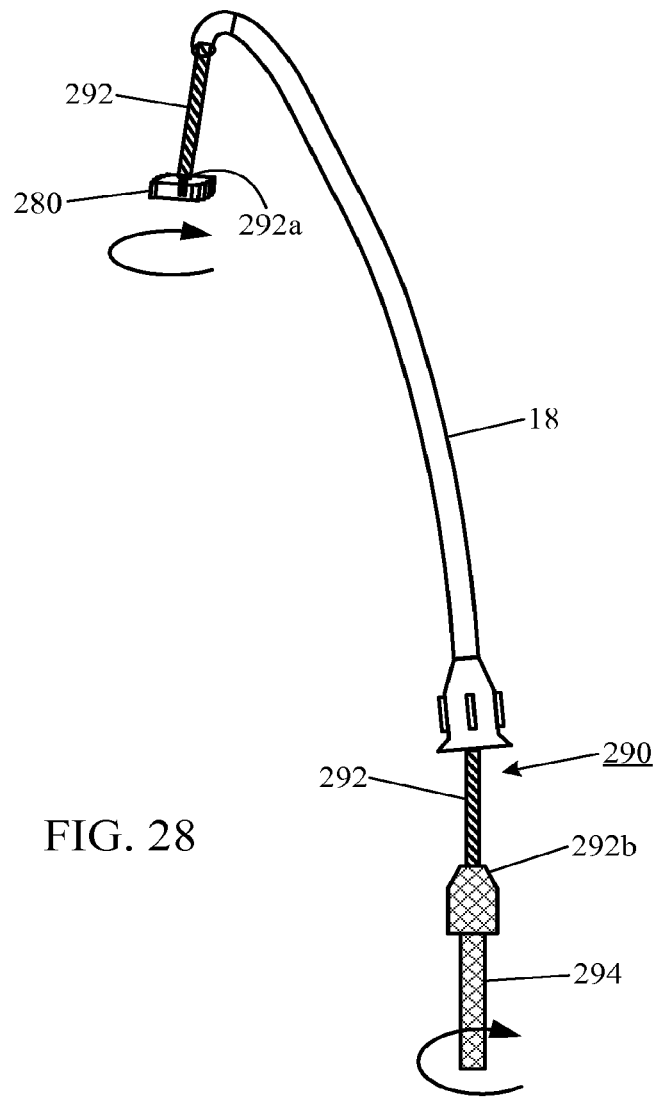
FIG. 28 is an embodiment of a shim member delivery device in accordance with one aspect of the invention.

The shim member 280 may include one or more engagement holes 284 that are used for the delivery of the shim member 280. For example, the engagement holes 284 may be dimensioned to fit on the distal end of a tool as shown in FIG. 28. The shim member 280 may be a permanent implant, or more preferably a degradable bioabsorbable implant. Suitable materials for a degradable shim member 280 include poly-lactic acid, poly-glycolic acid, poly-L-lactic acid or other materials such as those used in degradable sutures. It is believed that after the shim members 280 are implanted in the infundibulum I, the uncinate process UP will remodel over time to maintain a widened infundibulum.

FIG. 28 illustrates a delivery tool 290 for use in the delivery of the shim member(s) 280. The delivery tool 290 includes an elongate torque driver 292 constructed of a multi-layer, multi-filar drive shaft similar to that used in speedometer cables. The torque driver 292 is dimensioned to be positionable within a guide catheter 18 or the like. The shim member 280 is connected to the torque driver 292 at its distal end 292a. The proximal end 292b of the torque driver 292 is coupled to a handle 294 or the like that is used to rotate the torque driver 292 (and attached shim member 280) in the direction of the arrows shown in FIG. 28.

The guide catheter 18 is used to place the shim member 280 over the uncinate process UP and in the narrowed infundibulum I, initially in a narrow or "sideways" orientation. The torque driver 292 is then rotated by rotation of the handle 294. Rotation of about 60 to about 90 degrees will widen the infundibulum I as shown in FIG. 26B. The connection between the torque driver 292 and the shim member 280 is disconnected. This could be done, for example, by reversing the rotational direction of the torque handle 294 and causing a weakened portion of the connection to break. Alternatively, the torque driver 292 may be frictionally engaged with the holes 284 of the shim member 280. Retraction of the torque driver 292 in the proximal direction may disengage the torque driver 292 from the shim member 280. Once place, the one or more shim members 280 will maintain the infundibulum I in a widened condition, while minimizing the interruption of the mucosa by the presence of the shim member(s) 280.

Figure 29:
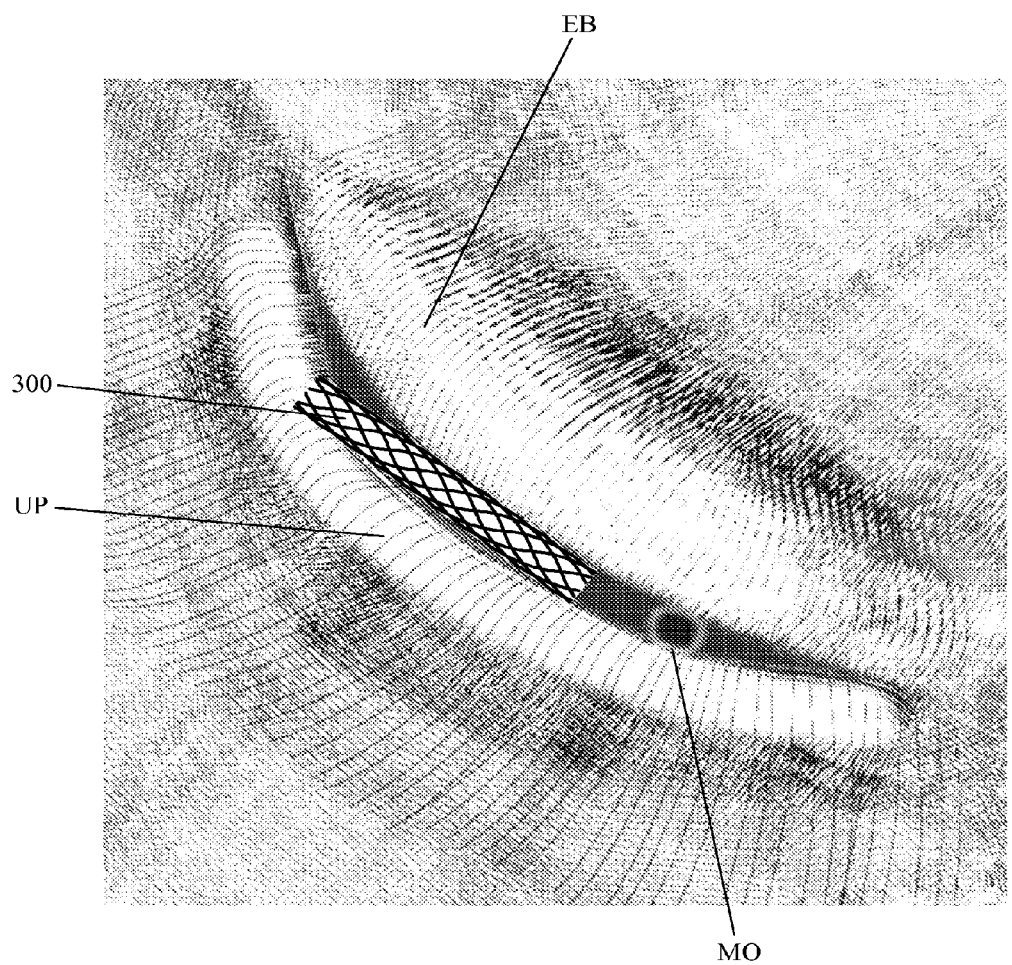
FIG. 29 illustrates a method and device for widening the infundibulum in accordance with another aspect of the invention.

Alternatively, as shown in FIG. 29, the infundibulum I can be widened by delivery of an expandable stent 300, oriented more or less in the infundibulum I. This stent 300 can be similar to that used in coronary stenting procedures, and can be either "self-expanding" or "balloon expandable." The geometry of the stent 300 may be tubular as is shown in FIG. 29. The stent 300 can be placed in the infundibulum I using a balloon catheter 12 and a wire guide 24. As one example, the stent 300 may be positioned via a transnasal approach wherein the wire guide 24 is directed along the infundibulum I up towards the frontal sinus ostium FO (as shown in FIG. 3C) and then deployed between the uncinate process UP and the ethmoid bulla EB.

While embodiments of the present invention have been shown and described, various modifications may be made without departing from the scope of the present invention. The invention, therefore, should not be limited, except to the following claims, and their equivalents.

What is claimed is:

1. A method of dilating tissue of a sinus drainage pathway in a patient, comprising:
   directing a distal tip of a wire guide through a nasal passage and into a first test position within the sinus system of the patient, wherein the wire guide extends through a guide catheter and wherein a proximal end of the guide catheter is removably secured to a distal end of a handle and the wire guide extends through a steering device, and wherein the handle defines a recess that opens along a longitudinal length of a side surface of the handle, and wherein advancing the wire guide includes sliding the steering device distally along the recess of the handle in a direction parallel to a major longitudinal axis of the handle, and wherein directing the distal tip of the wire guide includes rotating the wire guide relative to the handle by rotating the steering device and wherein the steering device is configured to allow rotation of the wire guide through complete revolutions;

emitting light at or adjacent the distal tip of the wire guide at the first test position;

externally viewing the light through skin of the patient to confirm whether the first test position and the distal tip of the wire guide is within a desired cavity of the sinus system;

repositioning the distal tip of the wire guide to a second test position if externally viewing the light does not confirm that the first test positions is within the desired cavity;

directing a distal portion of a balloon catheter out the distal end of the guide catheter and into the desired location within a drainage pathway of the desired cavity, wherein the distal portion of the balloon catheter includes an inflatable balloon; and inflating the balloon to dilate tissue of the sinus drainage pathway at the desired location.

2. The method of claim 1, wherein an ambient level of light in an environment surrounding the patient is reduced when the light through the skin of the patient is externally viewed as compared to the ambient level of light during any of the remaining operations.

3. The method of claim 1, wherein the wire guide is disposed within the balloon catheter when the balloon is inflated at the desired location.

4. The method of claim 1, wherein a fiber optic catheter is disposed over the wire guide.

5. The method of claim 4, wherein the light viewed through the skin of the patient is emitted from a distal tip of the fiber optic catheter.

6. The method of claim 1, wherein the handle is configured to receive the wire guide and wherein the steering device is configured to advance the wire guide through the guide catheter while the steering device advances with the wire guide.

7. The method of claim 6, wherein the handle is held with one hand while an endoscope is held with a second hand, wherein the steering device is configured to advance the wire guide through the handle.

8. The method of claim 7, further including manipulating a knob disposed on the endoscope to direct a viewing field of the endoscope towards a sinus ostium.

9. A method of dilating tissue of a sinus drainage pathway in a patient, comprising:

directing a distal tip of a wire guide through a nasal passage wherein the wire guide extends through a guide catheter and into a first test position of the patient, wherein the first test position is suspected of being within a desired paranasal sinus cavity of the patient, wherein a proximal end of the guide catheter is secured to a distal end of a handle and the wire guide extends through a steering device, and wherein the handle defines a recess that opens along a longitudinal length of a side surface of the handle, and wherein advancing the wire guide includes sliding the steering device distally along the recess of the handle in a direction parallel to a major longitudinal axis of the handle, and wherein directing the distal tip of the wire guide includes rotating the wire guide relative to the handle by rotating the steering device and wherein the steering device is configured to allow rotation of the wire guide through complete revolutions;

emitting light at the first test position;

externally viewing the light through skin of the patient to confirm whether the first test position is within the desired paranasal sinus cavity;

repositioning the distal tip of the wire guide to a second test position if externally viewing the light does not confirm that the first test position is within the desired paranasal sinus cavity;

directing a distal portion of a balloon catheter out the distal end of the guide catheter and into the desired location within a drainage pathway of the desired paranasal sinus cavity after confirming that the distal tip of the wire guide is within the desired paranasal sinus cavity, wherein the distal portion of the balloon catheter includes an inflatable balloon; and inflating the balloon to dilate tissue of the drainage pathway at the desired location.

10. The method of claim 9, wherein the light is emitted before the distal portion of the balloon catheter is directed out of the distal end of the guide catheter.

11. The method of claim 10, wherein the distal portion of the balloon catheter is directed over the wire guide and into the desired location.

12. The method of claim 11, further comprising directing the distal end of the guide catheter while viewing the distal end of the guide catheter with an endoscope, and actuating a knob disposed on the endoscope to reposition a viewing field of the endoscope towards a sinus ostium.

13. The method of claim 12, wherein the handle is removably secured to the guide catheter and wherein the handle is configured to receive the wire guide and wherein the steering device advances the wire guide through the guide catheter.

14. The method of claim 13, further including directing the distal tip of the wire guide through the handle and into the guide catheter.

15. The method of claim 14, wherein the proximal end of the guide catheter includes a hub and the hub is removably secured to a distal end of the handle with a frictional fit.

16. The method of claim 15, wherein the handle is held in a first hand and the endoscope is held in a second hand.

17. The method of claim 16, wherein an ambient level of light in an environment surrounding the patient is reduced when the light through the skin of the patient is externally viewed as compared to the ambient level of light during any of the remaining method operations.

18. The method of claim 11, wherein the handle is removably secured to the guide catheter and wherein the handle is configured to receive the wire guide and wherein the steering device rotates with the wire guide as the wire guide rotates within the guide catheter.

19. The method of claim 18, further including directing the distal tip of the wire guide through the handle and into the guide catheter.

20. The method of claim 19, wherein the proximal end of the guide catheter includes a hub and the hub is removably secured to a distal end of the handle with a frictional fit.

21. The method of claim 20, wherein the steering device advances the wire guide through the guide catheter while the steering device advances with the wire guide.

22. The method of claim 21, wherein the steering device is configured to both rotate and advance the wire guide within the guide catheter.

23. The method of claim 22, wherein the handle is held in a first hand and an endoscope is held in a second hand, and wherein the distal end of the guide catheter is directed to a desired location within a nasal passageway of the patient while observing through the endoscope.

24. The method of claim 23, wherein the light is externally viewed through the skin of the patient at ambient level of light that is reduced as compared to the ambient level of light used when conducting any of the remaining method operations.

25. A method of dilating tissue of a sinus drainage pathway in a patient, comprising:
- directing a distal tip of a wire guide through a nasal passage wherein the wire guide extends through a guide catheter and into a first test position of the patient, wherein the first test position is suspected of being within a desired paranasal sinus cavity of the patient, and wherein a proximal end of the guide catheter is secured to a distal end of a handle and the wire guide extends through a steering device, and wherein the handle defines a recess that opens along a longitudinal length of a side surface of the handle, and wherein advancing the wire guide includes sliding the steering device distally along the recess of the handle in a direction parallel to a major longitudinal axis of the handle, and wherein directing the distal tip of the wire guide includes rotating the wire guide relative to the handle by rotating the steering device and wherein the steering device is configured to allow rotation of the wire guide through complete revolutions;
- emitting light at the first test position;
- externally viewing the light through skin of the patient to confirm that the first test position is not within a desired paranasal sinus cavity;
- repositioning the distal tip of the wire guide to a second test position, wherein the second test position is suspected of being within the desired paranasal sinus cavity of the patient;
- externally viewing the light through skin of the patient to confirm that the second test position is within the desired paranasal sinus cavity;
- directing a distal portion of a balloon catheter out the distal end of the guide catheter and into a desired location within a drainage pathway of the desired paranasal sinus cavity after confirming that the distal tip of the wire guide is within the desired paranasal sinus cavity, wherein the distal portion of the balloon catheter includes an inflatable balloon; and
- inflating the balloon to dilate tissue of the drainage pathway at the desired location.

26. The method of claim 25, wherein the handle is configured to receive the wire guide and wherein the steering device is configured to advance with the wire guide relative to the guide catheter.

* * * * *